United States Patent
Hostetler et al.

(10) Patent No.: US 9,775,852 B2
(45) Date of Patent: *Oct. 3, 2017

(54) ACYCLIC NUCLEOSIDE PHOSPHONATE DIESTERS

(71) Applicant: The Regents of the University of California, Oakland, CA (US)

(72) Inventors: Karl Y. Hostetler, Del Mar, CA (US); James R. Beadle, San Diego, CA (US); Nadejda Valiaeva, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,209

(22) Filed: Jun. 10, 2016

(65) Prior Publication Data

US 2017/0002033 A1    Jan. 5, 2017

Related U.S. Application Data

(63) Continuation of application No. 14/874,027, filed on Oct. 2, 2015, now Pat. No. 9,387,217, which is a continuation of application No. 14/463,908, filed on Aug. 20, 2014, now Pat. No. 9,156,867, which is a continuation of application No. 14/211,235, filed on Mar. 14, 2014, now Pat. No. 8,835,630.

(60) Provisional application No. 61/793,993, filed on Mar. 15, 2013.

(51) Int. Cl.
| | |
|---|---|
| *A61K 31/675* | (2006.01) |
| *C07F 9/6561* | (2006.01) |
| *C07F 9/6512* | (2006.01) |
| *C07F 9/6558* | (2006.01) |

(52) U.S. Cl.
CPC .......... *A61K 31/675* (2013.01); *C07F 9/6561* (2013.01); *C07F 9/65121* (2013.01); *C07F 9/65616* (2013.01); *C07F 9/65583* (2013.01)

(58) Field of Classification Search
CPC .................... C07F 9/65616; C07F 9/65121
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,328,245 A | 5/1982 | Yu et al. |
| 4,409,239 A | 10/1983 | Yu |
| 4,410,545 A | 10/1983 | Yu et al. |
| 4,522,811 A | 6/1985 | Eppstein et al. |
| 4,659,825 A | 4/1987 | Holy et al. |
| 4,724,233 A | 2/1988 | De Clercq et al. |
| 4,808,716 A | 2/1989 | Holy et al. |
| 4,861,760 A | 8/1989 | Mazuel et al. |
| 4,911,920 A | 3/1990 | Jani et al. |
| 5,033,352 A | 7/1991 | Kellogg et al. |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,212,162 A | 5/1993 | Missel et al. |
| 5,323,907 A | 6/1994 | Kalvelage |
| 5,354,556 A | 10/1994 | Sparks et al. |
| 5,403,841 A | 4/1995 | Lang et al. |
| 5,484,809 A | 1/1996 | Hostetler et al. |
| 5,532,225 A | 7/1996 | Reist et al. |
| 5,571,534 A | 11/1996 | Jalonen et al. |
| 5,591,767 A | 1/1997 | Mohr et al. |
| 5,639,476 A | 6/1997 | Oshlack et al. |
| 5,641,763 A | 6/1997 | Holy et al. |
| 5,650,510 A | 7/1997 | Webb, II et al. |
| 5,650,520 A | 7/1997 | Hao et al. |
| 5,656,745 A | 8/1997 | Bischofberger et al. |
| 5,674,533 A | 10/1997 | Santus et al. |
| 5,717,095 A | 2/1998 | Arimilli et al. |
| 5,726,174 A | 3/1998 | Kim et al. |
| 5,733,566 A | 3/1998 | Lewis |
| 5,733,896 A | 3/1998 | Holy et al. |
| 5,798,340 A | 8/1998 | Bischofberger et al. |
| 5,817,647 A | 10/1998 | Casara et al. |
| 5,827,831 A | 10/1998 | Hostetler et al. |
| 5,840,716 A | 11/1998 | Ubasawa et al. |
| 5,854,228 A | 12/1998 | Webb, II et al. |

(Continued)

FOREIGN PATENT DOCUMENTS

| | | |
|---|---|---|
| CN | 1426418 A | 6/2003 |
| CN | 1805966 A | 7/2006 |

(Continued)

OTHER PUBLICATIONS

Holy et al. (Collection Czechoslovak Chem. Cornrnun. [vol. 52] [1987]).*

Aldern et al., "Update and Metabolism of Cidofovir and Oleyloxyethyl-cidofovir in Human Papillomavirus Postive ME-180 Human Cervical Cancer Cells" Abstract 173 *Antiviral Research* (2007) 74(3):A83.

Beadle et al., "Synthesis and Antiviral Evaluation of Alkoxyalkyl Derivatives of 9-(S)-(3-Hydroxy-2-phosphonomethoxpropyl)adenine against Cytomegalovirus", *Journal of Medicinal Chemistry*, 2006, 49:2010-2015.

(Continued)

*Primary Examiner* — Bruck Kifle

(74) *Attorney, Agent, or Firm* — Mintz Levin Cohn Ferris Glovsky and Popeo, P.C.

(57) ABSTRACT

The present disclosure relates, inter alia, to compositions and methods for treating viral diseases and cancer. There are disclosed lipophilic antiviral and anticancer acyclic nucleoside phosphonate diesters, preparation thereof, and methods of using the compounds to treat viral diseases and cancer.

45 Claims, 1 Drawing Sheet

(56) References Cited

U.S. PATENT DOCUMENTS

| | | |
|---|---|---|
| 5,869,467 A | 2/1999 | Holy et al. |
| 5,877,166 A | 3/1999 | Reist et al. |
| 5,886,179 A | 3/1999 | Arimilli et al. |
| 5,922,696 A | 7/1999 | Casara et al. |
| 5,955,610 A | 9/1999 | Nguyen-Ba et al. |
| 5,977,061 A | 11/1999 | Holy et al. |
| 6,005,107 A | 12/1999 | Nguyen-Ba et al. |
| 6,037,335 A | 3/2000 | Takashima et al. |
| 6,057,305 A | 5/2000 | Holy et al. |
| 6,127,540 A | 10/2000 | Nguyen-Ba et al. |
| 6,197,775 B1 | 3/2001 | Ubasawa et al. |
| 6,225,460 B1 | 5/2001 | Bischofberger et al. |
| 6,350,458 B1 | 2/2002 | Modi |
| 6,444,656 B1 | 9/2002 | Nguyen-Ba et al. |
| 6,448,392 B1 | 9/2002 | Hostetler et al. |
| 6,455,571 B1 | 9/2002 | Maring et al. |
| 6,562,861 B1 | 5/2003 | Babu et al. |
| 6,599,887 B2 | 7/2003 | Hostetler et al. |
| 6,653,296 B1 | 11/2003 | Holy et al. |
| 6,716,825 B2 | 4/2004 | Hostetler et al. |
| 6,767,900 B2 | 7/2004 | Ubasawa et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,452,898 B2 | 11/2008 | Hostetler et al. |
| 7,652,001 B2 | 1/2010 | Hostetler et al. |
| 7,687,480 B2 | 3/2010 | Hostetler et al. |
| 7,749,983 B2 | 7/2010 | Hostetler et al. |
| 7,790,703 B2 | 9/2010 | Hostetler et al. |
| 7,994,143 B2 | 8/2011 | Hostetler et al. |
| 8,008,308 B2 | 8/2011 | Hostetler et al. |
| 8,088,754 B2 | 1/2012 | Cheng et al. |
| 8,101,745 B2 | 1/2012 | Hostetler et al. |
| 8,163,718 B2 | 4/2012 | Birkus et al. |
| 8,193,167 B2 | 6/2012 | Hostetler et al. |
| 8,309,565 B2 | 11/2012 | Hostetler et al. |
| 8,318,700 B2 | 11/2012 | Hostetler et al. |
| 8,569,321 B2 | 10/2013 | Ware et al. |
| 8,614,200 B2 | 12/2013 | Painter et al. |
| 8,710,030 B2 | 4/2014 | Hostetler et al. |
| 8,835,630 B1 | 9/2014 | Hostetler et al. |
| 8,846,643 B2 | 9/2014 | Hostetler et al. |
| 8,889,658 B2 | 11/2014 | Hostetler et al. |
| 8,962,829 B1 | 2/2015 | Ware et al. |
| 8,993,542 B2 | 3/2015 | Lanier et al. |
| 9,006,218 B2 | 4/2015 | Almond et al. |
| 9,156,867 B2 | 10/2015 | Hostetler et al. |
| 9,206,208 B2 | 12/2015 | Hostetler et al. |
| 9,387,217 B2 | 7/2016 | Hostetler et al. |
| 9,475,832 B2 | 10/2016 | Hostetler et al. |
| 9,493,493 B2 | 11/2016 | Hostetler et al. |
| 2003/0109498 A1 | 6/2003 | Yuasa et al. |
| 2004/0019232 A1 | 1/2004 | Hostetler et al. |
| 2004/0023921 A1 | 2/2004 | Hong et al. |
| 2004/0023928 A1 | 2/2004 | Colacino |
| 2004/0127735 A1 | 7/2004 | Hostetler et al. |
| 2005/0176673 A1 | 8/2005 | Hostetler et al. |
| 2005/0182019 A1 | 8/2005 | Hostetler et al. |
| 2005/0192246 A1 | 9/2005 | Hostetler et al. |
| 2006/0281706 A1 | 12/2006 | Hostetler et al. |
| 2007/0161602 A1 | 7/2007 | Hostetler et al. |
| 2008/0103115 A1 | 5/2008 | Hostetler et al. |
| 2008/0221061 A1 | 9/2008 | Hostetler et al. |
| 2009/0149400 A1 | 6/2009 | Cheng et al. |
| 2009/0291922 A1 | 11/2009 | Cheng et al. |
| 2010/0173870 A1 | 7/2010 | Hostetler et al. |
| 2010/0273742 A1 | 10/2010 | Hostetler et al. |
| 2012/0058975 A1 | 3/2012 | Hostetler et al. |
| 2012/0116067 A1 | 5/2012 | Meier et al. |
| 2012/0122818 A1 | 5/2012 | Hostetler et al. |
| 2013/0029940 A1 | 1/2013 | Hostetler et al. |
| 2013/0045950 A1 | 2/2013 | Hostetler et al. |
| 2014/0045794 A1 | 2/2014 | Hostetler et al. |
| 2014/0274959 A1 | 9/2014 | Hostetler |
| 2014/0364397 A1 | 12/2014 | Hostetler et al. |
| 2015/0011488 A1 | 1/2015 | Preston et al. |
| 2015/0051174 A1 | 2/2015 | Hostetler et al. |
| 2015/0080344 A1 | 3/2015 | Hostetler et al. |
| 2016/0015726 A1 | 1/2016 | Hostetler et al. |
| 2017/0037068 A1 | 2/2017 | Hostetler et al. |
| 2017/0096441 A1 | 4/2017 | Hostetler et al. |

FOREIGN PATENT DOCUMENTS

| | | |
|---|---|---|
| CS | 263953 B1 | 5/1989 |
| CS | 263955 B1 | 5/1989 |
| CS | 263956 B1 | 5/1989 |
| CZ | 292199 | 8/2003 |
| EP | 0 262 876 A2 | 9/1987 |
| RU | 2187509 C1 | 8/2002 |
| WO | WO-91/19726 A1 | 12/1991 |
| WO | WO-92/03462 A1 | 3/1992 |
| WO | WO-92/07065 A1 | 4/1992 |
| WO | WO-93/15187 A1 | 8/1993 |
| WO | WO-93/19075 A1 | 9/1993 |
| WO | WO-95/32984 A1 | 12/1995 |
| WO | WO-96/05309 A2 | 2/1996 |
| WO | WO-96/39831 A1 | 12/1996 |
| WO | WO-98/38202 A1 | 9/1998 |
| WO | WO-98/42351 A1 | 10/1998 |
| WO | WO-99/62921 A1 | 12/1999 |
| WO | WO-00/29414 A1 | 5/2000 |
| WO | WO-01/39724 A2 | 6/2001 |
| WO | WO-01/64693 A1 | 9/2001 |
| WO | WO-02/057288 A1 | 7/2002 |
| WO | WO-02/087465 A2 | 11/2002 |
| WO | WO-02/087465 A3 | 11/2002 |
| WO | WO-03/002580 A1 | 1/2003 |
| WO | WO-03/050129 A1 | 6/2003 |
| WO | WO-03/090690 A2 | 11/2003 |
| WO | WO-03/090690 A3 | 11/2003 |
| WO | WO-03/090691 A2 | 11/2003 |
| WO | WO-03/090691 A3 | 11/2003 |
| WO | WO-03/099294 A1 | 12/2003 |
| WO | WO-2004/096235 A2 | 11/2004 |
| WO | WO-2004/096286 A2 | 11/2004 |
| WO | WO-2004/096286 A3 | 11/2004 |
| WO | WO-2004/111064 A1 | 12/2004 |
| WO | WO-2005/066189 A1 | 7/2005 |
| WO | WO-2005/087788 A2 | 9/2005 |
| WO | WO-2006/066074 A2 | 6/2006 |
| WO | WO-2006/076015 A2 | 7/2006 |
| WO | WO-2006/114064 A2 | 11/2006 |
| WO | WO-2006/114065 A2 | 11/2006 |
| WO | WO-2007/002808 A1 | 1/2007 |
| WO | WO-2007/130783 A2 | 11/2007 |
| WO | WO-2008/104408 A2 | 9/2008 |
| WO | WO-2008/104408 A3 | 9/2008 |
| WO | WO-2008/133966 A1 | 11/2008 |
| WO | WO-2009/094190 A2 | 7/2009 |
| WO | WO-2010/091386 A2 | 8/2010 |
| WO | WO-2010/135520 A1 | 11/2010 |
| WO | WO-2011/011519 A1 | 1/2011 |
| WO | WO-2011/011710 A1 | 1/2011 |
| WO | WO-2011/017253 A1 | 2/2011 |
| WO | WO-2011/053812 A1 | 5/2011 |
| WO | WO-2011/130557 A2 | 10/2011 |
| WO | WO-2014/143643 A1 | 9/2014 |
| WO | WO-2016/044281 A1 | 3/2016 |
| WO | WO-2017/048956 A1 | 3/2017 |

OTHER PUBLICATIONS

Berge et al., "Pharmaceutical Salts", *Journal of Pharmaceutical Sciences*, 1977, 66:1-19.
Campagne et al., "Synthesis of Mixed Phosphonate Diester Analogues of Dipeptides using BOP or PyBOP Reagents", *Tetrahedron Letters*, 1993, 34(42):6743-6744.
El-Faham, A. & Alberico, F., "Peptide Coupling Reagents, More than a Letter Soup", *Chemical Reviews*, 2011, 111:6557-660
Fingl, E. & Woodbury, D.M., *The Pharmacological Basis of Therapeutics*, Fifth Edition, Chapter 1, Section 1, 1975, pp. 1-47.

(56) References Cited

OTHER PUBLICATIONS

Holy et al., "Structure-Antiviral Activity Relationship in the Series of Pyrimidine and Purine N-[2-(2-Phosphonomethyoxy)ethyl] Nucleotide Analogues. 1. Derivatives Substituted at the Carbon Atoms of the base" *J. Med. Chem.* (1999) 42(12):2064-2086.

Hostetler et al., "Enhanced antiproliferative effects of alkoxyalkyl esters of cidofovir in human cervical cancer cells in vitro" *Mol Cancer Ther* (2006) 51(1):156-158.

International Search Report and Written Opinion dated May 29, 2014 for International Application No. PCT/US2014/027005, 9 pages.

Iyer et al., "Phosphorothioate Di- and Trinucleotides as a Novel Class of Anti-Hepatitis B Virus Agents", *Antimicrobial Agents and Chemotherapy*, 2004, 48(6):2199-2205.

Jansa et al., "Microwave-assisted hydrolysis of phosphonate diesters: an efficient protocol for the preparation of phosphonic acids" *Green Chem.* (2012) 14:2282-88.

Jindrich et al., "Synthesis of N-(3-Fluoro-2-Phosphonomethoxypropyl) (FPMP) Derivatives of Heterocyclic Bases", *Collect. Czech. Chem. Commun.*, 1993, 58:1645-1667.

Korba, B.E. & Gerin J.L., "Use of standardized cell culture assay to assess activities of nucleoside analogs against hepatitis B virus replication", *Antiviral Research*, 1992, 19:55-70.

Okuse et al., "Enhancement of antiviral activity against hepatitis C virus in vitro by interferon combination therapy", *Antiviral Research*, 2005, 65:23-34.

Painter et al., "Evaluation of Hexadecyloxypropyl-9-R-[2-(Phosphomethoxy)Proply]-Adenine, CMX157, as a Potential Treatment for Human Immunodeficiency Virus Type 1 and Hepatitis B Virus Infections," *Antimicrobial Agents and Chemotherapy*, 2007, 51:3505-3509.

Sells et al., "Replicative Intermediates of Hepatitis B Virus in HepG2 Cells That Produce Infectious Virions", *Journal of Virology*, 1988, 62(8):2836-2844.

Trahan et al., "Antiproliferative Effects of Octadecyloxyethyl-Phosphonomethoxyethylguanine (ODE-PMEG) on the Growth of Human Papilloma Virus Positive Cervical Carcinoma (ME-180) Cells in Vitro and Solid Tumors in Athymic Nude Mice" Abstract 85 *Antiviral Research* (2009) 82(2):A42.

Valiaeva et al., "Synthesis and antiviral evaluation of alkoxyalkyl esters of acyclic purine and pyrimidine nucleoside phosphonates against HIV-1 in vitro", *Antiviral Research*, 2006, 72:10-19.

Valiaeva et al., "Antiproliferative Effects of Octadecyloxyethyl 9-[2-(Phosphonomethoxy)Ethyl] Guanine against ME-180 Human Cervical Cancer Cells in vitro and in vivo", *Chemotherapy*, 2010, 56(1):54-59.

Valiaeva et al. "Synthesis and antiviral evaluation of 9-(S)-[3-alkoxy-2-(phosphonomethoxy)-proply] nucleoside alkoxyalkyl esters: Inhibitors of hepatitis C virus and HIV-1 replication", *Bioorganic & Medicinal Chemistry*, 2011, 19:4616-4625.

Vrbková et al., "Synthesis of phosphonomethyoxyethyl or 1,3-bis(phosphonomethyoxy)propan-2-yl lipophilic esters of acyclic nucleoside phosphonates" *Tetrahedron* (2007) 63:11391-11398.

Watson et al., "Comparative Evaluation of Virus Transmission Inhibition by Dual-Acting Pyrimidinedione Microbicides Using the Microbicide Transmission and Sterilization Assay", *Antimicrobial Agents Chemotherapy*, 2008, 52(8):2787-2796.

Webb, R. R., "The Bis-Trityl Route to (S)-HPMPA", *Nucleosides & Nucleotides*, 1989, 8(4):619-624.

Alexander et al., J. Med. Chem. 46, 4205-4208, 2003.

American Chemical Society. STN Database. RN 123156-16-1, Oct. 13, 1989.

American Chemical Society. STN Database. RN 123155-83-9, Oct. 13, 1989.

American Chemical Society. STN Database. RN 183107-05-3, Nov. 14, 1996, 1 page.

American Chemical Society. STN Database. RN 278611-52-2, Jul. 19, 2000, 1 page.

American Chemical Society. STN Database. RN 1022982-83-7, May 27, 2008, 1 page.

American Chemical Society. STN Database. RN 913356-63-5, Nov. 16, 2006, 1 page.

American Chemical Society. STN Database. RN 1204478-93-2, Feb. 3, 2010, 1 page.

American Chemical Society. STN Database. RN 1204478-95-4, Feb. 3, 2010, 1 page.

Analog, (2017). Located at <http://medical-dictionary.thefreedictionary.com/purine+Fanalogue>, last visited Feb. 27, 2017, 2 pages.

Balzarini, J., et al. "9-[(2R5)-3-Fluoro-2-phosphonylmethoxpropyl] derivatives of purines: A class of highly selective antiretroviral agents in vitro and in vivo." Proc. Natl. Acad. Sci. (1991), vol. 88, pp. 4961-4965.

Baker et al., Antiviral Res. 57: 13-23, 2003.

Beadle, J.R. et al. (Aug. 2002). "Alkoxplkyl esters of cidofovir and cyclic cidofovir exhibit multiple-log enhancement of antiviral activity against cytomegalovirus and herpesvirus replication in vitro," Antimicrob Agents Chemother 46(8):2381-2386.

Benzaria, S. et al. (Dec. 6, 1996). "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability.," J. Med. Chem. 39(25):4958-4965.

Bronson et al., J. Med. Chem., 1989, 32, p. 1457-1463.

Bronson et al., Nucleotide Analogues as Antiviral Agents, Chapter 5, p. 72-87, ACS Symposium Series, 1989, vol. 401.

Buchwald et al. (1980). Surgery 88:507-516.

Buller et al. (2004). Virology, 318:474-481.

CAS RN:278611-19-1, Registry. Jul. 19, 2000, 1 page.

CAS RN:278611-52-2, Registry. Jul. 19, 2000, 1 page.

Chand, P., Expert Opinion on Therapeutic Patents, 15 (8):1009-1025, 2005.

Cundy, K.C., Clinical Pharmacokinetics, 36:127-143, 1999.

De Clercq, Clinical Microbiology Reviews, 14:382-297, 2001.

Dietze, K., et al. "African Swine Fever (ASF) recent developments—timely updates." Empres Emergency Prevention System. 6(2012):1-6. Available at: < http://www.fao.org/docrep/016/ap372e/ap372e.pdf >.

Extended European Search Report dated Oct. 10, 2013 for European Application No. EP11769615.3, 13 pages.

FDA Guidance for Industry: Container Closure Systems for Packaging Human Drugs and Biologics (May 1999).

Heijtink, R.A. et al. (Sep. 1994). "Inhibitory effects of acyclic nucleoside phosphonates on human hepatitis B virus and duck hepatitis B virus infections in tissue culture," Antimicrob Agents Chemother 38(9):2180-2182.

Hostetler et al., Antiviral Research, 31:59-67, 1996.

Hostetler et al., "Alkoxyalkyl Esters of (S)-9-[3-Hydroxy-2-(Phosphonomethoxy)propyl]Adenine Are Potent Inhibitors of the Replication of Wild-Type and Drug-Resistant Human Immunodeficiency Virus Type 1 in Vitro", Antimicrobial Agents and Chemotherapy, American Society for Microbiology, 50(8):2857-2859 (2006).

Hostetler et al., Antiviral Research, 2007, 73(3), p. 212-218.

International Search Report dated Jul. 19, 2006 for International PCT Application No. PCT/US2005/045579, 4 pages.

International Preliminary Report on Patentability and Written Opinion dated Jun. 19, 2007 for International PCT Application No. PCT/US2005/045579, 8 pages.

International Preliminary Report on Patentability and Written Opinion dated Oct. 16, 2012 for International Application No. PCT/US2011/032558, 11 pages.

International Search report dated Jan. 18, 2012 for International Application No. PCT/US2011/032558, 5 pages.

International Search Report mailed on Dec. 4, 2015, for PCT Application No. PCT/US2015/050202, filed Sep. 15, 2015, 3 pages.

International Search Report mailed on Dec. 7, 2016, for PCT Application No. PCT/US2016/51942, filed Sep. 15, 2016, 4 pages.

Jansa, P. et al. (Sep. 2011, e-published May 23, 2011). "A novel and efficient one-pot synthesis of symmetrical diamide (bis-amidate) prodrugs of acyclic nucleoside phosphonates and evaluation of their biological activities," European Journal of Medicinal Chemistry, 46(9):3748-3754.

(56) References Cited

OTHER PUBLICATIONS

Keith et al., Antimicrobial Agents and Chemotherapy, 48:5, p. 1869-1871, May 2004.
Kern et al., "Enhanced Inhibition of Orthopoxvirus Replication in Vitro by Alkoxplkyl Esters of Cidofovir and Cyclic Cidofovir", Antimicrobial Agents and Chemotherapy, 46(4):991-995 (2002).
Kramata, P. et al. (Jun. 1996). "Different inhibitory potencies of acyclic phosphonomethoxyalkyl nucleotide analogs toward DNA polymerases alpha, delta and epsilon," Mol Pharmacol. 49(6):1005-1011.
Kramata, P. et al (Aug. 21, 1998). "Incorporation and excision of 9-(2-phosphonylmethoxyethyl)guanine (PMEG) by DNA polymerase delta and epsilon in vitro," 273(34):21966-21971.
Magee et al., "Mechanism of Inhibition of Vaccinia Virus DNA Polymerase by Cidofovir Diphosphate", Antimicrobial Agents and Chemotherapy, American Society for Microbiology, 49(8):3153-3162 (2005).
Maloisel et al., Antiviral Chemistry and Chemotherapy I, 10:333-345, 1999.
Mayo Clinic. "Smallpox." (Aug. 16, 2014). Located at: <http://www.mayoclinic.com/health/smallpox/DS00424/METHOD=print&DSECTION=all>, last visited, 4 pages.
McKimm-Breschkin et al. (2003). Angew Chem 115:3226-3229.
Meier, C. et al. (Dec. 15, 2005). cycloSal-PMEA and cycloAmb-PMEA: potentially new phosphonate prodrugs based on the cycloSal-pronucleotide approach, J. Med. Chem. 48(25):8079-8086.
Merta et al., "Phosphorylation of 9-(2-phosphonomethoxyethyl) adenine and 9-(S)-(3-hydroxy-2-phosphonomethoxpropyl)adenine by AMP (dAMP) kinase from L1210 cells", Biochemical Pharmacology, Elsevier, 44(10):2067-2077 (1992).
"Nucleotides, Nucleosides, and Nucleobases (Molecular Biology)." (2016). located at: <http://what-when-how.com/molecular-biology/nucleotides-nucleosides-and-nucleobases-molecular-biology>, last visited Dec. 30, 2016, 10 pages.
Pertusati, F. et al. "Medicinal chemistry of nucleoside phosphonate prodrugs for antiviral therapy." Antiviral Chemistry & Chemotherapy. (2012), vol. 22, pp. 181-203.
Pomeisl et al., "Pyrimidine Acyclic Nucleoside Phosphonates and Phosphorylated Analogs (Part 2): Syntheses and Investigation of Their Inhibitory Effects Towards Human Thymidine Phosphorylase", Nucleic Acids Symposium Series, 52(1): 657-658 (2008).
Pradere, U. et al. (Sep. 24, 2014, e-published Aug. 21, 2014). "Synthesis of Nucleoside and Phosphonate Prodrugs," Chemical Reviews 114(18):9154-9218.
Prichard et al., "Inhibition of Herpesvirus Replication by Hexadecyloxypropyl Esters of Purine- and Pyrimidine-Based Phosphonomethoxyethyl Nucleoside Phosphonates", Antimicrobial Agents and Chemotherapy, 52:4326-4330 (2008).
Puech, F. et al. (Oct. 1993). "Intracellular delivery of nucleoside monophosphates through a reductase-mediated activation process," Antiviral Research 22:155-174.
Quenelle, Antimicrobial Agents Chemotherapy, 48:404-412, 2004.
Reddy, K.R. et al. (Feb. 14, 2008, e-published Jan. 4, 2008). "Pradefovir: a prodrug that targets adefovir to the liver for the treatment of hepatitis B," J. Med. Chem. 51(3):666-676.
Saudek et al. (1989). N. Engl. J. Med. 321(9):574-579.
Sefton, M.V. (1987). CRC Crit. Ref. Biomed. Eng. 14(3):201-240.
Srivasta, D.N. et al. (1984). "Bioreversible Phosphate Protective Groups: Synthesis and Stability of Model Acyloxymethyl Phosphates," Bioorg. Chem 12:118-129.
Starrett, J.E. Jr. et al. (Jun. 10, 1994). "Synthesis, oral bioavailability determination, and in vitro evaluation of prodrugs of the antiviral agent 9-[2-(phosphonomethoxy)ethyl]adenine (PMEA).," J. Med. Chem. 37:1857-1864.

Tichý, T. et al. (Jun. 1, 2011, e-published Apr. 22, 2011). "New prodrugs of Adefovir and Cidofovir," Bioorg. & Med. Chem. 19(11):3527-3539.
Valiaeva Nadejda et al., "Antiviral evaluation of octadecyloxyethyl esters of (S)-3-hydroxy-2-(-(phosphonomethoxy)propyl nucleosides against herpesviruses and orthopoxviruses", Antiviral Research, 2009, vol. 84, pp. 254-259.
Wikipedia. "Progressive multifocal leukoencephalopathy." (2017). Located at: http://en.wikipedia.org/wiki/Progressive_multifocal_leukoencephalopathy#Treatment, last visited Feb. 27, 2017, 7 pages.
Written Opinion mailed on Dec. 4, 2015, for PCT Application No. PCT/US2015/050202, filed Sep. 15, 2015, 4 pages.
Written Opionion mailed on Dec. 7, 2016, for PCT Application No. PCT/US2016/51942, filed Sep. 15, 2016, 12 pages.
Wyles et al., "The Octadecyloxyethyl Ester of (S)-9-[3-Hydroxy-2-(Phosphonomethoxy)Propyl]Adenine Is a Potent and Selective Inhibitor of Hepatitus C Virus Replication in Genotype 1A, 1B, and 2A Replicons", Antimicrobial Agents and Chemotherapy, American Society for Microbiology, 53:2660-2662 (2009).
Yokota et al., "Inhibitory effects of acyclic nucleoside phosphonate analogs on hepatitis B virus DNA synthesis in HB611 cells", Antiviral Chemistry and Chemotherapy, 5(2):57-63 (1994).
Brown, N.A. (2009). "Progress towards improving antiviral therapy for hepatitis C with hepatitis C virus polymerase inhibitors. Part 1: Nucleoside analogues," *Expert Opinion on Investigational Drugs* 18(6):709-725.
Database Caplus [Online] Chemical Abstracts Service, Columbus, Ohio, US; Otmar, Miroslav et al: "An alternative synthesis of HPMPC and HPMPA diphosphoryl derivatives", retrieved from STN Database accession No. 2000:234286; & Otmar, Miroslav et al: "An alternative synthesis of HPMPC and HPMPA diphosphoryl derivatives", Collection Symposium Series, 2(Chemistry of Nucleic Acid Components), 252-254 CODEN: CSYSFN, 1999, 2 pages.
Database Caplus [Online] Chemical Abstracts Service, Columbus, Ohio, US; Votruba, Ivan et al: "Inhibition of human purine nucleoside phosphorylase by tenofovir phosphate congeners", retrieved from STN Database accession No. 2010:1628491; & Votruba, Ivan et al: "Inhibition of human purine nucleoside phosphorylase by tenofovir phosphate congeners", Collection of Czechoslovak Chemical Communications, 75(12), 1249-1257 CODEN: CCCAK; ISSN: 0010-0765, 2010, 1 page.
De Clercq, E. (2007). "Acyclic nucleoside phosphonates: Past, present and future Bridging chemistry to HIV, HBV, HCV, HPV, adeno-, herpes-, and poxvirus infections: The phosphonate bridge", *Biochemical Pharmacology*, 73:911-922.
Figlerowicz, M., et al. (2003). "Genetic Variability: The Key Problem in the Prevention and Therapy of RNA-Based Virus Infections." *Medicinal Research Reviews* 23(4):488-518.
Holy, A. (2006). "'Antiviral acyclic nucleoside phosphonates structure activity studies," *Antiviral Research* 71:248-253.
Huggins, J.W. et al., (2002). "Orally Active Ether Lipid Prodrugs of Cidofovir for the Treatment of Smallpox," *Antiviral Research*, 53:A66 (104).
Koh, Y-H. et al., (2005). "Design, Synthesis and Antiviral Activity of Adenosine 5'-Phosphonate Analogues as Chain Terminators against Hepatitis C Virus", *Journal of Medicinal Chemistry* 48(8):2867-2875.
Rosenberg, I. et al. (1988). "Phosphonylmethoxyalkyl and Phosphonylalkyl Derivatives of Adenine*," Collection Czechoslovak Chem. Commun., 53:2753-2777.
Sheng, X.C. et al. (2009). "Discovery of novel phosphonate derivatives as hepatitis C virus NS3 protease inhibitors", *Bioorganic & Medicinal Chemistry Letters* 19:3453-3457.
Tobias, S. C. et al.,(Mar-Apr 2004). "Synthesis and biological evaluation of a cytarabine phosphoramidate prodrug," Mol. Pharmaceutics 1(2):112-116.

* cited by examiner

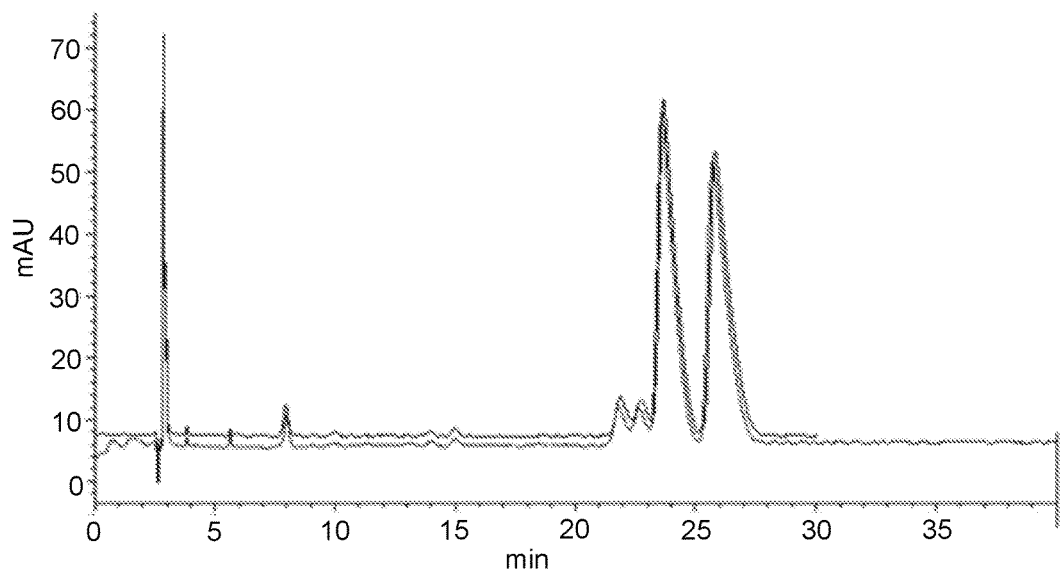

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 1
agtggatggg cagcctatgt a                                            21

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
tcatatctgg gtcccctgga                                              20

<210> SEQ ID NO 3
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (1)..(1)
<223> OTHER INFORMATION: 5' residues modified with 6-FAM
<220> FEATURE:
<221> NAME/KEY: misc_feature
<222> LOCATION: (33)..(33)
<223> OTHER INFORMATION: 3' residue modified with TAMRA

<400> SEQUENCE: 3
aggtagaaga ggttagggtg tttgatggca cag                            33

<210> SEQ ID NO 4
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 4
ctggtcatgt ggatgctgtc a                                         21

<210> SEQ ID NO 5
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 5
gccagcaggc tgttgatact g                                         21

<210> SEQ ID NO 6
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5' residue modified with 6-FAM
<220> FEATURE:
<221> NAME/KEY: misc_feature
<222> LOCATION: (17)..(17)
<223> OTHER INFORMATION: 3' residues modified with TAMRA

<400> SEQUENCE: 6
ccctttgttt ggctgct                                              17
```

ACYCLIC NUCLEOSIDE PHOSPHONATE DIESTERS

CROSS-REFERENCES TO RELATED APPLICATIONS

This application is a continuation of U.S. application Ser. No. 14/874,027, filed Oct. 2, 2015, which is a continuation of U.S. application Ser. No. 14/463,908, filed Aug. 20, 2014, and now issued as U.S. Pat. No. 9,156,867, which is a continuation U.S. application Ser. No. 14/211,235, filed Mar. 14, 2014, now issued as U.S. Pat. No. 8,835,630, which claims the benefit of U.S. Provisional Application No. 61/793,993, filed Mar. 15, 2013, the content of each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant numbers AI-071803, AI-074057 and EY07366 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 84537-532C03US_ST25.TXT, created Jun. 8, 2016, 1,997 bytes, machine format IBM-PC, MS-Windows operating system, is hereby incorporated by reference.

BACKGROUND

The present disclosure relates, inter alia, to compositions and methods for treating viral diseases and cancer. In one aspect it relates to lipophilic antiviral and anticancer acyclic nucleoside phosphonate diesters, preparation thereof, and methods of using the compounds to treat viral diseases and cancer.

Viruses are infectious particles that can replicate their DNA and RNA only within host cells. Viral infections may lead to mild or severe illnesses in humans and mammals. Examples of viral infections include hepatitis B and C, smallpox, herpes simplex, cytomegalovirus, human immunodeficiency virus (HIV), influenza, adenovirus, chickenpox, BK virus, JC virus and precancerous lesions caused by infections with the human papillomavirus (cervical intraepithelial neoplasia, vaginal and anal intraepithelial neoplasia). Viral infection may also lead to cancer in humans and other species. Viruses known to cause cancer include but are not limited to human papilloma virus (HPV), hepatitis B virus (HBV), hepatitis C virus (HCV), HIV and Epstein Barr virus (EBV). Vaccination has been successful in preventing infection from many viruses. Antiviral agents are known that interfere with viral DNA or RNA synthesis and viral replication and are used to prevent or treat viral infections in mammals and humans. For example, combinations of antiviral drugs are used to treat AIDS, hepatitis B, hepatitis C, herpes simplex viruses, cytomegalovirus and influenza. Despite these successes, viral diseases remain an important public health problem and improved antiviral agents and anticancer agents are needed. For example, there is presently no approved antiviral treatment for human papillomavirus infections.

Many antiviral drugs are nucleoside or nucleotide analogs. Examples of antiviral nucleoside analogs include azidothymidine, acyclovir, ganciclovir, lamivudine and emtricitabine. Acyclic nucleoside phosphonates (ANPs) are a class of nucleotide analogs and are effective antiviral agents. Adefovir, tenofovir and cidofovir (CDV) are ANPs that have been approved for clinical use against human infections with HBV, HIV and CMV, respectively.

ANPs are known in the art not to be absorbed readily from the gastrointestinal tract of mammals because of their molecular weight and the presence of the double negative charge on the phosphonate. Because of their poor oral pharmacokinetic properties, ANPs are usually converted to prodrugs to produce clinically useful therapeutic agents. It has been demonstrated that masking one or both negative charges with promoieties improves the uptake and transport into the small intestinal enterocytes where the promoiety is cleaved, releasing the ANP into the circulation; examples include tenofovir disoproxil fumarate and adefovir dipivoxil. Another approach is to prepare alkoxyalkyl or alkyl monoesters of ANPs to increase oral bioavailability of the drug. With the alkoxyalkyl ANP monoester approach, side effects may occur when non-targeted tissues such as the small intestine are overexposed. For example, in enterocytes, enzymatic cleavage of the promoiety by a phospholipase C or an acid sphingomyelinase to the ANP may result in local toxicity because of further anabolic phosphorylation to the ANP diphosphate which may inhibit enterocyte DNA synthesis. Lipophilic ANP diester compounds are anticipated to undergo less cleavage from intact prodrug to ANP in the small intestine enterocytes following oral administration reducing GI side effects and releasing more drug substance into the circulation and producing higher levels of the drug substance in the blood.

ANPs or their alkyl or alkoxyalkyl monoesters may exhibit limited uptake in certain target tissues such as the central nervous system. An additional advantage of nucleoside phosphonate diesters is the masking of the remaining negative charge on the phosphonate oxygen with a second masking group which can increase penetration of the drug substance into the central nervous system (CNS) for treatment of CNS viral infections (for example, HIV or JC virus) or for treatment of brain cancers such as glioblastoma. Cancer cells rapidly synthesize DNA and undergo uncontrolled cell division. The lipophilic acyclic nucleoside phosphonate (ANP) diester compositions described herein can be metabolized to their diphosphates which inhibit or block DNA synthesis and cell division in target cancer cells, leading to cell death while having substantially lesser effects on non-malignant cells. Exposure of various types of cancer cells to acyclic nucleoside phosphonates diesters may result in much greater cytotoxicity than that observed in normal non-malignant cells. For example, leukemias, lymphomas, brain neoplasms such as glioblastoma and cervical cancer cells may be more susceptible to the cytotoxic effects when exposed to lipophilic ANP diesters than the corresponding non-malignant cell lines. Lipophilic acyclic nucleoside phosphonate diesters exhibit more selective toxicity, improved access to the central nervous system and effective topical uptake for treatment of skin cancers, viral skin infections, cervical intraepithelial neoplasia (CIN), vaginal and anal intraepithelial dysplasia, venereal warts and related infections caused by the human papillomavirus when compared to acyclic nucleoside phosphonate monoester compositions.

Compounds disclosed herein having both ANP phosphonate negative charges masked with functional groups provide for more effective use as topical agents for treatment of skin cancers and viral infections. In particular, compounds disclosed herein provide for efficacious treatment for infections of the cervical, vaginal, rectal and penile epithelium with the human papilloma virus including the high risk subtypes such as 16, 18, 31, 33, 35, 39, 45, 51, 52, 56, 58, 59, 68, 73, and 82 which are associated with cervical, rectal, penile and vaginal cancer and venereal warts.

BRIEF SUMMARY

In a first aspect, there is provided a compound with structure of Formula (I),

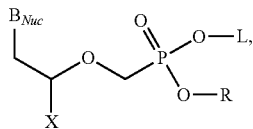

or stereoisomer, salt, hydrate, solvate, or crystalline form thereof. Regarding Formula (I), L is a lipophilic promoiety, substituted or unsubstituted alkyl, substituted or unsubstituted heteroalkyl, or O-substituted glyceryl having the formula —$CH_2CH(OR^1)$—$CH_2(OR^2)$ (II), wherein $R^1$ and $R^2$ are independently substituted or unsubstituted alkyl or substituted or unsubstituted aryl. R is substituted or unsubstituted lower alkyl, substituted or unsubstituted lower heteroalkyl, substituted or unsubstituted lower cycloalkyl, substituted or unsubstituted lower heterocycloalkyl, substituted or unsubstituted aryl, or substituted or unsubstituted lower heteroaryl. X is hydrogen, substituted or unsubstituted lower alkyl, or substituted or unsubstituted lower heteroalkyl.

In another aspect, there is provided a method of treating a viral disease in a subject, including administering to a subject in need thereof a therapeutically effective amount of a compound of Formula (I).

In another aspect, there is provided a method for treating cancer in a subject, including administering to a subject in need thereof a therapeutically effective amount of a compound of Formula (I).

In another aspect, there is provided a method for killing or inhibiting the growth of a transformed cell, including contacting a transformed cell with a therapeutically effective amount of a compound of Formula (I).

In another aspect, there is provided a method for treating a proliferative disorder in a subject, including administering to a subject in need thereof a therapeutically effective amount of a compound of Formula (I).

In another aspect, there is provided a pharmaceutical composition which includes a compound according to Formula (I), and a pharmaceutically acceptable excipient.

In another aspect, there is provided a method for synthesis of a compound with structure of Formula (I) according to Scheme 2 disclosed herein. The method includes contacting a protected nucleoside $B_{Nuc}$ with structure of Formula (2-1) with an ester with structure of Formula (2-2) in the presence of a strong base under conditions suitable to afford a monoester with structure of Formula (2-3); and reacting the afforded monoester with L-OH in the presence of a coupling agent, thereby synthesizing a compound with structure of Formula (I).

In another aspect, there is provided a compound of Formula (Ia), or a pharmaceutically acceptable salt, hydrate, solvate or crystalline form thereof:

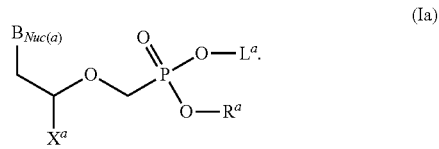

For Formula (Ia), $B_{Nuc(a)}$ can be a naturally occurring purine, a naturally occurring pyrimidine, a non-naturally occurring purine or a non-naturally occurring pyrimidine; $L^a$ can be an unsubstituted $C_{12-24}$ alkyl, an unsubstituted $C_{13-29}$ heteroalkyl or a substituted glyceryl moiety, wherein the glyceryl moiety can be substituted with one or more groups selected from an unsubstituted $C_{13-29}$ alkyl, an unsubstituted $C_{13-29}$ heteroalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); $R^a$ can be selected from an unsubstituted $C_{1-6}$ alkyl, a substituted or unsubstituted aryl, a substituted or unsubstituted heteroaryl, a substituted or unsubstituted heterocycloalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); and $X^a$ can be hydrogen, an unsubstituted $C_{1-6}$ alkyl, a halogen substituted $C_{1-6}$ alkyl, a hydroxy substituted $C_{1-6}$ alkyl or an unsubstituted $C_{1-6}$ alkoxy.

In another aspect, there is provided a pharmaceutical composition that can include an effective amount of a compound as disclosed herein (for example, a compound of Formula (Ia)), or a pharmaceutically acceptable salt, hydrate, solvate or crystalline form thereof, and a pharmaceutically acceptable excipient.

In another aspect, there is provided a compound as disclosed herein (for example, a compound of Formula (Ia)), or a pharmaceutically acceptable salt, hydrate, solvate or crystalline form thereof, for use in treating a viral disease in a subject, wherein the viral disease can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In another aspect, there is provided a compound as disclosed herein (for example, a compound of Formula (Ia)), or a pharmaceutically acceptable salt, hydrate, solvate or crystalline form thereof, for use in treating cancer of the cervix in a subject.

In another aspect, there is provided a compound as disclosed herein, or a pharmaceutically acceptable salt, hydrate, solvate or crystalline form thereof, for use in inhibiting growth of a cell transformed by a virus, wherein the virus can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In another aspect, there is provided a compound as disclosed herein (for example, a compound of Formula (Ia)), or a pharmaceutically acceptable salt, hydrate, solvate or crystalline form thereof, in the preparation of a medicament for treating a viral disease in a subject, wherein the viral disease can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In another aspect, there is provided use of a compound as disclosed herein (for example, a compound of Formula (Ia)), or a pharmaceutically acceptable salt, hydrate, solvate or crystalline form thereof, in the preparation of a medicament for treating cancer of the cervix in a subject.

In another aspect, there is provided use of a compound as disclosed herein (for example, a compound of Formula (Ia)), or a pharmaceutically acceptable salt, hydrate, solvate or crystalline form thereof, in the preparation of a medicament for inhibiting growth of a cell transformed by a virus, wherein the virus can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In another aspect, there is provided a method of synthesis of a compound with structure of Formula (Ia).

BRIEF DESCRIPTION OF THE DRAWINGS

The FIGURE provides a chromatogram of compound 1a (fast-eluting) and compound 1b (slow eluting), as described in Example 2. X-axis: time (min); Y-axis (milli-absorption units, mAu). Solvent: 50:50:0.1 Water:Acetonitrile:TFA.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

As used herein, the term "alkyl," by itself or as part of another substituent, means, unless otherwise stated, and includes a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like.

An unsaturated alkyl group is one having one or more double bonds (an "alkenyl group") or triple bonds (an "alkynyl group"). Examples of unsaturated alkyl groups include, but are not limited to, the alkenyl groups vinyl, 2-propenyl, crotyl, 2-isopentenyl, 2-(butadienyl), 2,4-pentadienyl, 3-(1,4-pentadienyl), and the alkynyl groups ethynyl, 1- and 3-propynyl, 3-butynyl, and the higher homologs and isomers.

An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, or 10 or fewer carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N(CH_3)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, —CH=CH—N(CH_3)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—.

As described above, heteroalkyl groups, as used herein, include those groups that are attached to the remainder of the molecule through a heteroatom, such as —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R* where R* is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" [e.g., aryl($C_{1-6}$ alkyl)] is meant to include those radicals in which an aryl group is attached to an alkyl group (e.g., benzyl (Bn), phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Thus, the term "heteroarylalkyl" [e.g., heteroaryl($C_{1-6}$ alkyl)] refers to those radicals in which a heteroaryl group is attached to an alkyl group. The term "heterocycloalkylalkyl" [e.g., heterocycloalkyl($C_{1-6}$ alkyl)] refers to those radicals in which a heterocycloalkyl is attached to an alkyl group.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NR$SO_2$R', —CN, and —$NO_2$ in a number ranging from zero to (2m'+1), where m' is the total number of carbon atoms in such radical. R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "substituted alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NR$SO_2$R', —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{29}$ alkyl, each substituted or unsubstituted heteroalkyl is a substituted or unsubstituted 2 to 30 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, in embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In embodiments, at least one or all of these groups are substituted with at least one size-limited substituent group. In embodiments, at least one or all of these groups are substituted with at least one lower substituent group.

In embodiments of the compounds herein, each substituted or unsubstituted alkyl may be a substituted or unsubstituted $C_1$-$C_{30}$ alkyl, each substituted or unsubstituted heteroalkyl is a substituted or unsubstituted 2 to 30 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted $C_1$-$C_{30}$ alkylene, each substituted or unsubstituted heteroalkylene is a substituted or unsubstituted 2 to 30 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

The term "pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66:1-19). Certain specific compounds described herein contain both basic and acidic functionalities that allow the compounds to be converted into either base or acid addition salts.

Thus, the compounds described herein [for example, a compound of Formula (I) and/or a compound of Formula (Ia)] may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds can be regenerated by contacting the salt with a base or acid and isolating the parent compound in the conventional manner. The parent form of the compound differs from the various salt forms in certain physical properties, such as solubility in polar solvents.

In addition to salt forms, compounds described herein [for example, a compound of Formula (I) and/or a compound of Formula (Ia)] can be in a prodrug form. Prodrugs of the compounds described herein are those compounds that readily undergo chemical changes under physiological conditions to provide a compound described herein. Additionally, prodrugs can be converted to a compounds described herein by chemical or biochemical methods in an ex vivo environment. For example, prodrugs can be slowly converted to a compounds described herein when placed in a transdermal patch reservoir with a suitable enzyme or chemical reagent. The term "promoiety" is meant to refer to a chemical entity reversibly attached to the drug that improves an aspect of drug performance by masking a problematic functional group.

Certain compounds described herein [for example, a compound of Formula (I) and/or a compound of Formula (Ia)] can exist in unsolvated forms as well as solvated forms, including hydrated forms. In general, the solvated forms are equivalent to unsolvated forms and are encompassed. Certain compounds described herein [for example, a compound of Formula (I) and/or a compound of Formula (Ia)] may exist in multiple crystalline or amorphous forms. In general, all physical forms are equivalent for the uses contemplated and are intended.

Certain compounds described herein [for example, a compound of Formula (I) and/or a compound of Formula (Ia)] can possess asymmetric atoms (optical centers) or double bonds; the racemates, diastereomers, tautomers, geometric isomers, and individual isomers are encompassed. The compounds described herein [for example, a compound of Formula (I) and/or a compound of Formula (Ia)] do not include those that are known in the art to be too unstable to synthesize and/or isolate.

The compounds described herein [for example, a compound of Formula (I) and/or a compound of Formula (Ia)] may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds, whether radioactive or not, are encompassed.

The symbol " $\sim\!\sim$ " denotes the point of attachment of a chemical moiety to the remainder of a molecule or chemical formula.

II. Compounds

In a first aspect, there is provided a compound with structure of Formula (I):

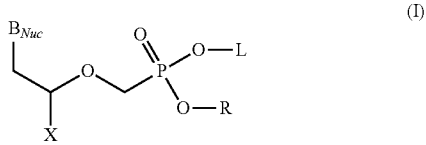

(I)

or stereoisomer, salt, hydrate, solvate, or crystalline form thereof. For the compound with structure of Formula (I), $B_{Nuc}$ is a naturally occurring purine or pyrimidine base, or analog thereof; L is a lipophilic promoiety, substituted or unsubstituted alkyl, substituted or unsubstituted heteroalkyl, or O-substituted glyceryl having the formula —CH$_2$CH(OR$^1$)—CH$_2$(OR$^2$) (II), wherein R$^1$ and R$^2$ are independently substituted or unsubstituted alkyl, or substituted or unsubstituted aryl; R is substituted or unsubstituted lower alkyl, substituted or unsubstituted lower heteroalkyl, substituted or unsubstituted lower cycloalkyl, substituted or unsubstituted lower heterocycloalkyl, substituted or unsubstituted aryl, or substituted or unsubstituted lower heteroaryl; and X is hydrogen, substituted or unsubstituted lower alkyl, or substituted or unsubstituted lower heteroalkyl.

In embodiments, the compound is a stereoisomer with the structure of Formula (I). In embodiments, the compound is a salt of a compound with the structure of Formula (I). In embodiments, the compound is a solvate of a compound with the structure of Formula (I). In embodiments, the compound is a crystalline form of a compound with the structure of Formula (I).

The terms "naturally occurring purine or pyrimidine base" and the like refer, in the usual and customary sense as employed in the art, to purine or pyrimidine bases, e.g., guanine, adenine, cytosine, thymine, uracil, or 2,6-diaminopurine. Attachment of the naturally occurring purine or pyrimidine base can be at any available site, e.g., guanin-9-yl, adenine-9-yl, cytosine-1-yl, thymin-1-yl, uracil-1-yl, 2,6-diaminopurin-9-yl, and the like. When attached to the remainder of the compounds described herein, the naturally occurring purine or pyrimidine base is in monovalent from (the form of a chemical moiety or substituent as known in the art).

The terms "analog of naturally occurring purine or pyrimidine base" and the like refer, in the usual and customary sense, to a chemical analog of a naturally occurring purine or pyrimidine base, as known in the art. When attached to the remainder of the compounds described herein, the analog of naturally occurring purine or pyrimidine base is in monovalent from (the form of a chemical moiety or substituent as known in the art).

Accordingly, in embodiments, $B_{Nuc}$ is a naturally occurring purine or pyrimidine base. In embodiments, $B_{Nuc}$ is a naturally occurring purine base. In embodiments, $B_{Nuc}$ is a naturally occurring pyrimidine base. In embodiments, $B_{Nuc}$ is an analog of a naturally occurring purine or pyrimidine base. In embodiments, $B_{Nuc}$ is an analog of a naturally occurring base. In embodiments, $B_{Nuc}$ is an analog of a naturally occurring pyrimidine base.

The terms "lipophilic promoiety" and the like refer to a chemical moiety which imparts increased lipophilicity when incorporated into a compound with structure of Formula (I). In embodiments, the lipophilic promoiety is a substituted or unsubstituted $C_{8-24}$ alkyl. In embodiments, the lipophilic promoiety is a substituted or unsubstituted $C_{8-24}$ heteroalkyl. In embodiments, the lipophilic promoiety is a substituted or unsubstituted $C_{8-24}$ alkoxyalkyl. Exemplary lipophilic promoieties include glyceryl moieties having substituted or unsubstituted alkyl, and/or substituted or unsubstituted aryl substituents. In embodiments, substitution at a glyceryl moiety is via O-substitution with a substituted or unsubstituted alkyl, and/or via O-substitution with a substituted or unsubstituted aryl. Thus, the lipophilic promoiety, L, imparts lipophilicity and therefore may include glyceryl ether linked compounds (e.g., 1-O-octadecyl-2-O-benzyl) wherein the hydrogens of the glyceryl hydroxyls are replaced with substituted or unsubstituted alkyl or substituted or unsubstituted aryl groups that do not impart hydrophilicity, and the carbons atoms of the glyceryl are not further substituted. In some embodiments, L is an O-substituted glyceryl having the formula —CH$_2$CH(OR$^1$)—CH$_2$(OR$^2$) (II), wherein R$^1$ and R$^2$ are independently a substituted or unsubstituted alkyl or a substituted or unsubstituted aryl.

In some embodiments, L is a substituted or unsubstituted alkyl, substituted or unsubstituted heteroalkyl, or an O-substituted glyceryl having the formula —CH$_2$CH(OR$^1$)—CH$_2$(OR$^2$) (II), wherein R$^1$ and R$^2$ are independently a substituted or unsubstituted alkyl or a substituted or unsubstituted aryl. In embodiments, L is an O-substituted glyceryl. In one embodiment L is 1-O-alkyl-2-O-benzyl-sn-glyceryl. In embodiments, L is 1-O-octadecyl-2-O-benzyl-sn-glyceryl. In embodiments, L is an unsubstituted alkyl. In embodiments, L is a size-limited unsubstituted alkyl. In embodiments, L is $C_{8-24}$ alkyl. In embodiments, L is an unsubstituted heteroalkyl. In embodiments, L is a size-limited unsubstituted heteroalkyl. In embodiments, L is $C_{8-24}$ heteroalkyl. In embodiments, L is an unsubstituted alkoxyalkyl. In embodiments, L is a size-limited unsubstituted alkoxyalkyl. In embodiments, L is $C_{8-24}$ alkoxyalkyl.

In embodiments, R is a substituted or unsubstituted lower alkyl, a substituted or unsubstituted lower heteroalkyl, a substituted or unsubstituted lower cycloalkyl, a substituted or unsubstituted lower heterocycloalkyl, a substituted or unsubstituted aryl, or a substituted or unsubstituted lower heteroaryl. In embodiments, R is a substituted or unsubstituted lower alkyl. In embodiments, R is a substituted or unsubstituted lower heteroalkyl. In embodiments, R is an O-substituted glyceryl having the formula —CH$_2$CH(OR$^3$)—CH$_2$(OR$^4$) (III), wherein R$^3$ and R$^4$ are independently a substituted or unsubstituted alkyl or a substituted or unsubstituted aryl. In embodiments, R is a substituted or unsubstituted lower cycloalkyl. In embodiments, R is a substituted or unsubstituted lower heterocycloalkyl. In embodiments, R is a substituted or unsubstituted hexopyranosyl. In embodiments, R is an unsubstituted hexopyranosyl. In embodiments, R is a substituted or unsubstituted aryl. In embodiments, R is a substituted or unsubstituted lower heteroaryl. In embodiments, R is an unsubstituted lower alkyl. In embodiments, R is an unsubstituted lower heteroalkyl. In embodiments, R is an unsubstituted lower cycloalkyl. In embodiments, R is an unsubstituted lower heterocycloalkyl. In embodiments, R is an unsubstituted aryl. In embodiments, R is an unsubstituted lower heteroaryl. In embodiments, R is a size-limited substituted or unsubstituted lower cycloalkyl. In embodiments, R is a size-limited substituted or unsubstituted lower heterocycloalkyl. In embodiments, R is a size-limited substituted or unsubstituted aryl. In embodiments, R is a size-limited substituted or unsubstituted lower heteroaryl. In embodiments, R is $C_{1-8}$ substituted or unsubstituted alkyl. In embodiments, R is $C_{1-8}$ substituted or unsubstituted heteroalkyl. In embodiments, R is $C_{4-8}$ substituted or unsubstituted cycloalkyl. In embodiments, R is $C_{4-8}$ substituted or unsubstituted heterocycloalkyl. In embodiments, R is C<sub>6-10</sub> substituted or unsubstituted aryl. In embodiments, R is C<sub>6-10</sub> substituted or unsubstituted heteroaryl. In embodiments, R is $C_{1-8}$ unsubstituted alkyl. In embodiments, R is $C_{2-8}$ unsubstituted heteroalkyl. In embodiments, R is $C_{4-8}$ unsubstituted cycloalkyl. In embodiments, R is $C_{4-8}$ unsubstituted heterocycloalkyl. In embodiments, R is $C_{6-10}$ unsubstituted aryl. In embodiments, R is $C_{6-10}$ unsubstituted heteroaryl.

In embodiments, R is a substituted or unsubstituted phenyl, a substituted or unsubstituted naphthyl, a substituted or unsubstituted benzyl, a substituted or unsubstituted glyceryl, or a substituted or unsubstituted hexopyranosyl. In embodiments, R is a substituted phenyl. In embodiments, R is a substituted naphthyl. In embodiments, R is a substituted benzyl. In embodiments, R is a substituted glyceryl. In embodiments, R is a substituted hexopyranosyl. In embodiments, R is an unsubstituted phenyl. In embodiments, R is an unsubstituted naphthyl. In embodiments, R is an unsubstituted benzyl. In embodiments, R is an unsubstituted glyceryl. In embodiments, R is an unsubstituted hexopyranosyl.

In embodiments, X is hydrogen, a substituted or unsubstituted lower alkyl, or a substituted or unsubstituted lower heteroalkyl. In embodiments, X is hydrogen. In embodiments, X is a substituted or unsubstituted lower alkyl. In embodiments, X is a substituted or unsubstituted lower heteroalkyl. In embodiments, X is an unsubstituted lower alkyl. In embodiments, X is an unsubstituted lower heteroalkyl. In embodiments, X is a size-limited substituted or unsubstituted alkyl. In embodiments, X is a size-limited substituted or unsubstituted heteroalkyl. In embodiments, X is a size-limited unsubstituted alkyl. In embodiments, X is a size-limited unsubstituted heteroalkyl. In embodiments, X is methyl. In embodiments, X is methoxymethyl. In embodiments, X is hydroxymethyl. In embodiments, X is fluoromethyl.

In embodiments, the compound with structure of Formula (I) has the structure of Formula (I-1):

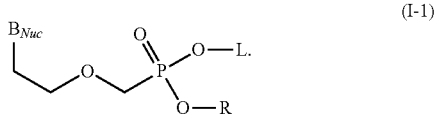

(I-1)

For the compound with structure of Formula (I-1), $B_{Nuc}$ is as described for any of the embodiments of the compound of Formula (I) disclosed herein.

In embodiments, L is as described for any of the embodiments of the compound of Formula (I) described herein. In embodiments, L is octadecyloxyethyl, hexadecyloxypropyl, or 1-O-octadecyl-2-O-benzyl-sn-glyceryl. In embodiments, L is octadecyloxyethyl. In embodiments, L is hexadecyloxypropyl. In embodiments, L is 1-O-octadecyl-2-O-benzyl-sn-glyceryl.

In embodiments, R is as described for any of the embodiments of the compound of Formula (I) described herein. In embodiments, R is a substituted or unsubstituted phenyl, a substituted or unsubstituted naphthyl, a substituted or unsubstituted benzyl, a substituted or unsubstituted glyceryl, or a substituted or unsubstituted hexopyranosyl. In embodiments, R is a substituted phenyl. In embodiments, R is a substituted naphthyl. In embodiments, R is a substituted benzyl. In embodiments, R is a substituted glyceryl. In embodiments, R is a substituted hexopyranosyl. In embodiments, R is an unsubstituted phenyl. In embodiments, R is an unsubstituted naphthyl. In embodiments, R is an unsubstituted benzyl. In embodiments, R is an unsubstituted glyceryl. In embodiments, R is an unsubstituted hexopyranosyl.

In embodiments, the compound with structure of Formula (I) has the structure of Formula (I-2):

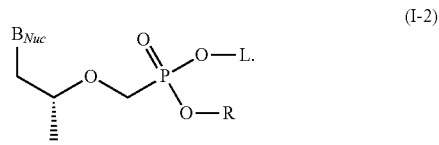

(I-2)

For the compound with structure of Formula (I-2), in one embodiment $B_{Nuc}$ is as described for any of the embodiments of the compound of Formulae (I)-(I-1) disclosed herein.

In embodiments, L is as described for any of the embodiments of the compound of Formulae (I)-(I-1) described herein.

In embodiments, R is as described for any of the embodiments of the compound of Formulae (I)-(I-1) described herein.

In embodiments, the compound with structure of Formula (I) has the structure of Formula (I-3):

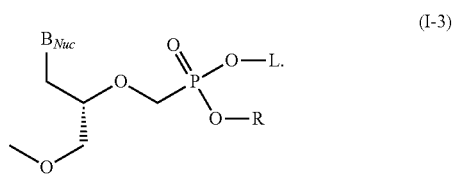

(I-3)

For the compound with structure of Formula (I-3), in one embodiment $B_{Nuc}$ is as described for any of the embodiments of the compound of Formulae (I)-(I-2) disclosed herein.

In embodiments, L is as described for any of the embodiments of the compound of Formulae (I)-(I-2) described herein.

In embodiments, R is as described for any of the embodiments of the compound of Formulae (I)-(I-2) described herein.

In embodiments, the compound with structure of Formula (I) has the structure of Formula (I-4):

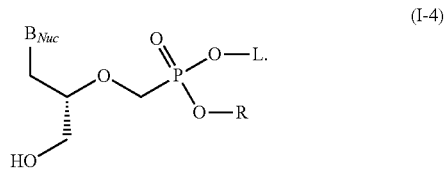

(I-4)

For the compound with structure of Formula (I-4), in one embodiment $B_{Nuc}$ is as described for any of the embodiments of the compound of Formulae (I)-(I-3) disclosed herein.

In embodiments, L is as described for any of the embodiments of the compound of Formulae (I)-(I-3) described herein.

In embodiments, R is as described for any of the embodiments of the compound of Formulae (I)-(I-3) described herein.

In embodiments, the compound with structure of Formula (I) has the structure of Formula (I-5):

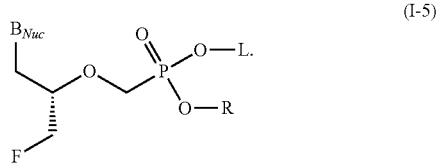

(I-5)

For the compound with structure of Formula (I-5), in one embodiment $B_{Nuc}$ is as described for any of the embodiments of the compound of Formulae (I)-(I-4) disclosed herein.

In embodiments, L is as described for any of the embodiments of the compound of Formulae (I)-(I-4) described herein.

In embodiments, R is as described for any of the embodiments of the compound of Formulae (I)-(I-4) described herein.

In another aspect, there is provided a compound of Formula (Ia), or a pharmaceutically acceptable salt, hydrate, solvate or crystalline form thereof:

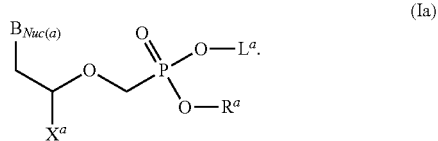

(Ia)

For this aspect, $B_{Nuc(a)}$ can be a naturally occurring purine, a naturally occurring pyrimidine, a non-naturally occurring purine or a non-naturally occurring pyrimidine. $L^a$ can be an unsubstituted $C_{12-24}$ alkyl, an unsubstituted $C_{13-29}$ heteroalkyl or a substituted glyceryl moiety. The glyceryl moiety may be substituted with one or more groups selected from an unsubstituted $C_{13-29}$ alkyl, an unsubstituted $C_{13-29}$ heteroalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl). $R^a$ can be selected from an unsubstituted $C_{1-6}$ alkyl, a substituted or unsubstituted aryl, a substituted or unsubstituted heteroaryl, a substituted or unsubstituted heterocycloalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl). $X^a$ can be hydrogen, an unsubstituted $C_{1-6}$ alkyl, a halogen substituted $C_{1-6}$ alkyl, a hydroxy substituted $C_{1-6}$ alkyl or an unsubstituted $C_{1-6}$ alkoxy.

In embodiments, $X^a$ can be hydrogen, an unsubstituted $C_{1-6}$ alkyl, a halogen substituted $C_{1-6}$ alkyl, a hydroxy substituted $C_{1-6}$ alkyl or an unsubstituted $C_{1-6}$ alkoxy. In embodiments, $X^a$ can be hydrogen. In embodiments, $X^a$ can be an unsubstituted $C_{1-6}$ alkyl. In embodiments, $X^a$ can be methyl. In embodiments, $X^a$ can be a hydroxy substituted $C_{1-6}$ alkyl. In embodiments, $X^a$ can be —CH$_2$OH. In embodiments, X can be an unsubstituted $C_{1-6}$ alkoxy. In embodiments, $X^a$ can be methoxy. In embodiments, $X^a$ can be a halogen substituted $C_{1-6}$ alkyl. In embodiments, $X^a$ can be a fluoro substituted $C_{1-6}$ alkyl. In embodiments, $X^a$ can be —CH$_2$F.

Further to any embodiment above, in embodiments $L^a$ can be an unsubstituted $C_{13-29}$ heteroalkyl. In embodiments, $L^a$ can have the structure —(CH$_2$)$_{1-6}$—O—(CH$_2$)$_{11-21}$—CH$_3$. In embodiments, $L^a$ can have the structure —(CH$_2$)$_2$—O—(CH$_2$)$_{17}$—CH$_3$. In embodiments, $L^a$ can have the structure —(CH$_2$)$_3$—O—(CH$_2$)$_{15}$—CH$_3$. In embodiments, $L^a$ can have the structure —(CH$_2$)$_{1-6}$—O—(CH$_2$)$_{10-20}$—(CHCH$_3$)—CH$_3$.

Further to any embodiment above, in embodiments $L^a$ can be a substituted glyceryl moiety. In embodiments, $L^a$ can have the structure —(CH$_2$)—CH(OR$^{a1}$)—(CH$_2$)—O(CH$_2$)$_{11-21}$—CH$_3$, wherein R$^{a1}$ can be a substituted or unsubstituted aryl($C_{1-6}$ alkyl), a substituted or unsubstituted heteroaryl($C_{1-6}$ alkyl) or a substituted or unsubstituted heterocycloalkyl($C_{1-6}$ alkyl). In embodiment, R$^{a1}$ can be a substituted aryl($C_{1-6}$ alkyl). In embodiment, R$^{a1}$ can be an unsubstituted aryl($C_{1-6}$ alkyl). In embodiment, R$^{a1}$ can be a substituted heteroaryl($C_{1-6}$ alkyl). In embodiment, R$^{a1}$ can be an unsubstituted heteroaryl($C_{1-6}$ alkyl).). In embodiment, R$^{a1}$ can be a substituted heterocycloalkyl($C_{1-6}$ alkyl). In embodiment, R$^{a1}$ can be an unsubstituted heterocycloalkyl($C_{1-6}$ alkyl).

In embodiments, $L^a$ can have the structure

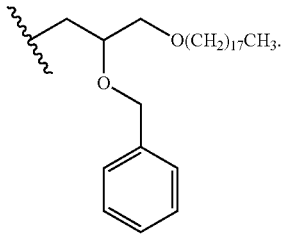

Further to any embodiment of the compound of Formula (Ia), in embodiments R$^a$ can be a substituted or unsubstituted aryl. In embodiments, the substituted aryl can be a substituted phenyl. In embodiments, the unsubstituted aryl can be an unsubstituted phenyl. In embodiments, the substituted aryl can be a substituted naphthyl. In embodiments, the unsubstituted aryl can be an unsubstituted naphthyl.

Further to any embodiment of the compound of Formula (Ia), in embodiments R$^a$ can be a substituted or unsubstituted aryl($C_{1-6}$ alkyl). In embodiments, the substituted aryl($C_{1-6}$ alkyl) can be a substituted benzyl. In embodiments, the unsubstituted aryl($C_{1-6}$ alkyl) can be an unsubstituted benzyl.

Further to any embodiment of the compound of Formula (Ia), in embodiments R$^a$ can be a substituted or unsubstituted heterocycloalkyl($C_{1-6}$ alkyl). In embodiments, the substituted or unsubstituted heterocycloalkyl($C_{1-6}$ alkyl) is a substituted or unsubstituted galactosyl.

Further to any embodiment of the compound of Formula (Ia), in embodiments $B_{Nuc(a)}$ can be a naturally occurring purine. In embodiments, $B_{Nuc(a)}$ can be a naturally occurring pyrimidine. In embodiments, $B_{Nuc(a)}$ can be a non-naturally occurring purine. In embodiments, $B_{Nuc(a)}$ can be a non-naturally occurring pyrimidine. The term "non-naturally occurring" and the like, in the context of purine or pyrimidine nucleoside $B_{Nuc(a)}$ groups, refers to moieties having a purine or pyrimidine core and additional chemical modifications not found in naturally occurring systems. Examples of purines include adenine, guanine, hypoxanthine, xanthine, theobromine, caffeine, uric acid, isoguanine, 2,6-diaminopurine. Examples of pyrimidines include cytosine, thymine, and uracil.

In embodiments, $B_{Nuc(a)}$ can be selected from:

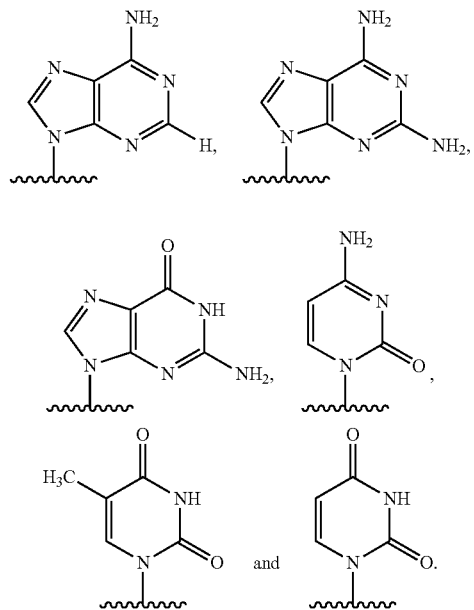

In embodiments, a compound of Formula (Ia) can have the structure:

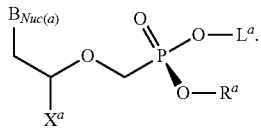

In embodiments, a compound of Formula (Ia) can have the structure:

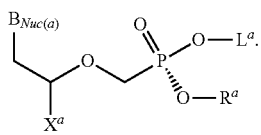

In embodiments, a compound of Formula (Ia) can have the structure:

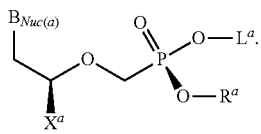

In embodiments, a compound of Formula (Ia) can have the structure:

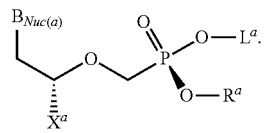

In embodiments, a compound of Formula (Ia) can have the structure:

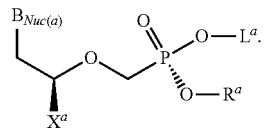

In embodiments, a compound of Formula (Ia) can have the structure:

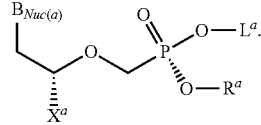

In embodiments, the compound can be selected from:

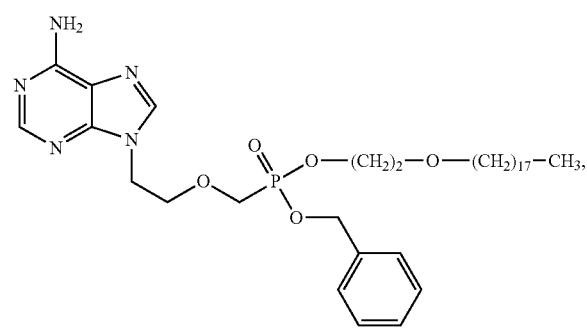

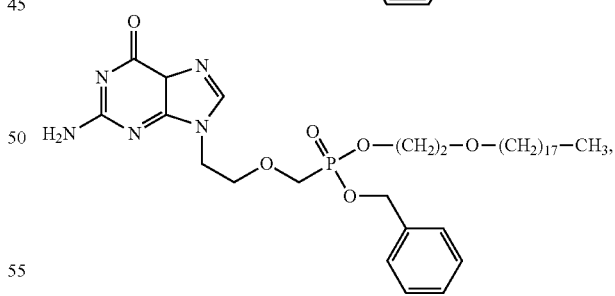

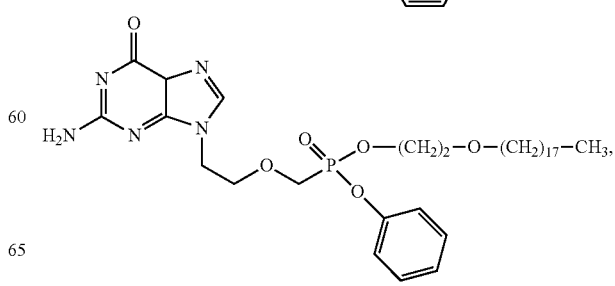

21
-continued
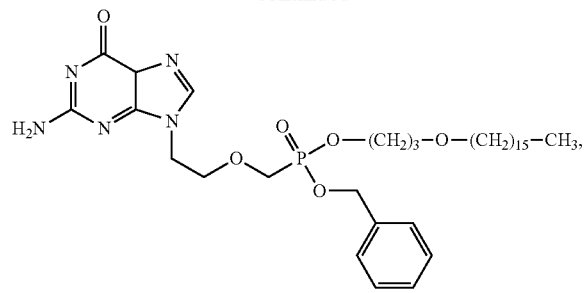
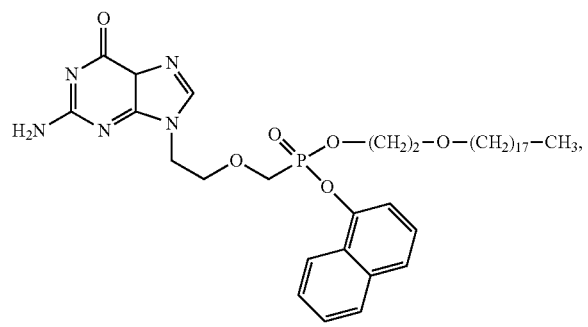
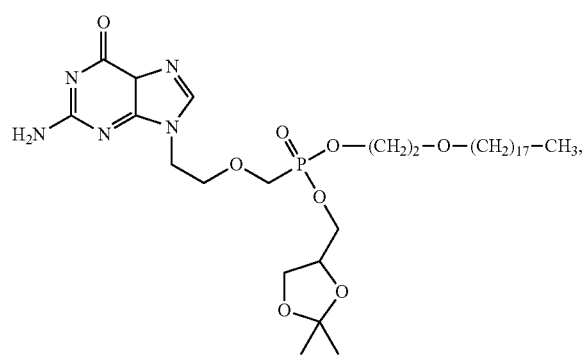
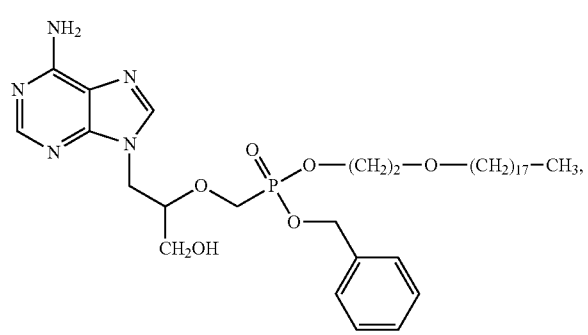
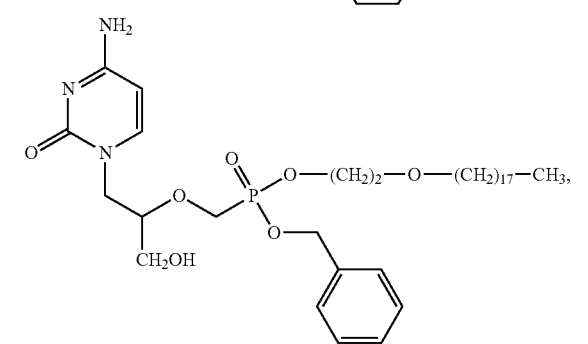
22
-continued
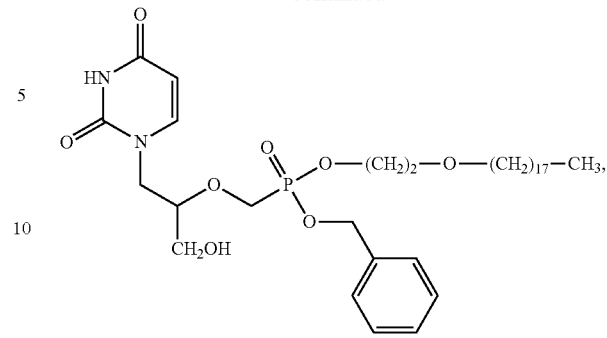
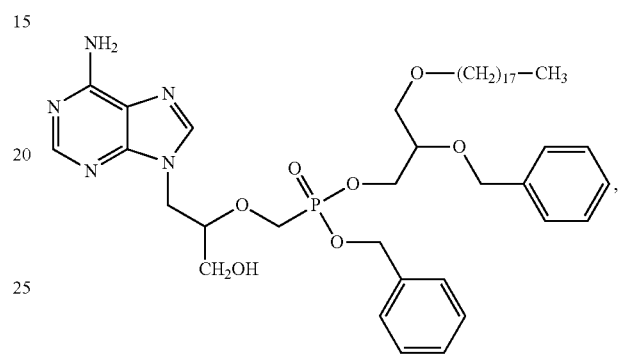
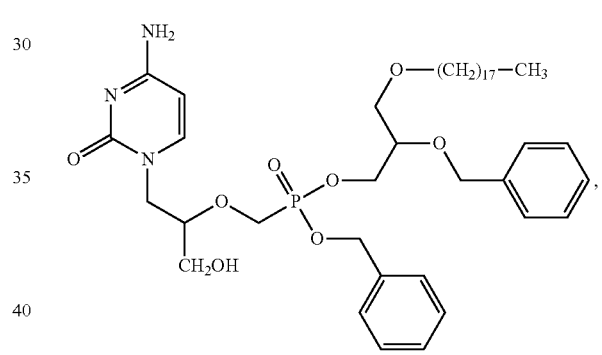
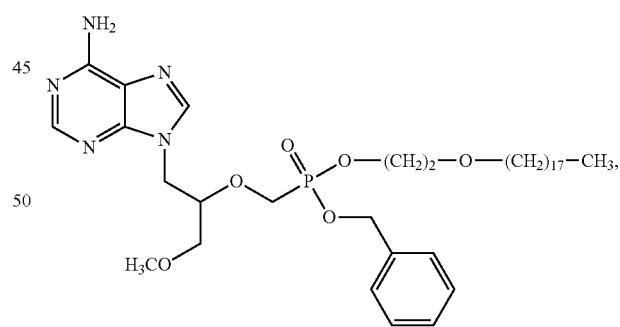
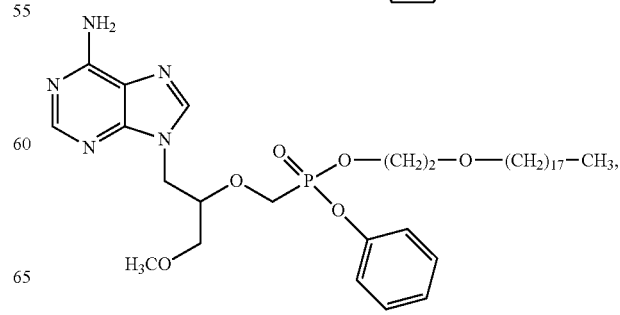

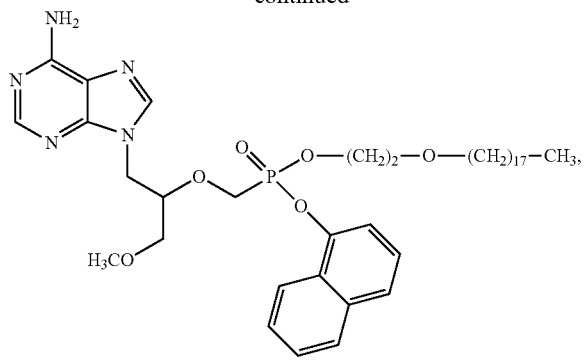

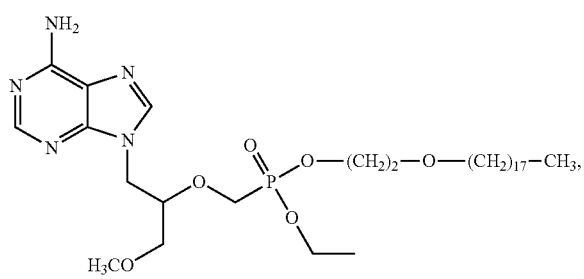

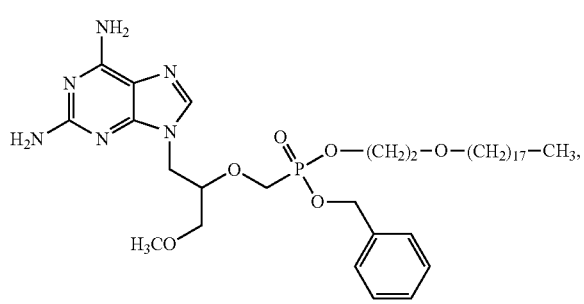

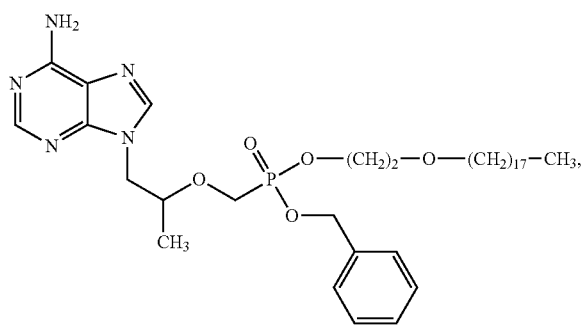

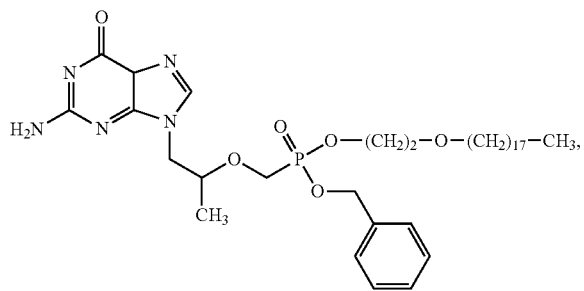

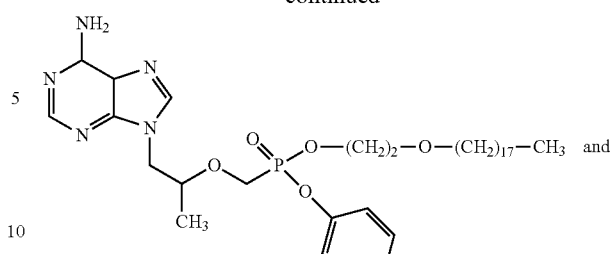

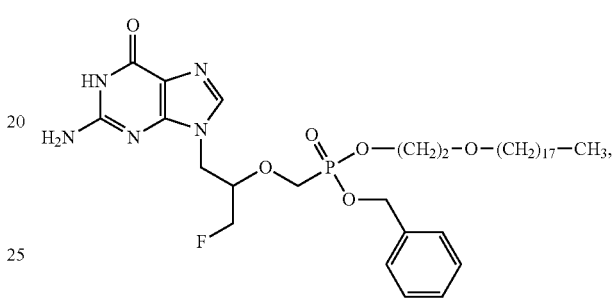

or a pharmaceutically acceptable salt, hydrate, solvate or crystalline form of any of the foregoing.

As can be seen from Formulae (I) and (Ia), there are many embodiments. For example, there are disclosed embodiments directed to a compound of Formula (I) and a compound of Formula (Ia) based on the identity of the acyclic nucleoside phosphonate scaffold. This is not intended to be an explicit or implicit admission that the embodiments are independent or distinct nor should it be interpreted as such. Rather, it is intended to convey information so that the full breadth of Formulae (I) and (Ia) can be understood. Furthermore, the following embodiments, and aspects thereof, are not meant to be limiting on the full breadth of the structure of Formula (I) and/or the structure of Formula (Ia).

Tables 1-10 following disclose structures contemplated herein. The structures of Tables 1-10 and are not intended to be limiting on the full breadth of the contemplated compounds represented by the structure of Formulae (I), (I-1), (I-2), (I-3), (I-4), (I-5) and (Ia). Moreover, it is contemplated that any one of the contemplated acyclic nucleoside phosphonate (ANP) scaffolds (PME-, (R)-PMP-, (S)-MPMP-, (S)-HPMP- and (S)-FPMP-) or their stereoisomers, can be used in combination with any of the contemplated combinations of naturally occurring or modified purine or pyrimidine base ($B_{Nuc}/B_{Nuc(a)}$, $L/L^a$ and $R/R^a$. Additionally, as the phosphorus atom of the ANP diester is a potential chiral center, it is understood that Rp and Sp (i.e., Cahn-Ingold-Prelog nomenclature as known in the art) stereochemical configurations are possible. Therefore, the structures below include stereochemical configurations possible for phosphorus.

TABLE 1

Phosphonomethoxyethyl (PME) diester compounds $B_{Nuc}/B_{Nuc(a)}$—O—P(=O)(O—L/L$^a$)(O—R/R$^a$)  or  (with wedge)  or  (racemic)

Rp or Sp (depends on substituents)    Rp, Sp (racemic)

| Cmpd No. | $B_{Nuc}/B_{Nuc(a)}$ | L/L$^a$ | R/R$^a$ | Name |
|---|---|---|---|---|
| 1-(RP, Sp) | guanin-9-yl | octadecyloxyethyl | benzyl | benzyl octadecyloxyethyl 9-(2-phosphonomethoxyethyl)guanine |
| 1a (fast) | guanin-9-yl | octadecyloxyethyl | benzyl | benzyl octadecyloxyethyl 9-(2-phosphonomethoxyethyl)guanine |
| 1b (slow) | guanin-9-yl | octadecyloxyethyl | benzyl | benzyl octadecyloxyethyl 9-(2-phosphonomethoxyethyl)guanine |
| 2 | adenine-9-yl | octadecyloxyethyl | benzyl | benzyl octadecyloxyethyl 9-(2-phosphonomethoxyethyl)adenine |
| 3 | cytosine-1-yl | octadecyloxyethyl | benzyl | benzyl octadecyloxyethyl 1-(2-phosphonomethoxyethyl)cytosine |
| 4 | thymin-1-yl | octadecyloxyethyl | benzyl | benzyl octadecyloxyethyl 1-(2-phosphonomethoxyethyl)thymine |
| 5 | uracil-1-yl | octadecyloxyethyl | benzyl | benzyl octadecyloxyethyl 9-(2-phosphonomethoxyethyl)uracil |
| 6 | 2,6-diaminopurin-9-yl | octadecyloxyethyl | benzyl | benzyl octadecyloxyethyl 9-(2-phosphonomethoxyethyl)-2,6-diaminopurine |
| 7 | guanin-9-yl | hexadecyloxypropyl | benzyl | benzyl hexadecyloxypropyl 9-(2-phosphonomethoxyethyl)guanine |
| 8 | adenine-9-yl | hexadecyloxypropyl | benzyl | benzyl hexadecyloxypropyl 9-(2-phosphonomethoxyethyl)adenine |
| 9 | cytosine-1-yl | hexadecyloxypropyl | benzyl | benzyl hexadecyloxypropyl 1-(2-phosphonomethoxyethyl)cytosine |
| 10 | thymin-1-yl | hexadecyloxypropyl | benzyl | benzyl hexadecyloxypropyl 1-(2-phosphonomethoxyethyl)thymine |
| 11 | uracil-1-yl | hexadecyloxypropyl | benzyl | benzyl hexadecyloxypropyl 9-(2-phosphonomethoxyethyl)uracil |
| 12 | 2,6-diaminopurin-9-yl | hexadecyloxypropyl | benzyl | benzyl hexadecyloxypropyl 9-(2-phosphonomethoxyethyl)-2,6-diaminopurine |
| 13 | guanin-9-yl | 1-O-octadecyl-2-O-benzyl-sn glyceryl | benzyl | benzyl 1-O-octadecyl-2-O-benzyl-sn glyceryl 9-(2-phosphonomethoxyethyl)guanine |
| 14 | adenine-9-yl | 1-O-octadecyl-2-O-benzyl-sn glyceryl | benzyl | benzyl 1-O-octadecyl-2-O-benzyl-sn glyceryl 9-(2-phosphonomethoxyethyl)adenine |
| 15 | cytosine-1-yl | 1-O-octadecyl-2-O-benzyl-sn glyceryl | benzyl | benzyl 1-O-octadecyl-2-O-benzyl-sn glyceryl 1-(2-phosphonomethoxyethyl)cytosine |
| 16 | thymin-1-yl | 1-O-octadecyl-2-O-benzyl-sn glyceryl | benzyl | benzyl 1-O-octadecyl-2-O-benzyl-sn glyceryl 1-(2-phosphonomethoxy-ethyl)thymine |
| 17 | uracil-1-yl | 1-O-octadecyl-2-O-benzyl-sn glyceryl | benzyl | benzyl 1-O-octadecyl-2-O-benzyl-sn glyceryl 9-(2-phosphonomethoxy-ethyl)uracil |
| 18 | 2,6-diaminopurin-9-yl | 1-O-octadecyl-2-O-benzyl-sn glyceryl | benzyl | enzyl 1-O-octadecyl-2-O-benzyl-sn glyceryl 9-(2-phosphonomethoxy-ethyl)-2,6-diaminopurine |
| 19 | guanin-9-yl | octadecyloxyethyl | phenyl | phenyl octadecyloxyethyl 9-(2-phosphonomethoxyethyl)guanine |
| 20 | adenine-9-yl | octadecyloxyethyl | phenyl | phenyl octadecyloxyethyl 9-(2-phosphonomethoxyethyl)adenine |
| 21 | cytosine-1-yl | octadecyloxyethyl | phenyl | phenyl octadecyloxyethyl 1-(2-phosphonomethoxyethyl)cytosine |
| 22 | thymin-1-yl | octadecyloxyethyl | phenyl | phenyl octadecyloxyethyl 1-(2-phosphonomethoxyethyl)thymine |
| 23 | uracil-1-yl | octadecyloxyethyl | phenyl | phenyl octadecyloxyethyl 9-(2-phosphonomethoxyethyl)uracil |
| 24 | 2,6-diaminopurin-9-yl | octadecyloxyethyl | phenyl | phenyl octadecyloxyethyl 9-(2-phosphonomethoxyethyl)-2,6-diaminopurine |
| 25 | guanin-9-yl | hexadecyloxypropyl | phenyl | phenyl hexadecyloxypropyl 9-(2-phosphonomethoxyethyl)guanine |
| 26 | adenine-9-yl | hexadecyloxypropyl | phenyl | phenyl hexadecyloxypropyl 9-(2-phosphonomethoxyethyl)adenine |
| 27 | cytosine-1-yl | hexadecyloxypropyl | phenyl | phenyl hexadecyloxypropyl 1-(2-phosphonomethoxyethyl)cytosine |

TABLE 1-continued

Phosphonomethoxyethyl (PME) diester compounds $B_{Nuc}/B_{Nuc(a)}$—O—P(=O)(—O—L/L$^a$)(—O—R/R$^a$)  or  $B_{Nuc}/B_{Nuc(a)}$—O—P(=O)(—O—L/L$^a$)(—O—R/R$^a$)  or  $B_{Nuc}/B_{Nuc(a)}$—O—P(=O)(—O—L/L$^a$)(—O—R/R$^a$)

Rp or Sp (depends on substituents)                         Rp, Sp (racemic)

| Cmpd No. | $B_{Nuc}/B_{Nuc(a)}$ | L/L$^a$ | R/R$^a$ | Name |
| --- | --- | --- | --- | --- |
| 28 | thymin-1-yl | hexadecyloxypropyl | phenyl | phenyl hexadecyloxypropyl 1-(2-phosphonomethoxyethyl)thymine |
| 29 | uracil-1-yl | hexadecyloxypropyl | phenyl | phenyl hexadecyloxypropyl 9-(2-phosphonomethoxyethyl)uracil |
| 30 | 2,6-diaminopurin-9-yl | hexadecyloxypropyl | phenyl | phenyl hexadecyloxypropyl 9-(2-phosphonomethoxyethyl)-2,6-diaminopurine |
| 31 | guanin-9-yl | 1-O-octadecyl-2-O-benzyl-sn glyceryl | phenyl | phenyl 1-O-octadecyl-2-O-benzyl-sn glyceryl 9-(2-phosphonomethoxyethyl)guanine |
| 32 | adenine-9-yl | 1-O-octadecyl-2-O-benzyl-sn glyceryl | phenyl | phenyl 1-O-octadecyl-2-O-benzyl-sn glyceryl 9-(2-phosphonomethoxyethyl)adenine |
| 33 | cytosine-1-yl | 1-O-octadecyl-2-O-benzyl-sn glyceryl | phenyl | phenyl 1-O-octadecyl-2-O-benzyl-sn glyceryl 1-(2-phosphonomethoxyethyl)cytosine |
| 34 | thymin-1-yl | 1-O-octadecyl-2-O-benzyl-sn glyceryl | phenyl | phenyl 1-O-octadecyl-2-O-benzyl-sn glyceryl 1-(2-phosphonomethoxyethyl)thymine |
| 35 | uracil-1-yl | 1-O-octadecyl-2-O-benzyl-sn glyceryl | phenyl | phenyl 1-O-octadecyl-2-O-benzyl-sn glyceryl 9-(2-phosphonomethoxyethyl)uracil |
| 36 | 2,6-diaminopurin-9-yl | 1-O-octadecyl-2-O-benzyl-sn glyceryl | phenyl | phenyl 1-O-octadecyl-2-O-benzyl-sn glyceryl 9-(2-phosphonomethoxyethyl)-2,6-diaminopurine |
| 37 | guanin-9-yl | octadecyloxyethyl | ethyl | ethyl octadecyloxyethyl 9-(2-phosphonomethoxyethyl)guanine |
| 38 | adenine-9-yl | octadecyloxyethyl | ethyl | ethyl octadecyloxyethyl 9-(2-phosphonomethoxyethyl)adenine |
| 39 | cytosine-1-yl | octadecyloxyethyl | ethyl | ethyl octadecyloxyethyl 1-(2-phosphonomethoxyethyl)cytosine |
| 40 | thymin-1-yl | octadecyloxyethyl | ethyl | ethyl octadecyloxyethyl 1-(2-phosphonomethoxyethyl)thymine |
| 41 | uracil-1-yl | octadecyloxyethyl | ethyl | ethyl octadecyloxyethyl 9-(2-phosphonomethoxyethyl)uracil |
| 42 | 2,6-diaminopurin-9-yl | octadecyloxyethyl | ethyl | ethyl octadecyloxyethyl 9-(2-phosphonomethoxyethyl)-2,6-diaminopurine |
| 43 | guanin-9-yl | hexadecyloxypropyl | ethyl | ethyl hexadecyloxypropyl 9-(2-phosphonomethoxyethyl)guanine |
| 44 | adenine-9-yl | hexadecyloxypropyl | ethyl | ethyl hexadecyloxypropyl 9-(2-phosphonomethoxyethyl)adenine |
| 45 | cytosine-1-yl | hexadecyloxypropyl | ethyl | ethyl hexadecyloxypropyl 1-(2-phosphonomethoxyethyl)cytosine |
| 46 | thymin-1-yl | hexadecyloxypropyl | ethyl | ethyl hexadecyloxypropyl 1-(2-phosphonomethoxyethyl)thymine |
| 47 | uracil-1-yl | hexadecyloxypropyl | ethyl | ethyl hexadecyloxypropyl 9-(2-phosphonomethoxyethyl)uracil |
| 48 | 2,6-diaminopurin-9-yl | hexadecyloxypropyl | ethyl | ethyl hexadecyloxypropyl 9-(2-phosphonomethoxyethyl)-2,6-diaminopurine |
| 49 | guanin-9-yl | 1-O-octadecyl-2-O-benzyl-sn glyceryl | ethyl | ethyl 1-O-octadecyl-2-O-benzyl-sn glyceryl 9-(2-phosphonomethoxyethyl)guanine |
| 50 | adenine-9-yl | 1-O-octadecyl-2-O-benzyl-sn glyceryl | ethyl | ethyl 1-O-octadecyl-2-O-benzyl-sn glyceryl 9-(2-phosphonomethoxyethyl)adenine |
| 51 | cytosine-1-yl | 1-O-octadecyl-2-O-benzyl-sn glyceryl | ethyl | ethyl 1-O-octadecyl-2-O-benzyl-sn glyceryl 1-(2-phosphonomethoxyethyl)cytosine |
| 52 | thymin-1-yl | 1-O-octadecyl-2-O-benzyl-sn glyceryl | ethyl | ethyl 1-O-octadecyl-2-O-benzyl-sn glyceryl 1-(2-phosphonomethoxyethyl)thymine |
| 53 | uracil-1-yl | 1-O-octadecyl-2-O-benzyl-sn glyceryl | ethyl | ethyl 1-O-octadecyl-2-O-benzyl-sn glyceryl 9-(2-phosphonomethoxyethyl)uracil |

TABLE 1-continued

Phosphonomethoxyethyl (PME) diester compounds $B_{Nuc}/B_{Nuc(a)}$—O—P(=O)(—O—L/L$^a$)(—O—R/R$^a$) or (Rp or Sp, depends on substituents) ... Rp, Sp (racemic)

| Cmpd No. | $B_{Nuc}/B_{Nuc(a)}$ | L/L$^a$ | R/R$^a$ | Name |
|---|---|---|---|---|
| 54 | 2,6-diaminopurin-9-yl | 1-O-octadecyl-2-O-benzyl-sn glyceryl | ethyl | ethyl 1-O-octadecyl-2-O-benzyl-sn glyceryl 9-(2-phosphonomethoxyethyl)-2,6-diaminopurine |
| 55 | guanin-9-yl | octadecyloxyethyl | galactosyl | galactosyl octadecyloxyethyl 9-(2-phosphonomethoxyethyl)guanine |
| 56 | adenine-9-yl | octadecyloxyethyl | galactosyl | galactosyl octadecyloxyethyl 9-(2-phosphonomethoxyethyl)adenine |
| 57 | cytosine-1-yl | octadecyloxyethyl | galactosyl | galactosyl octadecyloxyethyl 1-(2-phosphonomethoxyethyl)cytosine |
| 58 | thymin-1-yl | octadecyloxyethyl | galactosyl | galactosyl octadecyloxyethyl 1-(2-phosphonomethoxyethyl)thymine |
| 59 | uracil-1-yl | octadecyloxyethyl | galactosyl | galactosyl octadecyloxyethyl 9-(2-phosphonomethoxyethyl)uracil |
| 60 | 2,6-diaminopurin-9-yl | octadecyloxyethyl | galactosyl | galactosyl octadecyloxyethyl 9-(2-phosphonomethoxyethyl)-2,6-diaminopurine |
| 61 | guanin-9-yl | hexadecyloxypropyl | galactosyl | galactosyl hexadecyloxypropyl 9-(2-phosphonomethoxyethyl)guanine |
| 62 | adenine-9-yl | hexadecyloxypropyl | galactosyl | galactosyl hexadecyloxypropyl 9-(2-phosphonomethoxyethyl)adenine |
| 63 | cytosine-1-yl | hexadecyloxypropyl | galactosyl | galactosyl hexadecyloxypropyl 1-(2-phosphonomethoxyethyl)cytosine |
| 64 | thymin-1-yl | hexadecyloxypropyl | galactosyl | galactosyl hexadecyloxypropyl 1-(2-phosphonomethoxyethyl)thymine |
| 65 | uracil-1-yl | hexadecyloxypropyl | galactosyl | galactosyl hexadecyloxypropyl 9-(2-phosphonomethoxyethyl)uracil |
| 66 | 2,6-diaminopurin-9-yl | hexadecyloxypropyl | galactosyl | galactosyl hexadecyloxypropyl 9-(2-phosphonomethoxyethyl)-2,6-diaminopurine |
| 67 | guanin-9-yl | 1-O-octadecyl-2-O-benzyl-sn glyceryl | galactosyl | galactosyl 1-O-octadecyl-2-O-benzyl-sn glyceryl 9-(2-phosphonomethoxyethyl)guanine |
| 68 | adenine-9-yl | 1-O-octadecyl-2-O-benzyl-sn glyceryl | galactosyl | galactosyl 1-O-octadecyl-2-O-benzyl-sn glyceryl 9-(2-phosphonomethoxyethyl)adenine |
| 69 | cytosine-1-yl | 1-O-octadecyl-2-O-benzyl-sn glyceryl | galactosyl | galactosyl 1-O-octadecyl-2-O-benzyl-sn glyceryl 1-(2-phosphonomethoxyethyl)cytosine |
| 70 | thymin-1-yl | 1-O-octadecyl-2-O-benzyl-sn glyceryl | galactosyl | galactosyl 1-O-octadecyl-2-O-benzyl-sn glyceryl 1-(2-phosphonomethoxyethyl)thymine |
| 71 | uracil-1-yl | 1-O-octadecyl-2-O-benzyl-sn glyceryl | galactosyl | galactosyl 1-O-octadecyl-2-O-benzyl-sn glyceryl 9-(2-phosphonomethoxyethyl)uracil |
| 72 | 2,6-diaminopurin-9-yl | 1-O-octadecyl-2-O-benzyl-sn glyceryl | galactosyl | galactosyl 1-O-octadecyl-2-O-benzyl-sn glyceryl 9-(2-phosphonomethoxyethyl)-2,6-diaminopurine |

TABLE 2

(R)-phosphonomethoxypropyl [(R)-PMP] diester compounds

Rp or Sp (depends on substituents) ... Rp, Sp (racemic)

| Cmpd No. | $B_{Nuc}/B_{Nuc(a)}$ | L/L$^a$ | R/R$^a$ | Name |
|---|---|---|---|---|
| 73 | guanin-9-yl | octadecyloxyethyl | benzyl | benzyl octadecyloxyethyl 9-(R)-[(2-phosphonomethoxy)propyl]guanine |

TABLE 2-continued (R)-phosphonomethoxypropyl [(R)-PMP] diester compounds $B_{Nuc}/B_{Nuc(a)}$ — O — P(=O)(O—L/L$^a$)(O—R/R$^a$) with CH$_3$ stereocenter    or    (with wedge bond at P)    or    (racemic)

Rp or Sp (depends on substituents)                                Rp, Sp (racemic)

| Cmpd No. | $B_{Nuc}/B_{Nuc(a)}$ | L/L$^a$ | R/R$^a$ | Name |
|---|---|---|---|---|
| 74 | adenine-9-yl | octadecyloxyethyl | benzyl | benzyl octadecyloxyethyl 9-(R)-[(2-phosphonomethoxy)propyl]adenine |
| 75 | cytosine-1-yl | octadecyloxyethyl | benzyl | benzyl octadecyloxyethyl 1-(R)-[(2-phosphonomethoxy)propyl]cytosine |
| 76 | thymin-1-yl | octadecyloxyethyl | benzyl | benzyl octadecyloxyethyl 1-(R)-[(2-phosphonomethoxy)propyl]thymine |
| 77 | uracil-1-yl | octadecyloxyethyl | benzyl | benzyl octadecyloxyethyl 1-(R)-[(2-phosphonomethoxy)propyl]uracil |
| 78 | 2,6-diaminopurin-9-yl | octadecyloxyethyl | benzyl | benzyl octadecyloxyethyl 9-(R)-[(2-phosphonomethoxy)propyl]2,6-diaminopurine |
| 79 | guanin-9-yl | hexadecyloxypropyl | benzyl | benzyl hexadecyloxypropyl 9-(R)-[(2-phosphonomethoxy)propyl]guanine |
| 80 | adenine-9-yl | hexadecyloxypropyl | benzyl | benzyl hexadecyloxypropyl 9-(R)-[(2-phosphonomethoxy)propyl]adenine |
| 81 | cytosine-1-yl | hexadecyloxypropyl | benzyl | benzyl hexadecyloxypropyl 1-(R)-[(2-phosphonomethoxy)propyl]cytosine |
| 82 | thymin-1-yl | hexadecyloxypropyl | benzyl | benzyl hexadecyloxypropyl 1-(R)-[(2-phosphonomethoxy)propyl]thymine |
| 83 | uracil-1-yl | hexadecyloxypropyl | benzyl | benzyl hexadecyloxypropyl 1-(R)-[(2-phosphonomethoxy)propyl]uracil |
| 84 | 2,6-diaminopurin-9-yl | hexadecyloxypropyl | benzyl | benzyl hexadecyloxypropyl 9-(R)-[(2-phosphonomethoxy)propyl]2,6-diaminopurine |
| 85 | guanin-9-yl | 1-O-octadecyl-2-O-benzyl-sn glyceryl | benzyl | benzyl 1-O-octadecyl-2-O-benzyl-sn glyceryl 9-(R)-[(2-phosphonomethoxy)propyl]guanine |
| 86 | adenine-9-yl | 1-O-octadecyl-2-O-benzyl-sn glyceryl | benzyl | benzyl 1-O-octadecyl-2-O-benzyl-sn glyceryl 9-(R)-[(2-phosphonomethoxy)propyl]adenine |
| 87 | cytosine-1-yl | 1-O-octadecyl-2-O-benzyl-sn glyceryl | benzyl | benzyl 1-O-octadecyl-2-O-benzyl-sn glyceryl 1-(R)-[(2-phosphonomethoxy)propyl]cytosine |
| 88 | thymin-1-yl | 1-O-octadecyl-2-O-benzyl-sn glyceryl | benzyl | benzyl 1-O-octadecyl-2-O-benzyl-sn glyceryl 1-(R)-[(2-phosphonomethoxy)propyl]thymine |
| 89 | uracil-1-yl | 1-O-octadecyl-2-O-benzyl-sn glyceryl | benzyl | benzyl 1-O-octadecyl-2-O-benzyl-sn glyceryl 1-(R)-[(2-phosphonomethoxy)propyl]uracil |
| 90 | 2,6-diaminopurin-9-yl | 1-O-octadecyl-2-O-benzyl-sn glyceryl | benzyl | benzyl 1-O-octadecyl-2-O-benzyl-sn glyceryl 9-(R)-[(2-phosphonomethoxy)propyl]2,6-diaminopurine |
| 91 | guanin-9-yl | octadecyloxyethyl | phenyl | phenyl octadecyloxyethyl 9-(R)-[(2-phosphonomethoxy)propyl]guanine |
| 92 | adenine-9-yl | octadecyloxyethyl | phenyl | phenyl octadecyloxyethyl 9-(R)-[(2-phosphonomethoxy)propyl]adenine |
| 93 | cytosine-1-yl | octadecyloxyethyl | phenyl | phenyl octadecyloxyethyl 1-(R)-[(2-phosphonomethoxy)propyl]cytosine |
| 94 | thymin-1-yl | octadecyloxyethyl | phenyl | phenyl octadecyloxyethyl 1-(R)-[(2-phosphonomethoxy)propyl]thymine |
| 95 | uracil-1-yl | octadecyloxyethyl | phenyl | phenyl octadecyloxyethyl 1-(R)-[(2-phosphonomethoxy)propyl]uracil |
| 96 | 2,6-diaminopurin-9-yl | octadecyloxyethyl | phenyl | phenyl octadecyloxyethyl 9-(R)-[(2-phosphonomethoxy)propyl]2,6-diaminopurine |
| 97 | guanin-9-yl | hexadecyloxypropyl | phenyl | phenyl hexadecyloxypropyl 9-(R)-[(2-phosphonomethoxy)propyl]guanine |
| 98 | adenine-9-yl | hexadecyloxypropyl | phenyl | phenyl hexadecyloxypropyl 9-(R)-[(2-phosphonomethoxy)propyl]adenine |
| 99 | cytosine-1-yl | hexadecyloxypropyl | phenyl | phenyl hexadecyloxypropyl 1-(R)-[(2-phosphonomethoxy)propyl]cytosine |
| 100 | thymin-1-yl | hexadecyloxypropyl | phenyl | phenyl hexadecyloxypropyl 1-(R)-[(2-phosphonomethoxy)propyl]thymine |
| 101 | uracil-1-yl | hexadecyloxypropyl | phenyl | phenyl hexadecyloxypropyl 1-(R)-[(2-phosphonomethoxy)propyl]uracil |

TABLE 2-continued (R)-phosphonomethoxypropyl [(R)-PMP] diester compounds $B_{Nuc}/B_{Nuc(a)}$—O—P(=O)(O—L/L$^a$)(O—R/R$^a$) with CH$_3$ stereocenter  or  Rp or Sp (depends on substituents)    Rp, Sp (racemic)

| Cmpd No. | $B_{Nuc}/B_{Nuc(a)}$ | L/L$^a$ | R/R$^a$ | Name |
| --- | --- | --- | --- | --- |
| 102 | 2,6-diaminopurin-9-yl | hexadecyloxypropyl | phenyl | phenyl hexadecyloxypropyl 9-(R)-[(2-phosphonomethoxy)propyl]2,6-diaminopurine |
| 103 | guanin-9-yl | 1-O-octadecyl-2-O-benzyl-sn glyceryl | phenyl | phenyl 1-O-octadecyl-2-O-benzyl-sn glyceryl 9-(R)-[(2-phosphonomethoxy)propyl]guanine |
| 104 | adenine-9-yl | 1-O-octadecyl-2-O-benzyl-sn glyceryl | phenyl | phenyl 1-O-octadecyl-2-O-benzyl-sn glyceryl 9-(R)-[(2-phosphonomethoxy)propyl]adenine |
| 105 | cytosine-1-yl | 1-O-octadecyl-2-O-benzyl-sn glyceryl | phenyl | phenyl 1-O-octadecyl-2-O-benzyl-sn glyceryl 1-(R)-[(2-phosphonomethoxy)propyl]cytosine |
| 106 | thymin-1-yl | 1-O-octadecyl-2-O-benzyl-sn glyceryl | phenyl | phenyl 1-O-octadecyl-2-O-benzyl-sn glyceryl 1-(R)-[(2-phosphonomethoxy)propyl]thymine |
| 107 | uracil-1-yl | 1-O-octadecyl-2-O-benzyl-sn glyceryl | phenyl | phenyl 1-O-octadecyl-2-O-benzyl-sn glyceryl 1-(R)-[(2-phosphonomethoxy)propyl]uracil |
| 108 | 2,6-diaminopurin-9-yl | 1-O-octadecyl-2-O-benzyl-sn glyceryl | phenyl | phenyl 1-O-octadecyl-2-O-benzyl-sn glyceryl 9-(R)-[(2-phosphonomethoxy)propyl]2,6-diaminopurine |
| 109 | guanin-9-yl | octadecyloxyethyl | ethyl | ethyl octadecyloxyethyl 9-(R)-[(2-phosphonomethoxy)propyl]guanine |
| 110 | adenine-9-yl | octadecyloxyethyl | ethyl | ethyl octadecyloxyethyl 9-(R)-[(2-phosphonomethoxy)propyl]adenine |
| 111 | cytosine-1-yl | octadecyloxyethyl | ethyl | ethyl octadecyloxyethyl 1-(R)-[(2-phosphonomethoxy)propyl]cytosine |
| 112 | thymin-1-yl | octadecyloxyethyl | ethyl | ethyl octadecyloxyethyl 1-(R)-[(2-phosphonomethoxy)propyl]thymine |
| 113 | uracil-1-yl | octadecyloxyethyl | ethyl | ethyl octadecyloxyethyl 1-(R)-[(2-phosphonomethoxy)propyl]uracil |
| 114 | 2,6-diaminopurin-9-yl | octadecyloxyethyl | ethyl | ethyl octadecyloxyethyl 9-(R)-[(2-phosphonomethoxy)propyl]2,6-diaminopurine |
| 115 | guanin-9-yl | hexadecyloxypropyl | ethyl | ethyl hexadecyloxypropyl 9-(R)-[(2-phosphonomethoxy)propyl]guanine |
| 116 | adenine-9-yl | hexadecyloxypropyl | ethyl | ethyl hexadecyloxypropyl 9-(R)-[(2-phosphonomethoxy)propyl]adenine |
| 117 | cytosine-1-yl | hexadecyloxypropyl | ethyl | ethyl hexadecyloxypropyl 1-(R)-[(2-phosphonomethoxy)propyl]cytosine |
| 118 | thymin-1-yl | hexadecyloxypropyl | ethyl | ethyl hexadecyloxypropyl 1-(R)-[(2-phosphonomethoxy)propyl]thymine |
| 119 | uracil-1-yl | hexadecyloxypropyl | ethyl | ethyl hexadecyloxypropyl 1-(R)-[(2-phosphonomethoxy)propyl]uracil |
| 120 | 2,6-diaminopurin-9-yl | hexadecyloxypropyl | ethyl | ethyl hexadecyloxypropyl 9-(R)-[(2-phosphonomethoxy)propyl]2,6-diaminopurine |
| 121 | guanin-9-yl | 1-O-octadecyl-2-O-benzyl-sn glyceryl | ethyl | ethyl 1-O-octadecyl-2-O-benzyl-sn glyceryl 9-(R)-[(2-phosphonomethoxy)propyl]guanine |
| 122 | adenine-9-yl | 1-O-octadecyl-2-O-benzyl-sn glyceryl | ethyl | ethyl 1-O-octadecyl-2-O-benzyl-sn glyceryl 9-(R)-[(2-phosphonomethoxy)propyl]adenine |
| 123 | cytosine-1-yl | 1-O-octadecyl-2-O-benzyl-sn glyceryl | ethyl | ethyl 1-O-octadecyl-2-O-benzyl-sn glyceryl 1-(R)-[(2-phosphonomethoxy)propyl]cytosine |
| 124 | thymin-1-yl | 1-O-octadecyl-2-O-benzyl-sn glyceryl | ethyl | ethyl 1-O-octadecyl-2-O-benzyl-sn glyceryl 1-(R)-[(2-phosphonomethoxy)propyl]thymine |
| 125 | uracil-1-yl | 1-O-octadecyl-2-O-benzyl-sn glyceryl | ethyl | ethyl 1-O-octadecyl-2-O-benzyl-sn glyceryl 1-(R)-[(2-phosphonomethoxy)propyl]uracil |

TABLE 2-continued (R)-phosphonomethoxypropyl [(R)-PMP] diester compounds

Rp or Sp (depends on substituents)    Rp, Sp (racemic)

| Cmpd No. | $B_{Nuc}/B_{Nuc(a)}$ | $L/L^a$ | $R/R^a$ | Name |
| --- | --- | --- | --- | --- |
| 126 | 2,6-diaminopurin-9-yl | 1-O-octadecyl-2-O-benzyl-sn glyceryl | ethyl | phenyl 1-O-octadecyl-2-O-benzyl-sn glyceryl 9-(R)-[(2-phosphonomethoxy)propyl]2,6-diaminopurine |
| 127 | guanin-9-yl | octadecyloxyethyl | galactosyl | galactosyl octadecyloxyethyl 9-(R)-[(2-phosphonomethoxy)propyl]guanine |
| 128 | adenine-9-yl | octadecyloxyethyl | galactosyl | galactosyl octadecyloxyethyl 9-(R)-[(2-phosphonomethoxy)propyl]adenine |
| 129 | cytosine-1-yl | octadecyloxyethyl | galactosyl | galactosyl octadecyloxyethyl 1-(R)-[(2-phosphonomethoxy)propyl]cytosine |
| 130 | thymin-1-yl | octadecyloxyethyl | galactosyl | galactosyl octadecyloxyethyl 1-(R)-[(2-phosphonomethoxy)propyl]thymine |
| 131 | uracil-1-yl | octadecyloxyethyl | galactosyl | galactosyl octadecyloxyethyl 1-(R)-[(2-phosphonomethoxy)propyl]uracil |
| 132 | 2,6-diaminopurin-9-yl | octadecyloxyethyl | galactosyl | galactosyl octadecyloxyethyl 9-(R)-[(2-phosphonomethoxy)propyl]2,6-diaminopurine |
| 133 | guanin-9-yl | hexadecyloxypropyl | galactosyl | galactosyl hexadecyloxypropyl 9-(R)-[(2-phosphonomethoxy)propyl]guanine |
| 134 | adenine-9-yl | hexadecyloxypropyl | galactosyl | galactosyl hexadecyloxypropyl 9-(R)-[(2-phosphonomethoxy)propyl]adenine |
| 135 | cytosine-1-yl | hexadecyloxypropyl | galactosyl | galactosyl hexadecyloxypropyl 1-(R)-[(2-phosphonomethoxy)propyl]cytosine |
| 136 | thymin-1-yl | hexadecyloxypropyl | galactosyl | galactosyl hexadecyloxypropyl 1-(R)-[(2-phosphonomethoxy)propyl]thymine |
| 137 | uracil-1-yl | hexadecyloxypropyl | galactosyl | galactosyl hexadecyloxypropyl 1-(R)-[(2-phosphonomethoxy)propyl]uracil |
| 138 | 2,6-diaminopurin-9-yl | hexadecyloxypropyl | galactosyl | galactosyl hexadecyloxypropyl 9-(R)-[(2-phosphonomethoxy)propyl]2,6-diaminopurine |
| 139 | guanin-9-yl | 1-O-octadecyl-2-O-benzyl-sn glyceryl | galactosyl | galactosyl 1-O-octadecyl-2-O-benzyl-sn glyceryl 9-(R)-[(2-phosphonomethoxy)propyl]guanine |
| 140 | adenine-9-yl | 1-O-octadecyl-2-O-benzyl-sn glyceryl | galactosyl | galactosyl 1-O-octadecyl-2-O-benzyl-sn glyceryl 9-(R)-[(2-phosphonomethoxy)propyl]adenine |
| 141 | cytosine-1-yl | 1-O-octadecyl-2-O-benzyl-sn glyceryl | galactosyl | galactosyl 1-O-octadecyl-2-O-benzyl-sn glyceryl 1-(R)-[(2-phosphonomethoxy)propyl]cytosine |
| 142 | thymin-1-yl | 1-O-octadecyl-2-O-benzyl-sn glyceryl | galactosyl | galactosyl 1-O-octadecyl-2-O-benzyl-sn glyceryl 1-(R)-[(2-phosphonomethoxy)propyl]thymine |
| 143 | uracil-1-yl | 1-O-octadecyl-2-O-benzyl-sn glyceryl | galactosyl | galactosyl 1-O-octadecyl-2-O-benzyl-sn glyceryl 1-(R)-[(2-phosphonomethoxy)propyl]uracil |
| 144 | 2,6-diaminopurin-9-yl | 1-O-octadecyl-2-O-benzyl-sn glyceryl | galactosyl | galactosyl 1-O-octadecyl-2-O-benzyl-sn glyceryl 9-(R)-[(2-phosphonomethoxy)propyl]2,6-diaminopurine |

TABLE 3

(S)-3-methoxy-2-phosphonmethoxypropyl [(S)-MPMP] diester compounds

Rp or Sp (depends on substituents)     Rp, Sp (racemic)

| Cmpd No. | $B_{Nuc}/B_{Nuc(a)}$ | $L/L^a$ | $R/R^a$ | Name |
|---|---|---|---|---|
| 145 | guanin-9-yl | octadecyloxyethyl | benzyl | benzyl octadecyloxyethyl 9-(S)-[(3-methoxy-2-phosphonomethoxy)propyl]guanine |
| 146 | adenine-9-yl | octadecyloxyethyl | benzyl | benzyl octadecyloxyethyl 9-(S)-[(3-methoxy-2-phosphonomethoxy)propyl]adenine |
| 147 | cytosine-1-yl | octadecyloxyethyl | benzyl | benzyl octadecyloxyethyl 1-(S)-[(3-methoxy-2-phosphonomethoxy)propyl]cytosine |
| 148 | thymin-1-yl | octadecyloxyethyl | benzyl | benzyl octadecyloxyethyl 1-(S)-[(3-methoxy-2-phosphonomethoxy)propyl]thymine |
| 149 | uracil-1-yl | octadecyloxyethyl | benzyl | benzyl octadecyloxyethyl 1-(S)-[(3-methoxy-2-phosphonomethoxy)propyl]uracil |
| 150 | 2,6-diaminopurin-9-yl | octadecyloxyethyl | benzyl | benzyl octadecyloxyethyl 9-(S)-[(3-methoxy-2-phosphonomethoxy)propyl]2,6-diaminopurine |
| 151 | guanin-9-yl | hexadecyloxypropyl | benzyl | benzyl hexadecyloxypropyl 9-(S)-[(3-methoxy-2-phosphonomethoxy)propyl]guanine |
| 152 | adenine-9-yl | hexadecyloxypropyl | benzyl | benzyl hexadecyloxypropyl 9-(S)-[(3-methoxy-2-phosphonomethoxy)propyl]adenine |
| 153 | cytosine-1-yl | hexadecyloxypropyl | benzyl | benzyl hexadecyloxypropyl 1-(S)-[(3-methoxy-2-phosphonomethoxy)propyl]cytosine |
| 154 | thymin-1-yl | hexadecyloxypropyl | benzyl | benzyl hexadecyloxypropyl 1-(S)-[(3-methoxy-2-phosphonomethoxy)propyl]thymine |
| 155 | uracil-1-yl | hexadecyloxypropyl | benzyl | benzyl hexadecyloxypropyl 1-(S)-[(3-methoxy-2-phosphonomethoxy)propyl]uracil |
| 156 | 2,6-diaminopurin-9-yl | hexadecyloxypropyl | benzyl | benzyl hexadecyloxypropyl 9-(S)-[(3-methoxy-2-phosphonomethoxy)propyl]2,6-diaminopurine |
| 157 | guanin-9-yl | 1-O-octadecyl-2-O-benzyl-sn glyceryl | benzyl | benzyl 1-O-octadecyl-2-O-benzyl-sn glyceryl 9-(S)-[(3-methoxy-2-phosphonomethoxy)propyl]guanine |
| 158 | adenine-9-yl | 1-O-octadecyl-2-O-benzyl-sn glyceryl | benzyl | benzyl 1-O-octadecyl-2-O-benzyl-sn glyceryl 9-(S)-[(3-methoxy-2-phosphonomethoxy)propyl]adenine |
| 159 | cytosine-1-yl | 1-O-octadecyl-2-O-benzyl-sn glyceryl | benzyl | benzyl 1-O-octadecyl-2-O-benzyl-sn glyceryl 1-(S)-[(3-methoxy-2-phosphonomethoxy)propyl]cytosine |
| 160 | thymin-1-yl | 1-O-octadecyl-2-O-benzyl-sn glyceryl | benzyl | benzyl 1-O-octadecyl-2-O-benzyl-sn glyceryl 1-(S)-[(3-methoxy-2-phosphonomethoxy)propyl]thymine |
| 161 | uracil-1-yl | 1-O-octadecyl-2-O-benzyl-sn glyceryl | benzyl | benzyl 1-O-octadecyl-2-O-benzyl-sn glyceryl 1-(S)-[(3-methoxy-2-phosphonomethoxy)propyl]uracil |
| 162 | 2,6-diaminopurin-9-yl | 1-O-octadecyl-2-O-benzyl-sn glyceryl | benzyl | benzyl 1-O-octadecyl-2-O-benzyl-sn glyceryl 9-(S)-[(3-methoxy-2-phosphonomethoxy)propyl]2,6-diaminopurine |
| 163 | guanin-9-yl | octadecyloxyethyl | phenyl | phenyl octadecyloxyethyl 9-(S)-[(3-methoxy-2-phosphonomethoxy)propyl]guanine |
| 164 | adenine-9-yl | octadecyloxyethyl | phenyl | phenyl octadecyloxyethyl 9-(S)-[(3-methoxy-2-phosphonomethoxy)propyl]adenine |
| 165 | cytosine-1-yl | octadecyloxyethyl | phenyl | phenyl octadecyloxyethyl 1-(S)-[(3-methoxy-2-phosphonomethoxy)propyl]cytosine |

TABLE 3-continued (S)-3-methoxy-2-phosphonmethoxypropyl [(S)-MPMP] diester compounds Rp or Sp (depends on substituents)   Rp, Sp (racemic)

| Cmpd No. | $B_{Nuc}/B_{Nuc(a)}$ | $L/L^a$ | $R/R^a$ | Name |
| --- | --- | --- | --- | --- |
| 166 | thymin-1-yl | octadecyloxyethyl | phenyl | phenyl octadecyloxyethyl 1-(S)-[(3-methoxy-2-phosphonomethoxy)propyl]thymine |
| 167 | uracil-1-yl | octadecyloxyethyl | phenyl | phenyl octadecyloxyethyl 1-(S)-[(3-methoxy-2-phosphonomethoxy)propyl]uracil |
| 168 | 2,6-diaminopurin-9-yl | octadecyloxyethyl | phenyl | phenyl octadecyloxyethyl 9-(S)-[(3-methoxy-2-phosphonomethoxy)propyl]2,6-diaminopurine |
| 169 | guanin-9-yl | hexadecyloxypropyl | phenyl | phenyl hexadecyloxypropyl 9-(S)-[(3-methoxy-2-phosphonomethoxy)propyl]guanine |
| 170 | adenine-9-yl | hexadecyloxypropyl | phenyl | phenyl hexadecyloxypropyl 9-(S)-[(3-methoxy-2-phosphonomethoxy)propyl]adenine |
| 171 | cytosine-1-yl | hexadecyloxypropyl | phenyl | phenyl hexadecyloxypropyl 1-(S)-[(3-methoxy-2-phosphonomethoxy)propyl]cytosine |
| 172 | thymin-1-yl | hexadecyloxypropyl | phenyl | phenyl hexadecyloxypropyl 1-(S)-[(3-methoxy-2-phosphonomethoxy)propyl]thymine |
| 173 | uracil-1-yl | hexadecyloxypropyl | phenyl | phenyl hexadecyloxypropyl 1-(S)-[(3-methoxy-2-phosphonomethoxy)propyl]uracil |
| 174 | 2,6-diaminopurin-9-yl | hexadecyloxypropyl | phenyl | phenyl hexadecyloxypropyl 9-(S)-[(3-methoxy-2-phosphonomethoxy)propyl]2,6-diaminopurine |
| 175 | guanin-9-yl | 1-O-octadecyl-2-O-benzyl-sn glyceryl | phenyl | phenyl 1-O-octadecyl-2-O-benzyl-sn glyceryl 9-(S)-[(3-methoxy-2-phosphonomethoxy)propyl]guanine |
| 176 | adenine-9-yl | 1-O-octadecyl-2-O-benzyl-sn glyceryl | phenyl | phenyl 1-O-octadecyl-2-O-benzyl-sn glyceryl 9-(S)-[(3-methoxy-2-phosphonomethoxy)propyl]adenine |
| 177 | cytosine-1-yl | 1-O-octadecyl-2-O-benzyl-sn glyceryl | phenyl | phenyl 1-O-octadecyl-2-O-benzyl-sn glyceryl 1-(S)-[(3-methoxy-2-phosphonomethoxy)propyl]cytosine |
| 178 | thymin-1-yl | 1-O-octadecyl-2-O-benzyl-sn glyceryl | phenyl | phenyl 1-O-octadecyl-2-O-benzyl-sn glyceryl 1-(S)-[(3-methoxy-2-phosphonomethoxy)propyl]thymine |
| 179 | uracil-1-yl | 1-O-octadecyl-2-O-benzyl-sn glyceryl | phenyl | phenyl 1-O-octadecyl-2-O-benzyl-sn glyceryl 1-(S)-[(3-methoxy-2-phosphonomethoxy)propyl]uracil |
| 180 | 2,6-diaminopurin-9-yl | 1-O-octadecyl-2-O-benzyl-sn glyceryl | phenyl | phenyl 1-O-octadecyl-2-O-benzyl-sn glyceryl 9-(S)-[(3-methoxy-2-phosphonomethoxy)propyl]2,6-diaminopurine |
| 181 | guanin-9-yl | octadecyloxyethyl | ethyl | ethyl octadecyloxyethyl 9-(S)-[(3-methoxy-2-phosphonomethoxy)propyl]guanine |
| 182 | adenine-9-yl | octadecyloxyethyl | ethyl | ethyl octadecyloxyethyl 9-(S)-[(3-methoxy-2-phosphonomethoxy)propyl]adenine |
| 183 | cytosine-1-yl | octadecyloxyethyl | ethyl | ethyl octadecyloxyethyl 1-(S)-[(3-methoxy-2-phosphonomethoxy)propyl]cytosine |
| 184 | thymin-1-yl | octadecyloxyethyl | ethyl | ethyl octadecyloxyethyl 1-(S)-[(3-methoxy-2-phosphonomethoxy)propyl]thymine |
| 185 | uracil-1-yl | octadecyloxyethyl | ethyl | ethyl octadecyloxyethyl 1-(S)-[(3-methoxy-2-phosphonomethoxy)propyl]uracil |

TABLE 3-continued (S)-3-methoxy-2-phosphonmethoxypropyl [(S)-MPMP] diester compounds Rp or Sp (depends on substituents)          Rp, Sp (racemic)

| Cmpd No. | $B_{Nuc}/B_{Nuc(a)}$ | L/L$^a$ | R/R$^a$ | Name |
| --- | --- | --- | --- | --- |
| 186 | 2,6-diaminopurin-9-yl | octadecyloxyethyl | ethyl | ethyl octadecyloxyethyl 9-(S)-[(3-methoxy-2-phosphonomethoxy)propyl]2,6-diaminopurine |
| 187 | guanin-9-yl | hexadecyloxypropyl | ethyl | ethyl hexadecyloxypropyl 9-(S)-[(3-methoxy-2-phosphonomethoxy)propyl]guanine |
| 188 | adenine-9-yl | hexadecyloxypropyl | ethyl | ethyl hexadecyloxypropyl 9-(S)-[(3-methoxy-2-phosphonomethoxy)propyl]adenine |
| 189 | cytosine-1-yl | hexadecyloxypropyl | ethyl | ethyl hexadecyloxypropyl 1-(S)-[(3-methoxy-2-phosphonomethoxy)propyl]cytosine |
| 190 | thymin-1-yl | hexadecyloxypropyl | ethyl | ethyl hexadecyloxypropyl 1-(S)-[(3-methoxy-2-phosphonomethoxy)propyl]thymine |
| 191 | uracil-1-yl | hexadecyloxypropyl | ethyl | ethyl hexadecyloxypropyl 1-(S)-[(3-methoxy-2-phosphonomethoxy)propyl]uracil |
| 192 | 2,6-diaminopurin-9-yl | hexadecyloxypropyl | ethyl | ethyl hexadecyloxypropyl 9-(S)-[(3-methoxy-2-phosphonomethoxy)propyl]2,6-diaminopurine |
| 193 | guanin-9-yl | 1-O-octadecyl-2-O-benzyl-sn glyceryl | ethyl | ethyl 1-O-octadecyl-2-O-benzyl-sn glyceryl 9-(S)-[(3-methoxy-2-phosphonomethoxy)propyl]guanine |
| 194 | adenine-9-yl | 1-O-octadecyl-2-O-benzyl-sn glyceryl | ethyl | ethyl 1-O-octadecyl-2-O-benzyl-sn glyceryl 9-(S)-[(3-methoxy-2-phosphonomethoxy)propyl]adenine |
| 195 | cytosine-1-yl | 1-O-octadecyl-2-O-benzyl-sn glyceryl | ethyl | ethyl 1-O-octadecyl-2-O-benzyl-sn glyceryl 1-(S)-[(3-methoxy-2-phosphonomethoxy)propyl]cytosine |
| 196 | thymin-1-yl | 1-O-octadecyl-2-O-benzyl-sn glyceryl | ethyl | ethyl 1-O-octadecyl-2-O-benzyl-sn glyceryl 1-(S)-[(3-methoxy-2-phosphonomethoxy)propyl]thymine |
| 197 | uracil-1-yl | 1-O-octadecyl-2-O-benzyl-sn glyceryl | ethyl | ethyl 1-O-octadecyl-2-O-benzyl-sn glyceryl 1-(S)-[(3-methoxy-2-phosphonomethoxy)propyl]uracil |
| 198 | 2,6-diaminopurin-9-yl | 1-O-octadecyl-2-O-benzyl-sn glyceryl | ethyl | phenyl 1-O-octadecyl-2-O-benzyl-sn glyceryl 9-(S)-[(3-methoxy-2-phosphonomethoxy)propyl]2,6-diaminopurine |
| 199 | guanin-9-yl | octadecyloxyethyl | galactosyl | galactosyl octadecyloxyethyl 9-(S)-[(3-methoxy-2-phosphonomethoxy)propyl]guanine |
| 200 | adenine-9-yl | octadecyloxyethyl | galactosyl | galactosyl octadecyloxyethyl 9-(S)-[(3-methoxy-2-phosphonomethoxy)propyl]adenine |
| 201 | cytosine-1-yl | octadecyloxyethyl | galactosyl | galactosyl octadecyloxyethyl 1-(S)-[(3-methoxy-2-phosphonomethoxy)propyl]cytosine |
| 202 | thymin-1-yl | octadecyloxyethyl | galactosyl | galactosyl octadecyloxyethyl 1-(S)-[(3-methoxy-2-phosphonomethoxy)propyl]thymine |
| 203 | uracil-1-yl | octadecyloxyethyl | galactosyl | galactosyl octadecyloxyethyl 1-(S)-[(3-methoxy-2-phosphonomethoxy)propyl]uracil |
| 204 | 2,6-diaminopurin-9-yl | octadecyloxyethyl | galactosyl | galactosyl octadecyloxyethyl 9-(S)-[(3-methoxy-2-phosphonomethoxy)propyl]2,6-diaminopurine |
| 205 | guanin-9-yl | hexadecyloxypropyl | galactosyl | galactosyl hexadecyloxypropyl 9-(S)-[(3-methoxy-2-phosphonomethoxy)propyl]guanine |

TABLE 3-continued

(S)-3-methoxy-2-phosphonmethoxypropyl [(S)-MPMP] diester compounds

Rp or Sp (depends on substituents)     Rp, Sp (racemic)

| Cmpd No. | B_{Nuc}/B_{Nuc(a)} | L/L^a | R/R^a | Name |
|---|---|---|---|---|
| 206 | adenine-9-yl | hexadecyloxypropyl | galactosyl | galactosyl hexadecyloxypropyl 9-(S)-[(3-methoxy-2-phosphonomethoxy)propyl]adenine |
| 207 | cytosine-1-yl | hexadecyloxypropyl | galactosyl | galactosyl hexadecyloxypropyl 1-(S)-(3-methoxy-2-phosphonomethoxy)propyl]cytosine |
| 208 | thymin-1-yl | hexadecyloxypropyl | galactosyl | galactosyl hexadecyloxypropyl 1-(S)-[(3-methoxy-2-phosphonomethoxy)propyl]thymine |
| 209 | uracil-1-yl | hexadecyloxypropyl | galactosyl | galactosyl hexadecyloxypropyl 1-(S)-[(3-methoxy-2-phosphonomethoxy)propyl]uracil |
| 210 | 2,6-diaminopurin-9-yl | hexadecyloxypropyl | galactosyl | galactosyl hexadecyloxypropyl 9-(S)-[(3-methoxy-2-phosphonomethoxy)propyl]2,6-diaminopurine |
| 211 | guanin-9-yl | 1-O-octadecyl-2-O-benzyl-sn glyceryl | galactosyl | galactosyl 1-O-octadecyl-2-O-benzyl-sn glyceryl 9-(S)-[(3-methoxy-2-phosphonomethoxy)propyl]guanine |
| 212 | adenine-9-yl | 1-O-octadecyl-2-O-benzyl-sn glyceryl | galactosyl | galactosyl 1-O-octadecyl-2-O-benzyl-sn glyceryl 9-(S)-[(3-methoxy-2-phosphonomethoxy)propyl]adenine |
| 213 | cytosine-1-yl | 1-O-octadecyl-2-O-benzyl-sn glyceryl | galactosyl | galactosyl 1-O-octadecyl-2-O-benzyl-sn glyceryl 1-(S)-[(3-methoxy-2-phosphonomethoxy)propyl]cytosine |
| 214 | thymin-1-yl | 1-O-octadecyl-2-O-benzyl-sn glyceryl | galactosyl | galactosyl 1-O-octadecyl-2-O-benzyl-sn glyceryl 1-(S)-[(3-methoxy-2-phosphonomethoxy)propyl]thymine |
| 215 | uracil-1-yl | 1-O-octadecyl-2-O-benzyl-sn glyceryl | galactosyl | galactosyl 1-O-octadecyl-2-O-benzyl-sn glyceryl 1-(S)-[(3-methoxy-2-phosphonomethoxy)propyl]uracil |
| 216 | 2,6-diaminopurin-9-yl | 1-O-octadecyl-2-O-benzyl-sn glyceryl | galactosyl | galactosyl 1-O-octadecyl-2-O-benzyl-sn glyceryl 9-(S)-[(3-methoxy-2-phosphonomethoxy)propyl]2,6-diaminopurine |

TABLE 4

(S)-3-hydroxy-2-phosphonomethoxypropyl [(S)-HPMP] diester compounds

Rp or Sp (depends on substituents)     Rp, Sp (racemic)

| Cmpd No. | B_{nuc}/B_{Nac(a)} | L/L^a | R/R^a | Name |
|---|---|---|---|---|
| 217 | guanin-9-yl | octadecyloxyethyl | benzyl | benzyl octadecyloxyethyl 9-(S)-[(3-hydroxy-2-phosphonomethoxy)propyl]guanine |
| 218 | adenine-9-yl | octadecyloxyethyl | benzyl | benzyl octadecyloxyethyl 9-(S)-[(3-hydroxy-2-phosphonomethoxy)propyl]adenine |
| 219 | cytosine-1-yl | octadecyloxyethyl | benzyl | benzyl octadecyloxyethyl 1-(S)-[(3-hydroxy-2-phosphonomethoxy)propyl]cytosine |

TABLE 4-continued (S)-3-hydroxy-2-phosphonomethoxypropyl [(S)-HPMP] diester compounds Rp or Sp (depends on substituents)    Rp, Sp (racemic)

| Cmpd No. | $B_{nuc}/B_{Nac(a)}$ | L/L$^a$ | R/R$^a$ | Name |
|---|---|---|---|---|
| 220 | thymin-1-yl | octadecyloxyethyl | benzyl | benzyl octadecyloxyethyl 1-(S)-[(3-hydroxy-2-phosphonomethoxy)propyl]thymine |
| 221 | uracil-1-yl | octadecyloxyethyl | benzyl | benzyl octadecyloxyethyl 1-(S)-[3-hydroxy-2-phosphonomethoxy)propyl]uracil |
| 222 | 2,6-diaminopurin-9-yl | octadecyloxyethyl | benzyl | benzyl octadecyloxyethyl 9-(S)-[(3-hydroxy-2-phosphonomethoxy)propyl]2,6-diaminopurine |
| 223 | guanin-9-yl | hexadecyloxypropyl | benzyl | benzyl hexadecyloxypropyl-9-(S)-[(3-hydroxy-2-phosphonomethoxy)propyl]guanine |
| 224 | adenine-9-yl | hexadecyloxypropyl | benzyl | benzyl hexadecyloxypropyl 9-(S)-[(3-hydroxy-2-phosphonomethoxy)propyl]adenine |
| 225 | cytosine-1-yl | hexadecyloxypropyl | benzyl | benzyl hexadecyloxypropyl 1-(S)-[(3-hydroxy-2-phosphonomethoxy)propyl]cytosine |
| 226 | thymin-1-yl | hexadecyloxypropyl | benzyl | benzyl hexadecyloxypropyl 1-(S)-[(3-hydroxy-2-phosphonomethoxy)propyl]thymine |
| 227 | uracil-1-yl | hexadecyloxypropyl | benzyl | benzyl hexadecyloxypropyl 1-(S)-[(3-hydroxy-2-phosphonomethoxy)propyl]uracil |
| 228 | 2,6-diaminopurin-9-yl | hexadecyloxypropyl | benzyl | benzyl hexadecyloxypropyl 9-(S)-[(3-hydroxy-2-phosphonomethoxy)propyl]2,6-diaminopurine |
| 229 | guanin-9-yl | 1-O-octadecyl-2-O-benzyl-sn glyceryl | benzyl | benzyl 1-O-octadecyl-2-O-benzyl-sn glyceryl 9-(S)-[(3-hydroxy-2-phosphonomethoxy)propyl]guanine |
| 230 | adenine-9-yl | 1-O-octadecyl-2-O-benzyl-sn glyceryl | benzyl | benzyl 1-O-octadecyl-2-O-benzyl-sn glyceryl 9-(S)-[(3-hydroxy-2-phosphonomethoxy)propyl]adenine |
| 231 | cytosine-1-yl | 1-O-octadecyl-2-O-benzyl-sn glyceryl | benzyl | benzyl 1-O-octadecyl-2-O-benzyl-sn glyceryl 1-(S)-[(3-hydroxy-2-phosphonomethoxy)propyl]cytosine |
| 232 | thymin-1-yl | 1-O-octadecyl-2-O-benzyl-sn glyceryl | benzyl | benzyl 1-O-octadecyl-2-O-benzyl-sn glyceryl 1-(S)-[(3-hydroxy-2-phosphonomethoxy)propyl]thymine |
| 233 | uracil-1-yl | 1-O-octadecyl-2-O-benzyl-sn glyceryl | benzyl | benzyl 1-O-octadecyl-2-O-benzyl-sn glyceryl 1-(S)-[(3-hydroxy-2-phosphonomethoxy)propyl]uracil |
| 234 | 2,6-diaminopurin-9-yl | 1-O-octadecyl-2-O-benzyl-sn glyceryl | benzyl | benzyl 1-O-octadecyl-2-O-benzyl-sn glyceryl 9-(S)-[(3-hydroxy-2-phosphonomethoxy)propyl]2,6-diaminopurine |
| 235 | guanin-9-yl | octadecyloxyethyl | phenyl | phenyl octadecyloxyethyl 9-(S)-[(3-hydroxy-2-phosphonomethoxy)propyl]guanine |
| 236 | adenine-9-yl | octadecyloxyethyl | phenyl | phenyl octadecyloxyethyl 9-(S)-[(3-hydroxy-2-phosphonomethoxy)propyl]adenine |
| 237 | cytosine-1-yl | octadecyloxyethyl | phenyl | phenyl octadecyloxyethyl 1-(S)-[(3-hydroxy-2-phosphonomethoxy)propyl]cytosine |
| 238 | thymin-1-yl | octadecyloxyethyl | phenyl | phenyl octadecyloxyethyl 1-(S)-[(3-hydroxy-2-phosphonomethoxy)propyl]thymine |
| 239 | uracil-1-yl | octadecyloxyethyl | phenyl | phenyl octadecyloethyl 1-(S)-[(3-hydroxy-2-phosphonomethoxy)propyl]uracil |

TABLE 4-continued (S)-3-hydroxy-2-phosphonomethoxypropyl [(S)-HPMP] diester compounds $B_{Nuc}/B_{Nuc(a)}$ — structures shown — P(=O)(O—L/L$^a$)(O—R/R$^a$)

Rp or Sp (depends on substituents)    Rp, Sp (racemic)

| Cmpd No. | $B_{nuc}/B_{Nac(a)}$ | L/L$^a$ | R/R$^a$ | Name |
|---|---|---|---|---|
| 240 | 2,6-diaminopurin-9-yl | octadecyloxyethyl | phenyl | phenyl octadecyloxyethyl 9-(S)-[(3-hydroxy-2-phosphonomethoxy)propyl]2,6-diaminopurine |
| 241 | guanin-9-yl | hexadecyloxypropyl | phenyl | phenyl hexadecyloxypropyl 9-(S)-[(3-hydroxy-2-phosphonomethoxy)propyl]guanine |
| 242 | adenini-9-yl | hexadecyloxypropyl | phenyl | phenyl hexadecyloxypropyl 9-(S)-[(3-hydroxy-2-phosphonomethoxy)propyl]adenine |
| 243 | cytosine-1-yl | hexadecyloxypropyl | phenyl | phenyl hexadecyloxypropyl 1-(S)-[(3-hydroxy-2-phosphonomethoxy)propyl]cytosine |
| 244 | thymin-1-yl | hexadecyloxypropyl | phenyl | phenyl hexadecyloxypropyl 1-(S)-[(3-hydroxy-2-phosphonomethoxy)propyl]thymine |
| 245 | uracil-1-yl | hexadecyloxypropyl | phenyl | phenyl hexadecyloxypropyl 1-(S)-[(3-hydroxy-2-phosphonomethoxy)propyl]uracil |
| 246 | 2,6-diaminopurin-9-yl | hexadecyloxypropyl | phenyl | phenyl hexadecyloxypropyl 9-(S)-[(3-hydroxy-2-phosphonomethoxy)propyl]2,6-diaminopurine |
| 247 | guanin-9-yl | 1-O-octadecyl-2-O-benzyl-sn glyceryl | phenyl | phenyl 1-O-octadecyl-2-O-benzyl-sn glyceryl 9-(S)-[(3-hydroxy-2-phosphonomethoxy)propyl]guanine |
| 248 | adenine-9-yl | 1-O-octadecyl-2-O-benzyl-sn glyceryl | phenyl | phenyl 1-O-octadecyl-2-O-benzyl-sn glyceryl 9-(S)-[(3-hydroxy-2-phosphonomethoxy)propyl]adenine |
| 249 | cytosine-1-yl | 1-O-octadecyl-2-O-benzyl-sn glyceryl | phenyl | phenyl 1-O-octadecyl-2-O-benzyl-sn glyceryl 1-(S)-[(3-hydroxy-2-phosphonomethoxy)propyl]cytosine |
| 250 | thymin-1-yl | 1-O-octadecyl-2-O-benzyl-sn glyceryl | phenyl | phenyl 1-O-octadecyl-2-O-benzyl-sn glyceryl 1-(S)-[(3-hydroxy-2-phosphonomethoxy)propyl]thymine |
| 251 | uracil-1-yl | 1-O-octadecyl-2-O-benzyl-sn glyceryl | phenyl | phenyl 1-O-octadecyl-2-O-benzyl-sn glyceryl 1-(S)-[(3-hydroxy-2-phosphonomethoxy)propyl]uracil |
| 252 | 2,6-diaminopurin-9-yl | 1-O-octadecyl-2-O-benzyl-sn glyceryl | phenyl | phenyl 1-O-octadecyl-2-O-benzyl-sn glyceryl 9-(S)-[(3-hydroxy-2-phosphonomethoxy)propyl]2,6-diaminopurine |
| 253 | guanin-9-yl | octadecyloxyethyl | ethyl | ethyl octadecyloxyethyl 9-(S)-[(3-hydroxy-2-phosphonomethoxy)propyl]guanine |
| 254 | adenine-9-yl | octadecyloxyethyl | ethyl | ethyl octadecyloxyethyl 9-(S)-[(3-hydroxy-2-phosphonomethoxy)propyl]adenine |
| 255 | cytosine-1-yl | octadecyloxyethyl | ethyl | ethyl octadecyloxyethyl 1-(S)-[(3-hydroxy-2-phosphonomethoxy)propyl]cytosine |
| 256 | thymin-1-yl | octadecyloxyethyl | ethyl | ethyl octadecyloxyethyl 1-(S)-[(3-hydroxy-2-phosphonomethoxy)propyl]thymine |
| 257 | uracil-1-yl | octadecyloxyethyl | ethyl | ethyl octadecyloxyethyl 1-(S)-[(3-hydroxy-2-phosphonomethoxy)propyl]uracil |
| 258 | 2,6-diaminopurin-9-yl | octadecyloethyl | ethyl | ethyl octadecyloxyethyl 9-(S)-[(3-hydroxy-2-phosphonomethoxy)propyl]2,6-diaminopurine |
| 259 | guanin-9-yl | hexadecyloxypropyl | ethyl | ethyl hexadecyloxypropyl 9-(S)-[(3-hydroxy-2-phosphonomethoxy)propyl]guanine |

TABLE 4-continued (S)-3-hydroxy-2-phosphonomethoxypropyl [(S)-HPMP] diester compounds Rp or Sp (depends on substituents) or Rp, Sp (racemic)

| Cmpd No. | $B_{nuc}/B_{Nac(a)}$ | L/L$^a$ | R/R$^a$ | Name |
|---|---|---|---|---|
| 260 | adenine-9-yl | hexadecyloxypropyl | ethyl | ethyl hexadecyloxypropyl 9-(S)-[(3-hydroxy-2-phosphonomethoxy)propyl]adenine |
| 261 | cytosine-1-yl | hexadecyloxypropyl | ethyl | ethyl hexadecyloxypropyl 1-(S)-[(3-hydroxy-2-phosphonomethoxy)propyl]cytosine |
| 262 | thymin-1-yl | hexadecyloxypropyl | ethyl | ethyl hexadecyloxypropyl 1-(S)-[(3-hydroxy-2-phosphonomethoxy)propyl]thymine |
| 263 | uracil-1-yl | hexadecyloxypropyl | ethyl | ethyl hexadecyloxypropyl 1-(S)-[(3-hydroxy-2-phosphonomethoxy)propyl]uracil |
| 264 | 2,6-diaminopurin-9-yl | hexadecyloxypropyl | ethyl | ethyl hexadecyloxypropyl 9-(S)-[(3-hydroxy-2-phosphonomethoxy)propyl]2,6-diaminopurine |
| 265 | guanin-9-yl | 1-O-octadecyl-2-O-benzyl-sn glyceryl | ethyl | ethyl 1-O-octadecyl-2-O-benzyl-sn glyceryl 9-(S)-[(3-hydroxy-2-phosphonomethoxy)propyl]guanine |
| 266 | adenine-9-yl | 1-O-octadecyl-2-O-benzyl-sn glyceryl | ethyl | ethyl 1-O-octadecyl-2-O-benzyl-sn glyceryl 9-(S)-[(3-hydroxy-2-phosphonomethoxy)propyl]adenine |
| 267 | cytosine-1-yl | 1-O-octadecyl-2-O-benzyl-sn glyceryl | ethyl | ethyl 1-O-octadecyl-2-O-benzyl-sn glyceryl 1-(S)-[(3-hydroxy-2-phosphonomethoxy)propyl]cytosine |
| 268 | thymin-1-yl | 1-O-octadecyl-2-O-benzyl-sn glyceryl | ethyl | ethyl 1-O-octadecyl-2-O-benzyl-sn glyceryl 1-(S)-[(3-hydroxy-2-phosphonomethoxy)propyl]thymine |
| 269 | uracil-1-yl | 1-O-octadecyl-2-O-benzyl-sn glyceryl | ethyl | ethyl 1-O-octadecyl-2-O-benzyl-sn glyceryl 1-(S)-[(3-hydroxy-2-phosphonomethoxy)propyl]uracil |
| 270 | 2,6-diaminopurin-9-yl | 1-O-octadecyl-2-O-benzyl-sn glyceryl | ethyl | phenyl 1-O-octadecyl-2-O-benzyl-sn glyceryl 9-(S)-[(3-hydroxy-2-phosphonomethoxy)propyl]2,6-diaminopurine |
| 271 | guanin-9-yl | octadecyloxyethyl | galactosyl | galactosyl octadecyloxyethyl 9-(S)-[(3-hydroxy-2-phosphonomethoxy)propyl]guanine |
| 272 | adenine-9-yl | octadecyloethyl | galactosyl | galactosyl octadecyloxyethyl 9-(S)-[(3-hydroxy-2-phosphonomethoxy)propyl]adenine |
| 273 | cytosine-1-yl | octadecyloxyethyl | galactosyl | galactosyl octadecyloxyethyl 1-(S)-[(3-hydrox-2-phosphonomethoxy)propyl]cytosine |
| 274 | thymin-1-yl | octadecyloxyethyl | galactosyl | galactosyl octadecyloxyethyl 1-(S)-[(3-hydroxy-2-phosphonomethoxy)propyl]thymine |
| 275 | uracil-1-yl | octadecyloxyethyl | galactosyl | galactosyl octadecyloxyethyl 1-(S)-[(3-hydroxy-2-phosphonomethoxy)propyl]uracil |
| 276 | 2,6-diaminopurin-9-yl | octadecyloxyethyl | galactosyl | galactosyl octadecyloxyethyl 9-(S)-[(3-hydroxy-2-phosphonomethoxy)propyl]2,6-diaminopurine |
| 277 | guanin-9-yl | hexadecyloxypropyl | galactosyl | galactosyl hexadecyloxypropyl 9-(S)-[(3-hydroxy-2-phosphonomethoxy)propyl]guanine |
| 278 | adenine-9-yl | hexadecyloxypropyl | galactosyl | galactosyl hexadecyloxypropyl 9-(S)-[(3-hydroxy-2-phosphonomethoxy)propyl]adenine |
| 279 | cytosine-1-yl | hexadecyloxypropyl | galactosyl | galactosyl hexadecyloxypropyl 1-(S)-[(3-hydroxy-2-phosphonomethoxy)propyl]cytosine |

TABLE 4-continued (S)-3-hydroxy-2-phosphonomethoxypropyl [(S)-HPMP] diester compounds Rp or Sp (depends on substituents)        Rp, Sp (racemic)

| Cmpd No. | $B_{Nuc}/B_{Nac(a)}$ | $L/L^a$ | $R/R^a$ | Name |
|---|---|---|---|---|
| 280 | thymin-1-yl | hexadecyloxypropyl | galactosyl | galactosyl hexadecyloxypropyl 1-(S)-[(3-hydroxy-2-phosphonomethoxy)propyl]thymine |
| 281 | uracil-1-yl | hexadecyloxypropyl | galactosyl | galactosyl hexadecyloxypropyl 1-(S)-[(3-hydroxy-2-phosphonomethoxy)propyl]uracil |
| 282 | 2,6-diaminopurin-9-yl | hexadecyloxypropyl | galactosyl | galactosyl hexadecyloxypropyl 9-(S)-[(3-hydroxy-2-phosphonomethoxy)propyl]2,6-diaminopurine |
| 283 | guanin-9-yl | 1-O-octadecyl-2-O-benzyl-sn glyceryl | galactosyl | galactosyl 1-O-octadecyl-2-O-benzyl-sn glyceryl 9-(S)-[(3-hydroxy-2-phosphonomethoxy)propyl]guanine |
| 284 | adenine-9-yl | 1-O-octadecyl-2-O-benzyl-sn glyceryl | galactosyl | galactosyl 1-O-octadecyl-2-O-benzyl-sn glyceryl 9-(S)-[(3-hydroxy-2-phosphonomethoxy)propyl]adenine |
| 285 | cytosine | 1-O-ctadecyl-2-O-benzyl-sn glyceryl | galactosyl | galactosyl 1-O-octadecyl-2-O-benzyl sn glyceryl 1-(S)-[(3-hydroxy-2-phosphonomethoxy)propyl]cytosine |
| 286 | thymine-1-yl | 1-O-ctadecyl-2-O-benzyl-sn glyceryl | galactosyl | galactosyl 1-O-octadecyl-2-O-benzyl sn glyceryl 1-(S)-[(3-hydroxy-2-phosphonomethoxy)porpyl]thymine |
| 287 | uracil-1-yl | 1-O-octadecyl-2-O-benzyl-sn glyceryl | galactosyl | galactosyl 1-O-octadecyl-2-O-benzyl sn glyceryl 1-(S)-[(3-hydroxy-2-phosphonomethoxy)propyl]uracil |
| 288 | 2,6-diaminopurin-9-yl | 1-O-octadecyl-2-O-benzyl-sn glyceryl | galactosyl | galactosyl 1-O-octadecyl-2-O-benzyl sn glyceryl 9-(S)-[(3-hydroxy-2-phosphonomethoxy)propyl]2,6-diaminopurine |

TABLE 5

(S)-3-fluoro-2-phosphonomethoxypropyl [(S)-FPMP] diester compounds

Rp or Sp (depends on substituents)        Rp, Sp (racemic)

| Cmpd No. | $B_{Nuc}/B_{Nac(a)}$ | $L/L^a$ | $R/R^a$ | Name |
|---|---|---|---|---|
| 289 | guanin-9-yl | octadecyloxyethyl | benzyl | benzyl octadecyloxyethyl 9-(S)-[(3-fluoro-2-phosphonomethoxy)propyl]guanine |
| 290 | adenine-9-yl | octadecyloxyethyl | benzyl | benzyl octadecyloxyethyl 9-(S)-[(3-fluoro-2-phosphonomethoxy)propyl]adenine |
| 291 | cytosine-1-yl | octadecyloxyethyl | benzyl | benzyl octadecyloxyethyl 1-(S)-[(3-fluoro-2-phosphonomethoxy)propyl]cytosine |
| 292 | thymin-1-yl | octadecyloxyethyl | benzyl | benzyl octadecyloxyethyl 1-(S)-[(3-fluor-2-phosphonomethoxy)propyl]thymine |

TABLE 5-continued (S)-3-fluoro-2-phosphonomethoxypropyl [(S)-FPMP] diester compounds

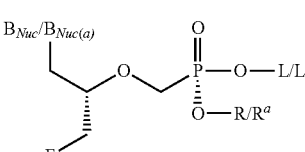

Rp or Sp (depends on substituents)        Rp, Sp (racemic)

| Cmpd No. | $B_{Nuc}/B_{Nac(a)}$ | $L/L^a$ | $R/R^a$ | Name |
|---|---|---|---|---|
| 293 | uracil-1-yl | octadecyloxyethyl | benzyl | benzyl octadecyloxyethyl 1-(S)-[(3-fluoro-2-phosphonomethoxy)propyl]uracil |
| 294 | 2,6-diaminopurin-9-yl | octadecyloxyethyl | benzyl | benzyl octadecyloxyethyl 9-(S)-[(3-lfuoro-2-phosphonomethoxy)propyl]2,6-diaminopurine |
| 295 | guanin-9-yl | hexadecyloxypropyl | benzyl | benzyl hexadecyloxypropyl 9-(S)-[(3-fluoro-2-phosphonomethoxy)propyl]guanine |
| 296 | adenine-9-yl | hexadecyloxypropyl | benzyl | benzyl hexadecyloxypropyl 9-(S)-[(3-fluoro-2-phosphonomethoxy)propyl]adenine |
| 297 | cytosine-1-yl | hexadecyloxypropyl | benzyl | benzyl hexadecyloxypropyl 1-(S)-[(3-fluoro-2-phosphonomethoxy)propyl]cytosine |
| 298 | thymin-1-yl | hexadecyloxypropyl | benzyl | benzyl hexadecyloxypropyl 1-(S)-[(3-fluoro-2-phosphonomethoxy)propyl]thymine |
| 299 | uracil-1-yl | hexadecyloxypropyl | benzyl | benzyl hexadecyloxypropyl 1-(S)-[(3-fluoro-2-phosphonomethoxy)propyl]uracil |
| 300 | 2,6-diaminopurin-9-yl | hexadecyloxypropyl | benzyl | benzyl hexadecyloxypropyl 9-(S)-[(3-fluoro-2-phosphonomethoxy)propyl]2,6-diaminopurine |
| 301 | guanin-9-yl | 1-O-octadecyl-2-O-benzyl-sn glyceryl | benzyl | benzyl 1-O-octadecyl-2-O-benzyl-sn glyceryl 9-(S)-[(3-fluoro-2-phosphonomethoxy)porpyl]guanine |
| 302 | adenine-9-yl | 1-O-octadecyl-2-O-benzyl-sn glyceryl | benzyl | benzyl 1-O-octadecyl-2-O-benzyl-sn glyceryl 9-(S)-[(3-fluoro-2-phosphonomethoxy)propyl]adenine |
| 303 | cytosine-1-yl | 1-O-octadecyl-2-O-benzyl-sn glyceryl | benzyl | benzyl 1-O-octadecyl-2-O-benzyl-sn glyceryl 1-(S)-[(3-fluoro-2-phosphonomethoxy)propyl]cytosine |
| 304 | thymin-1-yl | 1-O-octadecyl-2-O-benzyl-sn glyceryl | benzyl | benzyl 1-O-octadecyl-2-O-benzyl-sn glyceryl 1-(S)-[(3-fluoro-2-phosphonomethoxy)propyl]thymine |
| 305 | uracil-1-yl | 1-O-octadecyl-2-O-benzyl-sn glyceryl | benzyl | benzyl 1-O-octadecyl-2-O-benzyl-sn glyceryl 1-(S)-[(3-fluoro-2-phosphonomethoxy)propyl]uracil |
| 306 | 2,6-diaminopurin-9-yl | 1-O-octadecyl-2-O-benzyl-sn glyceryl | benzyl | benzyl 1-O-octadecyl-2-O-benzyl-sn glyceryl 9-(S)-[(3-fluoro-2-phosphonomethoxy)propyl]2,6-diaminopurine |
| 307 | guanin-9-yl | octadecyloxyethyl | phenyl | phenyl octadecyloxyethyl 9-(S)-[(3-fluoro-2-phosphonomethoxy)propyl]guanine |
| 308 | adenine-3-yl | octadecyloxyethyl | phenyl | phenyl octadecyloxyethyl 9-(S)-[(3-fluoro-2-phosphonomethoxy)propyl]adenine |
| 309 | cytosine-1-yl | octadecyloxyethyl | phenyl | phenyl octadecyloxyethyl 1-(S)-[(3-fluoro-2-phosphonomethoxy)propyl]cytosine |
| 310 | thymin-1-yl | octadecyloxyethyl | phenyl | phenyl octadecyloxyethyl 1-(S)-[(3-fluoro-2-phosphonomethoxy)propyl]thymine |
| 311 | uracil-1-yl | octadecyloxyethyl | phenyl | phenyl octadecyloxyethyl 1-(S)-[(3-fluoro-2-phosphonomethoxy)propyl]uracil |
| 312 | 2,6-diaminopurin-9-yl | octadecyloxyethyl | phenyl | phenyl octadecyloxyethyl 9-(S)-[(3-fluoro-2-phosphonomethoxy)propyl]2,6-dimainopurine |

TABLE 5-continued (S)-3-fluoro-2-phosphonomethoxypropyl [(S)-FPMP] diester compounds Rp or Sp (depends on substituents)    Rp, Sp (racemic)

| Cmpd No. | B$_{Nuc}$/B$_{Nac(a)}$ | L/L$^a$ | R/R$^a$ | Name |
|---|---|---|---|---|
| 313 | guanin-9-yl | hexadecyloxypropyl | phenyl | phenyl hexadecyloxypropyl 9-(S)-[(3-fluoro-2-phosphonomethoxy)propyl]guanine |
| 314 | adenine-9-yl | hexadecyloxypropyl | phenyl | phenyl hexadecyloxypropyl 9-(S)-[(3-fluoro-2-phosphonomethoxy)propyl]adenine |
| 315 | cytosine-1-yl | hexadecyloxyporpyl | phenyl | phenyl hexadecyloxypropyl 1-(S)-[(3-fluoro-2-phosphonomethoxy)propyl]cytosine |
| 316 | thymin-1-yl | hexadecyloxypropyl | phenyl | phenyl hexadecyloxypropyl 1-(S)-[(3-fluoro-2-phosphonomethoxy)propyl]thymine |
| 317 | uracil-1-yl | hexadecyloxypropyl | phenyl | phenyl hexadecyloxypropyl 1-(S)-[(3-fluoro-2-phosphonomethoxy)propyl]uracil |
| 318 | 2,6-diaminopurin-9-yl | hexadecyloxypropyl | phenyl | phenyl hexadecyloxypropyl 9-(S)-[(3-fluoro-2-phosphonomethoxy)propyl]2,6-diaminopurine |
| 319 | guanin-9-yl | 1-O-octadecyl-2-O-benzyl-sn glyceryl | phenyl | phenyl 1-O-octadecyl-2-O-benzyl-sn glyceryl 9-(S)-[(3-fluoro-2-phosphonomethoxy)propyl]guanine |
| 320 | adenine-9-yl | 1-O-octadecyl-2-O-benzyl-sn glyceryl | phenyl | phenyl 1-O-octadecyl-2-O-benzyl-sn glyceryl 9-(S)-[(3-fluoro-2-phosphonomethoxy)propyl]adenine |
| 321 | cytosine-1-yl | 1-O-octadecyl-2-O-benzyl-sn glyceryl | phenyl | phenyl 1-O-octadecyl-2-O-benzyl-sn glyceryl 1-(S)-[(3-fluoro-2-phosphonomethoxy)propyl]cytosine |
| 322 | thymin-1-yl | 1-O-octadecyl-2-O-benzyl-sn glyceryl | phenyl | phenyl 1-O-octadecyl-2-O-benzyl-sn glyceryl 1-(S)-[(3-fluoro-2-phosphonomethoxy)propyl]thymine |
| 323 | uracil-1-yl | 1-O-octadecyl-2-O-benzyl-sn glyceryl | phenyl | phenyl 1-O-octadecyl-2-O-benzyl-sn glyceryl 1-(S)-[(3-fluoro-2-phosphonomethoxy)propyl]uracil |
| 324 | 2,6-diaminopurin-9-yl | 1-O-octadecyl-2-O-benzyl-sn glyceryl | phenyl | phenyl 1-O-octadecyl-2-O-benzyl-sn glyceryl 9-(S)-[(3-fluoro-2-phosphonomethoxy)propyl]2,6-diaminopurine |
| 325 | guanin-9-yl | octadecyloxyethyl | ethyl | ethyl octadecyloxyethyl 9-(S)-[(3-fluoro-2-phosphonomethoxy)propyl]guanine |
| 326 | adenine-9-yl | octadecyloxyethyl | ethyl | ethyl octadecyloxyethyl 9-(S)-[(3-fluoro-2-phosphonomethoxy)propyl]adenine |
| 327 | cytosine-1-yl | octadecyloxyethyl | ethyl | ethyl octadecyloxyethyl 1-(S)-[(3-fluoro-2-phosphonomethoxy)propyl]cytosine |
| 328 | thymin-1-yl | octadecyloxyethyl | ethyl | ethyl octadecyloxyethyl 1-(S)-[(3-fluoro-2-phosphonomethoxy)propyl]thymine |
| 329 | uracil-1-yl | octadecyloxyethyl | ethyl | ethyl octadecyloxyethyl 1-(S)-[(3-fluoro-2-phosphonomethoxy)propyl]uracil |
| 330 | 2,6-diaminopurin-9-yl | octadecyloxyethyl | ethyl | ethyl octadecyloxyethyl 9-(S)-[(3-fluoro-2-phosphonomethoxy)propyl]2,6-diaminopurine |
| 331 | guanin-9-yl | hexadecyloxypropyl | ethyl | ethyl hexadecyloxypropyl 9-(S)-[(3-fluoro-2-phosphonomethoxy)propyl]guanine |
| 332 | adenine-9-yl | hexadecyloxypropyl | ethyl | ethyl hexadecyloxypropyl 9-(S)-[(3-fluoro-2-phosphonomethoxy)propyl]adenine |

TABLE 5-continued (S)-3-fluoro-2-phosphonomethoxypropyl [(S)-FPMP] diester compounds

| Cmpd No. | $B_{Nuc}/B_{Nac(a)}$ | $L/L^a$ | $R/R^a$ | Name |
|---|---|---|---|---|
| 333 | cytosine-1-yl | hexadecyloxypropyl | ethyl | ethyl hexadecyloxypropyl 1-(S)-[(3-fluoro-2-phosphonomethoxy)propyl]cytosine |
| 334 | thymin-1-yl | hexadecyloxypropyl | ethyl | ethyl hexadecyloxypropyl 1-(S)-[(3-fluoro-2-phosphonomethoxy)propyl]thymine |
| 335 | uracil-1-yl | hexadecyloxypropyl | ethyl | ethyl hexadecyloxypropyl 1-(S)-[(3-fluoro-2-phosphonomethoxy)propyl]uracil |
| 336 | 2,6-diaminopurin-9-yl | hexadecyloxypropyl | ethyl | ethyl hexadecyloxypropyl 9-(S)-[(3-fluoro-2-phosphonomethoxy)propyl]2,6-diaminopurine |
| 337 | guanin-9-yl | 1-O-octadecyl-2-O-benzyl-sn glyceryl | ethyl | ethyl 1-O-octadecyl-2-O-benzyl-sn glyceryl 9-(S)-[(3-fluoro-2-phosphonomethoxy)propyl]guanine |
| 338 | adenine-9-yl | 1-O-octadecyl-2-O-benzyl-sn glyceryl | ethyl | ethyl 1-O-octadecyl-2-O-benzyl-sn glyceryl 9-(S)-[(3-fluoro-2-phosphonomethoxy)propyl]adenine |
| 339 | cytosine-1-yl | 1-O-octadecyl-2-O-benzyl-sn glyceryl | ethyl | ethyl 1-O-octadecyl-2-O-benzyl-sn glyceryl 1-(S)-[(3-fluoro-2-phosphonomethoxy)propyl]cytosine |
| 340 | thymin-1-yl | 1-O-octadecyl-2-O-benzyl-sn glyceryl | ethyl | ethyl 1-O-octadecyl-2-O-benzyl-sn glyceryl 1-(S)-[(3-fluoro-2-phosphonomethoxy)propyl]thymine |
| 341 | uracil-1-yl | 1-O-octadecyl-2-O-benzyl-sn glyceryl | ethyl | ethyl 1-O-octadecyl-2-O-benzyl-sn glyceryl 1-(S)-[(3-fluoro-2-phosphonomethoxy)propyl]uracil |
| 342 | 2,6-diaminopurin-9-yl | 1-O-octadecyl-2-O-benzyl-sn glyceryl | ethyl | phenyl 1-O-octadecyl-2-O-benzyl-sn glyceryl 9-(S)-[(3-fluoro-2-phosphonomethoxy)propyl]2,6-diaminopurine |
| 343 | guanin-9-yl | octadecyloxyethyl | galactosyl | galactosyl octadecyloxyethyl 9-(S)-[(3-fluoro-2-phosphonomethoxy)propyl]guanine |
| 344 | adenine-9-yl | octadecyloxyethyl | galactosyl | galactosyl octadecyloxyethyl 9-(S)-[(3-fluoro-2-phosphonomethoxy)propyl]adenine |
| 345 | cytosine-1-yl | octadecyloxyethyl | galactosyl | galactosyl octadecyloxyethyl 1-(S)-[(3-fluoro-2-phosphonomethoxy)propyl]cytosine |
| 346 | thymin-1-yl | octadecyloxyethyl | galactosyl | galactosyl octadecyloxyethyl 1-(S)-[(3-fluroo-2-phosphonomethoxy)propyl]thymine |
| 347 | uracil-1-yl | octadecyloxyethyl | galactosyl | galactosyl octadecyloxyethyl 1-(S)-[(3-fluoro-2-phosphonomethoxy)propyl]uracil |
| 348 | 2,6-diaminopurin-9-yl | octadecyloxyethyl | galactosyl | galactosyl octadecyloxyethyl 9-(S)-[(3-fluoro-2-phosphonomethoxy)propyl]2,6-diaminopurine |
| 349 | guanin-9-yl | hexadecyloxypropyl | galactosyl | galactosyl hexadecyloxypropyl 9-(S)-[(3-fluoro-2-phosphonomethoxy)propyl]guanine |
| 350 | adenine-9-yl | hexadecyloxypropyl | galactosyl | galactosyl hexadecyloxypropyl 9-(S)--[(3-fluoro-2-phosphonomethoxy)propyl]adenine |
| 351 | cytosine-1-yl | hexadecyloxypropyl | galactosyl | galactosyl hexadecyloxypropyl 1-(S)-[(3-fluoro-2-phosphonomethoxy)propyl]cytosine |
| 352 | thymin-1-yl | hexadecyloxypropyl | galactosyl | galactosyl hexadecyloxypropyl 1-(S)-[(3-fluoro-2-phosphonomethoxy)propyl]thymine |

TABLE 5-continued

(S)-3-fluoro-2-phosphonomethoxypropyl [(S)-FPMP] diester compounds

Rp or Sp (depends on substituents)                                   Rp, Sp (racemic)

| Cmpd No. | $B_{Nuc}/B_{Nac(a)}$ | $L/L^a$ | $R/R^a$ | Name |
|---|---|---|---|---|
| 353 | uracil-1-yl | hexadecyloxypropyl | galactosyl | galactosyl hexadecyloxypropyl 1-(S)-[(3-fluoro-2 phosphomethoxy)propyl]uracil |
| 354 | 2,6-diaminopurin-9-yl | hexadecyloxypropyl | galactosyl | galactosyl hexadecyloxypropyl 9-(S)-[(3-fluoro-2-phosphonomethoxy)propyl]2,6-diaminopurine |
| 355 | guanin-9-yl | 1-O-octadecyl-2-O-benzyl-sn glyceryl | galactosyl | galactosyl 1-O-octadecyl-2-O-benzyl-sn glyceryl 9-(S)-[(3-fluoro-2-phosphonomethoxy)propyl]guanine |
| 356 | adenine-9-yl | 1-O-octadecyl-2-O-benzyl-sn glyceryl | galactosyl | galactosyl 1-O-octadecyl-2-O-beznyl-sn glyceryl 9-(S)-[(3-fluoro-2-phosphonomethoxy)propyl]adenine |
| 357 | cytosine-1-yl | 1-O-octadecyl-2-O-benzyl-sn glyceryl | galactosyl | galactosyl 1-O-octadecyl-2-O-benzyl-sn glyceryl 1-(S)-[(3-fluoro-2-phosphonomethoxy)propyl]cytosine |
| 358 | thymin-1-yl | 1-O-octadecyl-2-O-benzyl-sn glyceryl | galactosyl | galactosyl 1-O-octadecyl-2-benzyl-sn glyceryl 1-(S)-[(3-fluoro-2-phosphonomethoxy)propyl]thymine |
| 359 | uracil-1-yl | 1-O-octadecyl-2-O-benzyl-sn glyceryl | galactosyl | galactosyl 1-O-octadecyl-2-O-benzyl-sn glyceryl 1-(S)-[(3-fluoro-2-phosphonomethoxy)propyl]uracil |
| 360 | 2,6-diaminopurin-9-yl | 1-O-octadecyl-2-O-benzyl-sn glyceryl | galactosyl | galactosyl 1-O-octadecyl-2-O-benzyl-sn glyceryl 9-(S)-[(3-fluoro-2-phosphonomethoxy)propyl]2,6-diaminopurine |

TABLE 6

Phosphonomethoxyethyl (PME) diester compounds

Rp or Sp (depends on substituents)                                   Rp, Sp (racemic)

| Cmpd No. | $B_{Nuc}/B_{Nuc(a)}$ | $L/L^a$ | $R/R^a$ | Name |
|---|---|---|---|---|
| 361 | guanin-9-yl | octadecyloxyethyl | naphthyl | naphthyl octadecyloxyethyl 9-(2-phosphonomethoxyethyl)guanine |
| 362 | adenine-9-yl | octadecyloxyethyl | naphthyl | naphthyl octadecyloxyethyl 9-(2-phosphonomethoxyethyl)adenine |
| 363 | cytosine-1-yl | octadecyloxyethyl | naphthyl | naphthyl octadecyloethyl 1-(2-phosphonomethoxyethyl)cytosine |
| 364 | thymin-1-yl | octadecyloxyethyl | naphthyl | naphthyl octadecyloxyethyl 1-(2-phosphonomethoxyethyl)thymine |
| 365 | uracil-1-yl | octadecyloxyethyl | naphthyl | naphthyl octadecyloxyethyl 9-(2-phosphonomethoxyethyl)uracil |
| 366 | 2,6-diaminopurin-9-yl | octadecyloxyethyl | naphthyl | naphthyl octadecyloxyethyl 9-(2-phosphonomethoxyethyl)-2,6-diaminopurine |
| 367 | guanin-9-yl | hexadecyloxypropyl | naphthyl | naphthyl hexadecyloxypropyl 9-(2-phosphonomethoxyethyl)guanine |
| 368 | adenine-9-yl | hexadecyloxypropyl | naphthyl | naphthyl hexadecyloxypropyl 9-(2-phosphonomethoxyethyl)adenine |

TABLE 6-continued

Phosphonomethoxyethyl (PME) diester compounds $B_{Nuc}/B_{Nuc(a)}$—CH$_2$CH$_2$—O—CH$_2$—P(=O)(O—L/L$^a$)(O—R/R$^a$)  or  (with wedge bond)  or  (with wavy bond)

Rp or Sp (depends on substituents)          Rp, Sp (racemic)

| Cmpd No. | $B_{Nuc}/B_{Nuc(a)}$ | L/L$^a$ | R/R$^a$ | Name |
|---|---|---|---|---|
| 369 | cytosine-1-yl | hexadecyloxypropyl | naphthyl | naphthyl hexadecyloxypropyl 1-(2-phosphonomethoxyethyl)cytosine |
| 370 | thymin-1-yl | hexadecyloxypropyl | naphthyl | naphthyl hexadecyloxypropyl 1-(2-phosphonomethoxyethyl)thymine |
| 371 | uracil-1-yl | hexadecyloxypropyl | naphthyl | naphthyl hexadecyloxypropyl 9-(2-phosphonomethoxyethyl)uracil |
| 372 | 2,6-diaminopurin-9-yl | hexadecyloxypropyl | naphthyl | naphthyl hexadecyloxypropyl 9-(2-phosphonomethoxyethyl)-2,6-diaminopurine |
| 373 | guanin-9-yl | 1-O-octadecyl-2-O-benzyl-sn glyceryl | naphthyl | naphthyl 1-O-octadecyl-2-O-benzyl-sn glyceryl 9-(2-phosphonomethoxyethyl)guanine |
| 374 | adenine-9-yl | 1-O-octadecyl-2-O-benzyl-sn glyceryl | naphthyl | naphthyl 1-O-octadecyl-2-O-benzyl-sn glyceryl 9-(2-phosphonomethoxyethyl)adenine |
| 375 | cytosine-1-yl | 1-O-octadecyl-2-O-benzyl-sn glyceryl | naphthyl | naphthyl 1-O-octadecyl-2-O-benzyl-sn glyceryl 1-(2-phosphonomethoxyethyl)cytosine |
| 376 | thymin-1-yl | 1-O-octadecyl-2-O-benzyl-sn glyceryl | naphthyl | naphthyl 1-O-octadecyl-2-O-benzyl-sn glyceryl 1-(2-phosphonomethoxy-ethyl)thymine |
| 377 | uracil-1-yl | 1-O-octadecyl-2-O-benzyl-sn glyceryl | naphthyl | naphthyl 1-O-octadecyl-2-O-benzyl-sn glyceryl 9-(2-phosphonomethoxy-ethyl)uracil |
| 378 | 2,6-diaminopurin-9-yl | 1-O-octadecyl-2-O-benzyl-sn glyceryl | naphthyl | naphthyl 1-O-octadecyl-2-O-benzyl-sn glyceryl 9-(2-phosphonomethoxy-ethyl)-2,6-diaminopurine |

TABLE 7

(R)-phosphonomethoxypropyl [(R)-PMP] diester compounds $B_{Nuc}/B_{Nuc(a)}$—CH$_2$—CH(CH$_3$)—O—CH$_2$—P(=O)(O—L/L$^a$)(O—R/R$^a$)  or  (wedge)  or  (wavy)

Rp or Sp (depends on substituents)          Rp, Sp (racemic)

| Cmpd No. | $B_{Nuc}/B_{Nac(a)}$ | L/L$^a$ | R/R$^a$ | Name |
|---|---|---|---|---|
| 379 | guanin-9-yl | octadecyloxyethyl | naphthyl | naphthyl octadecyloxyethyl 9-(R)-[(2-phosphonomethoxy)propyl]guanine |
| 380 | adenine-9-yl | octadecyloxyethyl | naphthyl | naphthyl octadecyloxyethyl 9-(R)-[(2-phosphonomethoxy)propyl]adenine |
| 381 | cytosine-1-yl | octadecyloxyethyl | naphthyl | naphthyl octadecyloxyethyl 1-(R)-[(2-phosphonomethoxy)propyl]cytosine |
| 382 | thymin-1-yl | octadecyloxyethyl | naphthyl | naphthyl octadecyloxyethyl 1-(R)-[(2-phosphonomethoxy)propyl]thymine |
| 383 | uracil-1-yl | octadecyloxyethyl | naphthyl | naphthyl octadecyloxyethyl 1-(R)-[(2-phosphonomethoxy)propyl]uracil |
| 384 | 2,6-diaminopurin-9-yl | octadecyloxyethyl | naphthyl | naphthyl octadecyloxyethyl 9-(R)-[(2-phosphonomethoxy)propyl]2,6-diaminopurine |
| 385 | guanin-9-yl | hexadecyloxypropyl | naphthyl | naphthyl hexadecyloxypropyl 9-(R)-[(2-phosphonomethoxy)propyl]guanine |
| 386 | adenine-9-yl | hexadecyloxypropyl | naphthyl | naphthyl hexadecyloxypropyl 9-(R)-[(2-phosphonomethoxy)propyl]adenine |

TABLE 7-continued (R)-phosphonomethoxypropyl [(R)-PMP] diester compounds

Rp or Sp (depends on substituents)          Rp, Sp (racemic)

| Cmpd No. | $B_{Nuc}/B_{Nac(a)}$ | $L/L^a$ | $R/R^a$ | Name |
|---|---|---|---|---|
| 387 | cytosine-1-yl | hexadeycloxypropyl | naphthyl | naphthyl hexahydecyloxypropyl 1-(R)-[(2-phosphonomethoxy)propyl]cytosine |
| 388 | thymin-1-yl | hexadecyloxypropyl | naphthyl | naphthyl hexadecyloxypropyl 1-(R)-[(2-phosphonomethoxy)propyl]thymine |
| 389 | uracil-1-yl | hexadecyloxypropyl | napthhyl | naphthyl hexadecyloxypropyl 1-(R)-[(2-phosphonomethoxy)propyl]uracil |
| 390 | 2,6-diaminopurin-9-yl | hexadecyloxypropyl | naphthyl | naphthyl hexadecyloxypropyl 9-(R)-[(2-phosphonomethoxy)propyl]2,6-diaminopurine |
| 391 | guanin-9-yl | 1-O-octadecyl-2-O-benzyl-sn glyceryl | naphthyl | naphthyl 1-O-octadecyl-2-O-benzyl-sn glyceryl 9-(R)-[(2-phosphonomethoxy)propyl]guanine |
| 392 | adenine-9-yl | 1-O-octadecyl-2-O-benzyl-sn glyceryl | naphthyl | naphthyl 1-O-octadecyl-2-O-benzyl-sn glyceryl 9-(R)-[(2-phosphonomethoxy)propyl]adenine |
| 393 | cytosine-1-yl | 1-O-octadecyl-2-O-benzyl-sn glyceryl | naphthyl | naphthyl 1-O-octadecyl-2-O-benzyl-sn glyceryl 1-(R)-[(2-phosphonomethoxy)propyl]cytosine |
| 394 | thymin-1-yl | 1-O-octadecyl-2-O-benzyl-sn glyceryl | naphthyl | naphthyl 1-O-octadecyl-2-O-benzyl-sn glyceryl 1-(R)-[(2-phosphonomethoxy)propyl]thymine |
| 395 | uracil-1-yl | 1-O-octadecyl-2-O-benzyl-sn glyceryl | naphthyl | naphthyl 1-O-octadecyl-2-O-benzyl-sn glyceryl 1-(R)-[(2-phosphonomethoxy)propyl]uracil |
| 396 | 2,6-diaminopurin-9-yl | 1-O-octadecyl-2-O-benzyl-sn glyceryl | naphthyl | naphthyl 1-O-octadecyl-2-O-benzyl-sn glyceryl 9-(R)-[(2-phosphonomethoxy)propyl]2,6-diaminopurine |

TABLE 8

(S)-3-methoxy-2-phosphonmethoxypropyl [(S)-MPMP] diester compounds

Rp or Sp (depends on substituents)          Rp, Sp (racemic)

| Cmpd No. | $B_{Nuc}/B_{Nuc(a)}$ | $L/L^a$ | $R/R^a$ | Name |
|---|---|---|---|---|
| 397 | guanin-9-yl | octadecyloxyethyl | naphthyl | naphthyl octadecyloxyethyl 9-(S)-[(3-methoxy-2-phosphonomethoxy)propyl]guanine |
| 398 | adenine-9-yl | octadecyloxyethyl | naphthyl | naphthyl octadecyloxyethyl 9-(S)-[(3-methoxy-2-phosphonomethoxy)propyl]adenine |
| 399 | cytosine-1-yl | octadecyloxyethyl | naphthyl | naphthyl octadecyloxyethyl 1-(S)-[(3-methoxy-2-phosphonomethxy)propyl]cytosine |
| 400 | thymin-1-yl | octadecyloxyethyl | naphthyl | naphthyl octadecyloxyethyl 1-(S)-[(3-methoxy-2-phosphonomethoxy)propyl]thymine |
| 401 | uracil-1-yl | octadecyloxyethyl | naphthyl | naphthyl octadecyloxyethyl 1-(S)-[(3-methoxy-2-phosphonomethoxy)propyl]uracil |

TABLE 8-continued

(S)-3-methoxy-2-phosphonmethoxypropyl [(S)-MPMP] diester compounds

Rp or Sp (depends on substituents) or Rp, Sp (racemic)

| Cmpd No. | $B_{Nuc}/B_{Nuc(a)}$ | $L/L^a$ | $R/R^a$ | Name |
|---|---|---|---|---|
| 402 | 2,6-diaminopurin-9-yl | octadecyloxyethyl | naphthyl | naphthyl octadecyloxyethyl 9-(S)-[(3-methoxy-2-phosphonomnethoxy)propyl]2,6-diaminopurine |
| 403 | guanin-9-yl | hexadecyloxypropyl | naphthyl | naphthyl hexadecyloxypropyl 9-(S)-[(3-methoxy-2-phosphonomethoxy)propyl]guanine |
| 404 | adenine-9-yl | hexadecyloxypropyl | naphthyl | naphthyl hexadecyloxypropyl 9-(S)-[(3-methoxy-2-phosphonomethoxy)propyl]adenine |
| 405 | cytosine-1-yl | hexadecyloxypropyl | naphthyl | naphthyl hexadecyloxypropyl 1-(S)-[(3-methoxy-2-phosphonomethoxy)propyl]cytosine |
| 406 | thymin-1-yl | hexadecyloxypropyl | naphthyl | naphthyl hexadecyloxypropyl 1-(S)-[(3-methoxy-2-phosphonomethoxy)propyl]thymine |
| 407 | uracil-1-yl | hexadecyloxypropyl | naphthyl | naphthyl hexadecyloxypropyl 1-(S)-[(3-methoxy-2-phosphonomethoxy)propyl]uracil |
| 408 | 2,6-diaminopurin-9-yl | hexadecyloxypropyl | naphthyl | naphthyl hexadecycloxypropyl 9-(S)-[(3-methoxy-2-phosphonomethoxy)propyl]2,6-diaminopurine |
| 409 | guanin-9-yl | 1-O-octadecyl-2-O-benzyl-sn glyceryl | naphthyl | naphthyl 1-O-octadecyl-2-O-benzyl-sn glyceryl 9-(S)-[(3-methoxy-2-phosphonomethoxy)propyl]guanine |
| 410 | adenine-9-yl | 1-O-octadecyl-2-O-benzyl-sn glyceryl | naphthyl | naphthyl 1-O-octadecyl-2-O-benzyl-sn glyceryl 9-(S)-[(3-methoxy-2-phosphonomethoxy)propyl]adenine |
| 411 | cytosine-1-yl | 1-O-octadecyl-2-O-benzyl-sn glyceryl | naphthyl | naphthyl 1-O-octadecyl-2-O-benzyl-sn glyceryl 1-(S)-[(3-methoxy-2-phosphonomethoxy)propyl]cytosine |
| 412 | thymin-1-yl | 1-O-octadecyl-2-O-benzyl-sn glyceryl | naphthyl | naphthyl 1-O-octadecyl-2-O-benzyl-sn glyceryl 1-(S)-[(3-methoxy-2-phosphonomethoxy)propyl]thymine |
| 413 | uracil-1-yl | 1-O-octadecyl-2-O-benzyl-sn glyceryl | naphthyl | naphthyl 1-O-octadecyl-2-O-benzyl-sn glyceryl 1-(S)-[(3-methoxy-2-phosphonomethoxy)propyl]uracil |
| 414 | 2,6-diaminopurin-9-yl | 1-O-octadecyl-2-O-benzyl-sn glyceryl | naphthyl | naphthyl 1-O-octadecyl-2-O-benzyl-sn glyceryl 9-(S)-[(3-methoxy-2-phosphonomethoxy)propyl]2,6-diaminopurine |

TABLE 9

(S)-3-hydroxy-2-phosphonomethoxypropyl [(S)-HPMP] diester compounds

Rp or Sp (depends on substituents) or Rp, Sp (racemic)

| Cmpd No. | $B_{Nuc}/B_{Nuc(a)}$ | $L/L^a$ | $R/R^a$ | Name |
|---|---|---|---|---|
| 415 | guanin-9-yl | octadecyloxyethyl | naphthyl | naphthyl octadecyloxyethyl 9-(S)-[(3-hydroxy-2-phosphonomethoxy)propyl]guanine |

TABLE 9-continued (S)-3-hydroxy-2-phosphonomethoxypropyl [(S)-HPMP] diester compounds Rp or Sp (depends on substituents)   Rp, Sp (racemic)

| Cmpd No. | B$_{Nuc}$/B$_{Nuc(a)}$ | L/L$^a$ | R/R$^a$ | Name |
|---|---|---|---|---|
| 416 | adenine-9-yl | octadecyloxyethyl | naphthyl | naphthyl octadecyloxyethyl 9-(S)-[(3-hydroxy-2-phosphonomethoxy)propyl]adenine |
| 417 | cytosine-1-yl | octadecyloxyethyl | naphthyl | naphthyl octadecyloxyethyl 1-(S)-[(3-hydroxy-2-phosphonomethoxy)propyl]cytosine |
| 418 | thumin-1-yl | octadecyloxyethyl | naphthyl | naphthyl octadecyloxyethyl 1-(S)-[93-hydroxy-2-phosphonomethoxy)propyl]thymine |
| 419 | uracil-1-yl | octadecyloxyethyl | naphthyl | naphthyl octadecyloxyethyl 1-(S)-[(3-hydroxy-2-phosphonomethoxy)propyl]uracil |
| 420 | 2,6-diaminopurin-9-yl | octadecyloxyethyl | naphthyl | naphthyl octadecyloxyethyl 9-(S)-[(3-hydroxy-2-phosphonomethoxy)propyl]2,6-diaminopurine |
| 421 | guanin-9-yl | hexadecyloxypropyl | naphthyl | naphthyl hexadecyloxypropyl 9-(S)-[(3-hydroxy-2-phosphonomethoxy)propyl]guanine |
| 422 | adenine-9-yl | hexadecyloxypropyl | naphthyl | naphthyl hexadecyloxypropyl 9-(S)-[(3-hydroxy-2-phosphonomethoxy)propyl]adenine |
| 423 | cytosine-1-yl | hexadecyloxypropyl | naphthyl | naphthyl hexadecyloxypropyl 1-(S)-[(3-hydroxy-2-phosphonomethoxy)propyl]cytosine |
| 424 | thymin-1-yl | hexadecyloxypropyl | naphthyl | naphthyl hxadecyloxypropyl 1-(S)-[(3-hydroxy-2-phosphonomethoxy)propyl]thymine |
| 425 | uracil-1-yl | hexadecyloxypropyl | naphthyl | naphthyl hexadecyloxypropyl 1-(S)-[(3-hydroxy-2-phosphonomethoxy)propyl]uracil |
| 426 | 2,6-diaminopurin-9-yl | hexadecyloxypropyl | naphthyl | naphthyl hexadecyloxypropyl 9-(S)-[(3-hydroxy-2-phosphonomethoxy)propyl]2,6-diaminopurine |
| 427 | guanin-9-yl | 1-O-octadecyl-2-O-benzyl-sn glyceryl | naphthyl | naphthyl 1-O-octadecyl-2-O-benzyl-sn glyceryl 9-(S)-[(3-hydroxy-2-phosphonomethoxy)propyl]guanine |
| 428 | adenine-9-yl | 1-O-octadecyl-2-O-benzyl-sn glyceryl | naphthyl | naphthyl 1-O-octadecyl-2-O-benzyl-sn glyceryl 9-(S)-[(3-hydroxy-2-phosphonomethoxy)propyl]adenine |
| 429 | cytosine-1-yl | 1-O-octadecyl-2-O-benzyl-sn glyceryl | naphthyl | naphthyl 1-O-octadecyl-2-O-benzyl-sn glyceryl 1-(S)-[(3-hydroxy-2-phosphonomethoxy)propyl]cytosine |
| 430 | thymin-1-yl | 1-O-octadecyl-2-O-benzyl-sn glyceryl | naphthyl | naphthyl 1-O-octadecyl-2-O-benzyl-sn glyceryl 1-(S)-[(3-hydroxy-2-phosphonomethoxy)propyl]thymine |
| 431 | uracil-1-yl | 1-O-octadecyl-2-O-benzyl-sn glyceryl | naphthyl | naphthyl 1-O-octadecyl-2-O-benzyl-sn glyceryl 1-(S)-[(3-hydroxy-2-phosphonomethoxy)propyl]uracil |
| 432 | 2,6-diaminopurin-9-yl | 1-O-octadecyl-2-O-benzyl-sn glyceryl | naphthyl | naphthyl 1-O-octadecyl-2-O-benzyl-sn glyceryl 9-(S)-[(3-hydroxy-2-phosphonomethoxy)propyl]2,6-diaminopurine |

TABLE 10

(S)-3-fluoro-2-phosphonomethoxypropyl [(S)-FPMP] diester compounds

Rp or Sp (depends on substituents)    Rp, Sp (racemic)

| Cmpd No. | B$_{Nuc}$/B$_{Nac(a)}$ | L/L$^a$ | R/R$^a$ | Name |
|---|---|---|---|---|
| 433 | guanin-9-yl | octadecyloxyethyl | naphthyl | naphthyl octadecyloxyethyl 9-(S)-[(3-fluoro-2-phosphonomethoxy)propyl]guanine |
| 434 | adenine-9-yl | octadecyloxyethyl | naphthyl | naphthyl octadecyloxyethyl 9-(S)-[(3-fluoro-20 phosphonomethoxy)propyl]adenine |
| 435 | cytosine-1-yl | octadecyloxyethyl | naphthyl | naphthyl octadecyloxyethyl 1-(S)-[(3-fluoro-2-phosphonomethoxy)propyl]cytosine |
| 436 | thymin-1-yl | octadecyloxyethyl | naphthyl | naphthyl octadecyloxyethyl 1-(S)-[(3-fluor -2-phosphonomethoxy)propyl]thymine |
| 437 | uracil-1-yl | octadecyloxyethyl | naphthyl | naphthyl octadecyloxyethyl 9-(S)-[(3-fluoro-2-phosphonomethoxy)propyl]2,6-diaminopurine |
| 438 | 2,6-diaminopurin-9-yl | octadecyloxyethyl | naphthyl | naphthyl octadecyloxyethyl 9-(S)-[(3-fluoro-2-phosphonomethoxy)propyl[2,6-diaminopurine |
| 439 | guanin-9-yl | hexadecyloxypropyl | naphthyl | naphthyl hexadecyloxypropyl 9-(S)-[(3-fluoro-2-phosphonomethoxy)propyl]guanine |
| 440 | adenine-9-yl | hexadecyloxypropyl | naphthyl | naphthyl hexadecyloxypropyl 9-(S)-[(3-fluoro-2-phosphonomethoxy)propyl]adenine |
| 441 | cytosine-1-yl | hexadecyloxypropyl | naphthyl | naphthyl hexadecyloxypropyl 1-(S)-[(3-fluoro-2-phosphonomethoxy)propyl]cytosine |
| 442 | thymin-1-yl | hexadecyloxypropyl | naphthyl | naphthyl hexadecyloxpropyl 1-(S)-[(3-fluoro-2-phosphonomethoxy)propyl]thymine |
| 443 | uracil-1-yl | hexadecyloxypropyl | naphthyl | naphthyl hexadecyloxypropyl 1-(S)-[3-fluoro-2-phosphonomethoxy)propyl]uracil |
| 444 | 2,6-diaminopurin-9-yl | hexadecyloxypropyl | naphthyl | naphthyl hexadecyloxypropyl 9-(S)-[(3-fluoro-2-phosphonomethoxy)propyl]2,6-diaminopurine |
| 445 | guanin-9-yl | 1-O-octadecyl-2-O-benzyl-sn glyceryl | naphthyl | naphthyl 1-O-octadecyl-2-O-benzyl-sn glyceryl 9-(S)-[(3-fluoro-2-phosphonomethoxy)propyl]guanine |
| 446 | adenine-9-yl | 1-O-octadecyl-2-O-benzyl-sn glyceryl | naphthyl | naphthyl 1-O-octadecyl-2-O-benzyl-sn glyceryl 9-(S)-[(3-fluoro-2-phosphonomethoxy)propyl]adenine |
| 447 | cytosine-1-yl | 1-O-octadecyl-2-O-benzyl-sn glyceryl | naphthyl | naphthyl 1-O-octadecyl-2-O-benzyl-sn glyceryl 1-(S)-[(3-fluoro-2-phosphonomethoxy)propyl]cytosine |
| 448 | thymin-1-yl | 1-O-octadecyl-2-O-benzyl-sn glyceryl | naphthyl | naphthyl 1-O-octadecyl-2-O-benzyl-sn glyceryl 1-(S)-[(3-fluoro-2-phosphonomethoxy)propyl]thymine |
| 449 | uracil-1-yl | 1-O-olctadecyl-2-O-benzyl-sn glyceryl | naphthyl | naphthyl 1-O-octadecyl-2-O-benzyl-sn glyceryl 1-(S)-[(3-fluoro-2-phosphonomethoxy)propyl]uracil |
| 450 | 2,6-diaminopurin-9-yl | 1-O-octadecyl-2-O-benzyl-sn glyceryl | naphthyl | naphthyl 1-O-octadecyl-2-O-benyzl-sn glyceryl 9-(S)-[(3-fluoro-2-phosphonomethoxy)propyl]2,6-diaminopurine |

Specific compounds contemplated herein include:

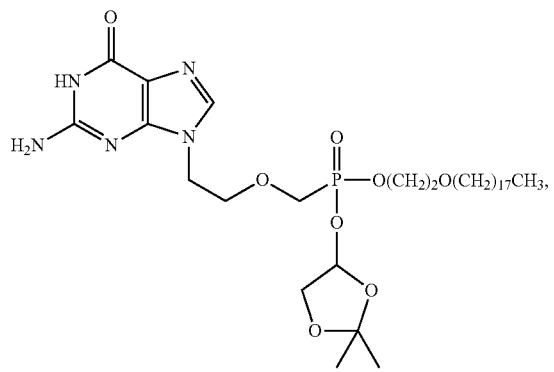

isopropylideneglyceryl octadecyloxyethyl
9-[2-(phosphonomethoxy)ethyl]guanine

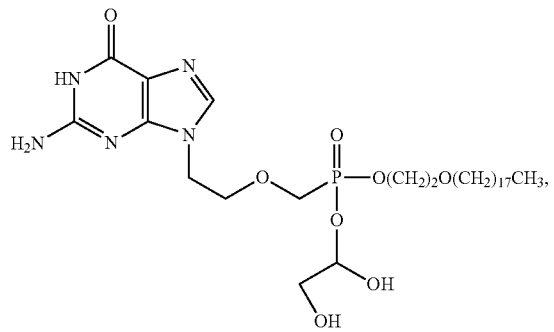

glyceryl octadecyloxyethyl
9-[2-(phosphonomethoxy)ethyl]guanine

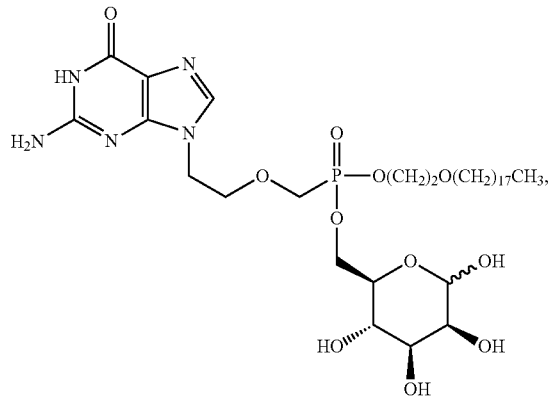

mannosyl octadecyloxyethyl
9-[2-(phosphonomethoxy)ethyl]guanine

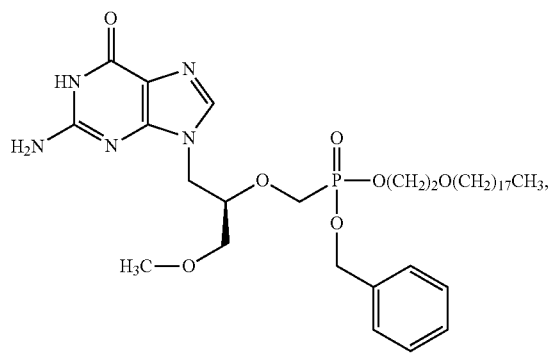

benzyl octadecyloxyethyl
9-(R)-[3-methoxy-2-(phosphonomethoxy)propyl]
guanine

-continued

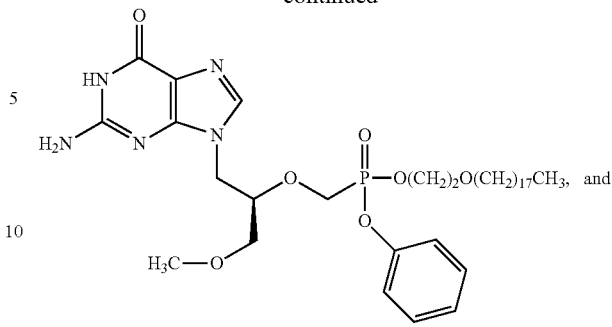

Phenyl octadecyloxyethyl
9-(R)-[3-methoxy-2-(phosphonomethoxy)propyl]
guanine

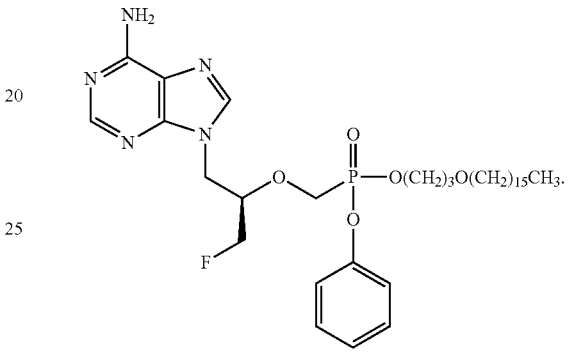

phenyl hexadecyloxypropyl
9-(R)-[3-fluoro-2-(phosphonomethoxy)propyl]
adenine

III. Methods of Use

In another aspect, there is provided a method for treating a viral disease in a subject. The method includes administering to a subject in need thereof a therapeutically effective amount of a compound with structure of any of Formulae (I), (I-1), (I-2), (I-3), (I-4), (I-5) and/or (Ia). In embodiments, $L/L^a$ of any of Formulae (I), (I-1), (I-2), (I-3), (I-4), (I-5) and/or (Ia) is a lipophilic promoiety.

Exemplary viral diseases include human papilloma virus, HIV, hepatitis B virus, hepatitis C virus, variola virus (smallpox), vaccinia virus, adenovirus, cytomegalovirus (CMV), herpes simplex viruses, Epstein Barr virus, BK virus, JC virus, any double stranded DNA virus, feline leukemia virus, feline immunodeficiency virus, and the like. A therapeutically effective amount of a compound of Formula (I) can be administered to a human or mammal in need of treatment of a viral disease.

In embodiments, the compound is administered by a route (topical, intravitreal, oral, intravenous etc.) which results in delivery of an amount sufficient to inhibit replication of the virus. In embodiments, the compound can be administered topically. For example, the compound can be administered topically in the form of a cream, a gel or an ointment In another aspect, there is provided a method for treating a disease or disorder in a subject in need thereof, the method including administering to a subject in need thereof a therapeutically effective amount of a compound with structure of any of Formulae (I), (I-1), (I-2), (I-3), (I-4), (I-5) and/or (Ia). Aspects for the treatment of cancer and other neoplastic disorders contemplated herein are based on the surprising discovery that compounds of Formulae (I) and/or (Ia) are effective in killing or inhibiting growth of cells that are transformed by human papillomavirus (HPV), for example cervical cancer cells and cervical intraepithelial neoplasia (CIN) lesions. Accordingly, a therapeutically effective amount of a compound of Formula (I), (I-1), (I-2), (I-3), (I-4), (I-5) and/or (Ia) can be administered by an appropriate route (topical, orally, intravenous etc.) to kill or inhibit growth of infected/transformed cells. Cells that are transformed by other types of viruses, such as herpes simplex virus-2 (HSV-2), also may be treated with a compound of Formula (I), (I-1), (I-2), (I-3), (I-4), (I-5) and/or (Ia).

In another aspect, there is provided a method for treating cancer in a subject. The method includes administering to a subject in need thereof a therapeutically effective amount of a compound with the structure of any of Formulae (I), (I-1), (I-2), (I-3), (I-4), (I-5) and/or (Ia). In embodiments, $L/L^a$ of any of Formulae (I), (I-1), (I-2), (I-3), (I-4), (I-5) and/or (Ia) is a lipophilic promoiety.

In embodiments, the cancer is leukemia, carcinoma and/or sarcoma, such as cancer of the brain, breast, cervix, colon, pancreas, head and neck, liver, kidney, lung, non-small cell lung, prostate, melanoma, mesothelioma, ovary, sarcoma, stomach, uterus and/or medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas. In embodiments, the cancer is liver cancer, colon cancer, breast cancer, melanoma, acute myelogenous leukemia, chronic myelogenous leukemia, and/or non-small-cell lung cancer.

In another aspect, there is provided a method for treating a proliferative disorder in a subject. The method includes administering to a subject in need thereof a therapeutically effective amount of a compound with the structure of any of Formulae (I), (I-1), (I-2), (I-3), (I-4), (I-5) and/or (Ia). The proliferative disorder may be caused by the human papilloma virus. Exemplary proliferative disorders include, e.g., cervical intraepithelial neoplasia (CIN), vulvar intraepithelial neoplasia (VIN), anal intraepithelial neoplasia (AIN), or penile and venereal warts. In embodiments, $L/L^a$ of any of Formulae (I), (I-1), (I-2), (I-3), (I-4), (I-5) and/or (Ia) is a lipophilic promoiety.

In another aspect, there is provided a method for killing or inhibiting the growth of a transformed cell. The method includes contacting a transformed cell with a therapeutically effective amount of a compound of any one of Formulae (I), (I-1), (I-2), (I-3), (I-4), (I-5) and/or (Ia).

In another aspect, there is provided a compound of Formula (Ia) or embodiment thereof, or a pharmaceutically acceptable salt, hydrate, solvate or crystalline form thereof, for use in treating a viral disease in a subject, wherein the viral disease can be selected from human papilloma virus (HPV), HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In embodiments, the virus can be human papilloma virus. According to the CDC, HPV is the most common sexually transmitted infection (STI). HPV viruses can be classified into mucosal and cutaneous HPVs. Within each of these groups, the individual viruses are designated high risk or low risk. More than 40 types of HPV's can infect the genital areas of women and men, and several HPV types can infect the mouth and throat. Additionally, HPV is the most common cause of cervical cancer. Type 16 is one of the most prominent strains of HPV and can cause cervical cancer. Other types of HPVs include, but are not limited to, 2, 3, 4, 5, 6, 8, 11, 16, 18, 31, 33, 35, 39, 45, 51, 52, 56, 58, 59, 63, 66, 68, 69 and 82. In embodiments, the use is for treating a plurality of types of human papilloma virus, for example, types described herein. In embodiments, the use is for more than 2 types of HPV, more than 5 types of HPV or more than 10 types of HPV. In embodiments, the human papilloma virus can be selected from human papilloma virus type 11, type 16 and type 18.

In another aspect, there is provided use of a compound of Formula (Ia) or embodiment thereof, or a pharmaceutically acceptable salt, hydrate, solvate or crystalline form thereof, in the preparation of a medicament for treating a viral disease in a subject, wherein the viral disease can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In embodiments, the virus can be human papilloma virus. In embodiments, the use is for treating a plurality of types of human papilloma virus, for example, types described herein. In embodiments, the use is for more than 2 types of HPV, more than 5 types of HPV or more than 10 types of HPV. In embodiments, the human papilloma virus can be selected from human papilloma virus type 11, type 16 and type 18.

In another aspect, there is provided a method of treating a subject having a viral disease. The method include administering to the subject having a viral disease in need thereof an effective amount of a compound of Formula (Ia) or embodiment thereof, or a pharmaceutically acceptable salt, hydrate, solvate or crystalline form thereof, wherein the viral disease can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus, thereby treating the viral disease.

In another aspect, there is provided a compound of Formula (Ia) or embodiment thereof, or a pharmaceutically acceptable salt, hydrate, solvate or crystalline form thereof, for use in treating cancer of the cervix in a subject. In some embodiments, the cancer of the cervix can be caused by a HPV infection, for example, a HPV infection of type 16.

In another aspect, there is provided use of a compound of Formula (Ia) or embodiment thereof, or a pharmaceutically acceptable salt, hydrate, solvate or crystalline form thereof, in the preparation of a medicament for treating cancer of the cervix in a subject. In some embodiments, the cancer of the cervix can be caused by a HPV infection, for example, a HPV infection of type 16.

In another aspect, there is provided a method of treating a subject having cancer of the cervix. The method includes administering an effective amount of a compound of Formula (Ia) or embodiment thereof, or a pharmaceutically acceptable salt, hydrate, solvate or crystalline form thereof, to a subject having cancer of the cervix in need thereof, thereby treating the subject having cancer of the cervix. In some embodiments, the cancer of the cervix can be caused by a HPV infection, for example, a HPV infection of type 16.

In another aspect, there is provided a compound of Formula (Ia) or embodiment thereof, or a pharmaceutically acceptable salt, hydrate, solvate or crystalline form thereof, for use in inhibiting growth of a cell transformed by a virus, wherein the virus can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In another aspect, there is provided use of a compound of Formula (Ia) or embodiment thereof, or a pharmaceutically acceptable salt, hydrate, solvate or crystalline form thereof, in the preparation of a medicament for inhibiting growth of a cell transformed by a virus, wherein the virus can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

In another aspect, there is provided a method of inhibiting growth of a cell transformed by a virus. The method includes contacting a compound of Formula (Ia) or embodiment thereof, or a pharmaceutically acceptable salt, hydrate, solvate or crystalline form thereof, with a cell transformed by a virus, wherein the virus can be selected from human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus, thereby inhibiting growth of the cell transformed by a virus.

IV. Methods of Synthesis

In another aspect, there is provided a method for synthesis of compounds of Formula (I), as depicted in Scheme 1 following. For Scheme 1, substituents $B_{Nuc}$, X, R and L are as described for Formula (I) herein.

In another aspect, there is provided a method for synthesis of compounds of Formula (Ia), as depicted in Scheme 1a following. For Scheme 1a, substituents $B_{Nuc(a)}$, $X^a$, $R^a$ and $L^a$ are as described for Formula (Ia) herein.

The method includes reacting a suitably substituted ANP monoester with R—OH or $R^a$—OH in the presence of a coupling agent such as (benzotriazol-1-yloxy)-tripyrrolidinophosphonium hexafluorophosphate (PYBOP®) to give a diester. Methods for preparing the ANP monoesters are well known. For examples, see Beadle, J. R et al. *Journal of Medicinal Chemistry*, 2006, 49:2010-2015, and Valiaeva, N. et al. *Antiviral Research*, 2006, 72:10-19. The use of PYBOP® for synthesis of phosphonate diesters was first described in Campagne, J-M. et al. *Tetrahedron Letters*, 1993, 34:6743-6744. Other coupling/condensation reagents, for example uronium, carbodiimide, imidazolium and acid chloride reagents, may also be used (for a review of coupling agents see, e.g., El-Faham, A. & Albericio, F. *Chemical Reviews*, 2011, 111:6557-6602).

Scheme 1

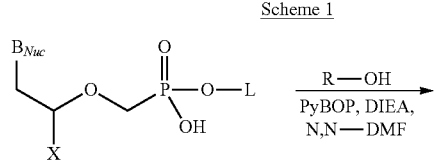

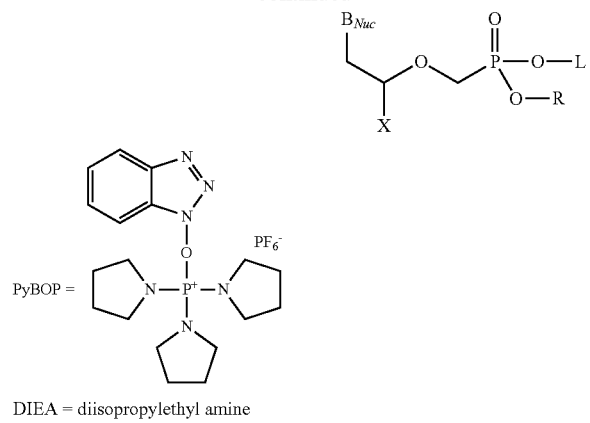

DIEA = diisopropylethyl amine

Scheme 1a

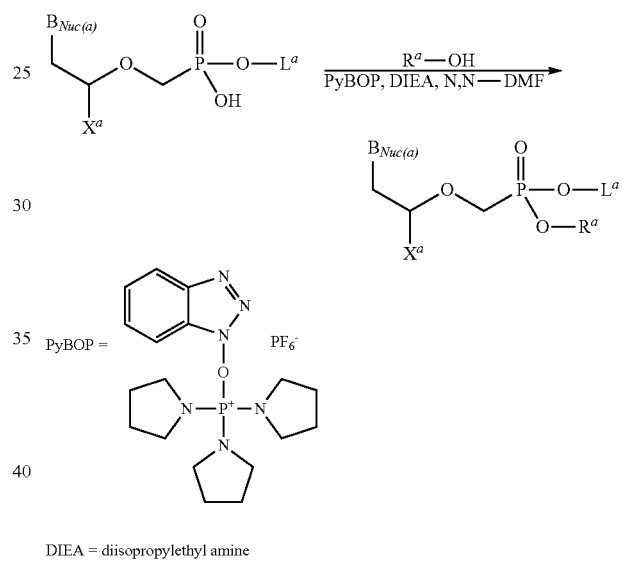

DIEA = diisopropylethyl amine

In another aspect, there is provided a method for synthesis of compounds of Formula (I). The method includes the steps provided in Scheme 2 following:

Scheme 2

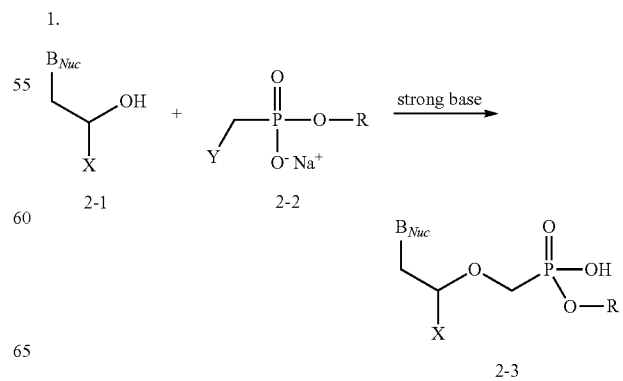

2.

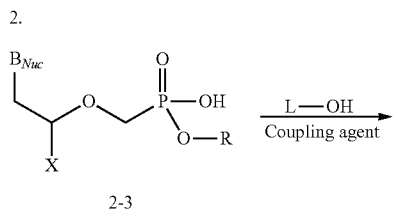

2-3

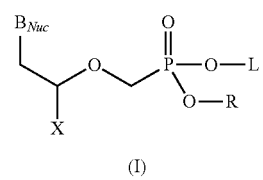

(I)

In the method of Scheme 2, $B_{Nuc}$ is a naturally occurring purine or pyrimidine base, or analog thereof; L is a lipophilic promoiety, substituted or unsubstituted alkyl, substituted or unsubstituted heteroalkyl, or O-substituted glyceryl having the formula —$CH_2CH(OR^1)$—$CH_2(OR^2)$ (II), wherein $R^1$ and $R^2$ are independently substituted or unsubstituted alkyl or substituted or unsubstituted aryl; R is substituted or unsubstituted lower alkyl, substituted or unsubstituted lower heteroalkyl, substituted or unsubstituted lower cycloalkyl, substituted or unsubstituted lower heterocycloalkyl, substituted or unsubstituted aryl, or substituted or unsubstituted lower heteroaryl; X is hydrogen, substituted or unsubstituted lower alkyl, or substituted or unsubstituted lower heteroalkyl; and Y is a leaving group.

The method includes: 1) contacting a protected nucleoside $B_{Nuc}$ with structure of Formula (2-1) with an ester with structure of Formula (2-2) in the presence of a strong base under conditions suitable to afford a monoester with structure of Formula (2-3); and 2) reacting the monoester so formed with structure of Formula (2-3) with L-OH in the presence of a coupling agent as known in the art, thereby synthesizing a compound with structure of Formula In another aspect, there is provided a method for synthesis of compounds of Formula (Ia). The method includes the following as provided in Scheme 2a. For Scheme 2a, substituents $B_{Nuc(a)}$, $X^a$, $R^a$ and $L^a$ are as described for Formula (Ia) herein, and $Y^a$ can be a leaving group.

Scheme 2a

1.

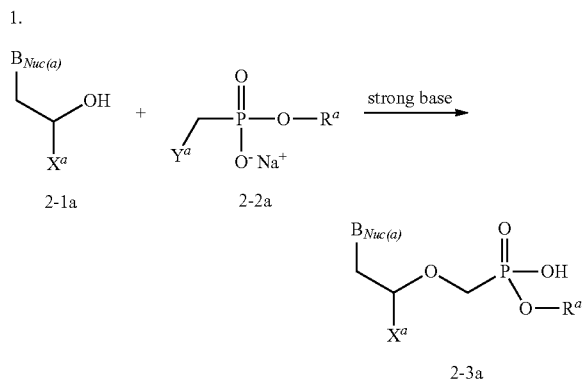

2.

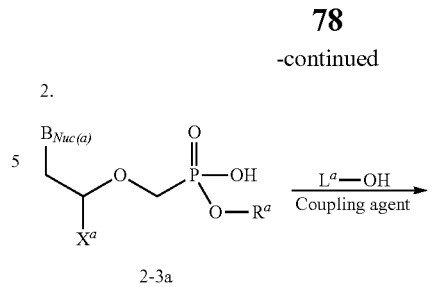

2-3a

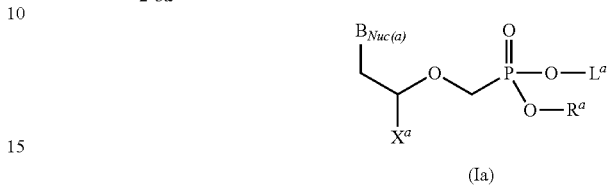

(Ia)

The method includes: 1) contacting a protected nucleoside $B_{Nuc(a)}$ with structure of Formula (2-1a) with an ester with structure of Formula (2-2a) in the presence of a strong base under conditions suitable to afford a monoester with structure of Formula (2-3a); and 2) reacting the monoester so formed with structure of Formula (2-3a) with $L^a$-OH in the presence of a coupling agent as known in the art, thereby synthesizing a compound with structure of Formula (Ia).

In embodiments, the method includes the steps provided in Scheme 2-1 following, specifically, contacting a suitably protected nucleoside (general structure 2-1 where $B_{Nuc}$ is a naturally occurring or modified purine or pyrimidine base, with an ester of general structure 2-2 (where Y is a leaving group such as p-toluenesulfonyl, methanesulfonyl, trifluoromethanesulfonyl, bromo, iodo, or the like) in the presence of a strong base and suitable solvent to yield ANP monoesters of Formula 2-3, and secondly, reacting ANP monoester 2-3 with L-OH (i.e., hydroxy form of L) in the presence of a coupling agent such as PYBOP® to give a diester of Formula (I).

Scheme 2-1

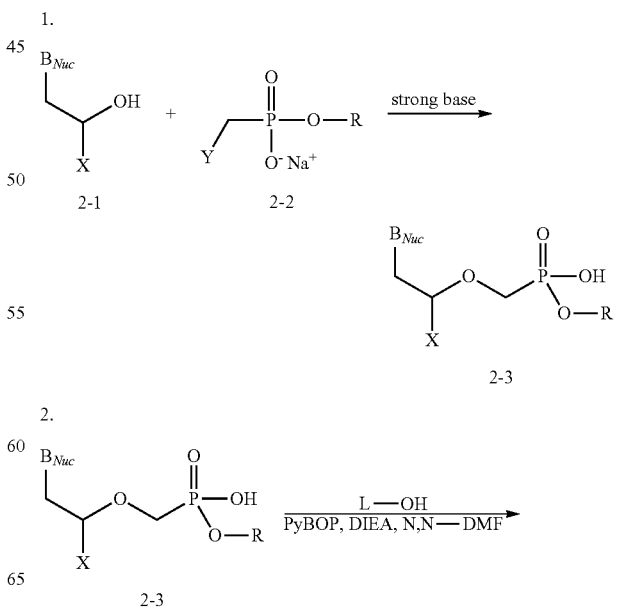

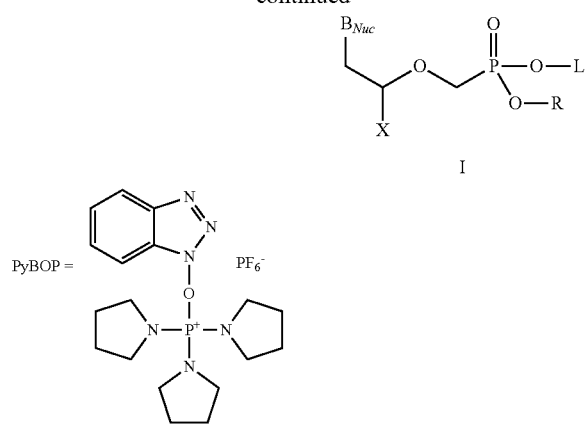

DIEA = diisopropylethyl amine

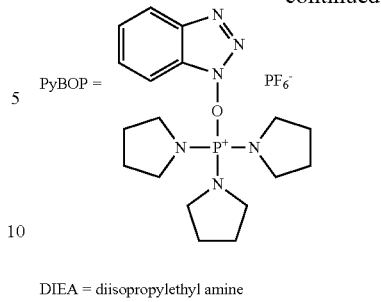

DIEA = diisopropylethyl amine

In another aspect, there is provided method for synthesis of a compound with structure of Formula (I) according to Scheme 2-1. $B_{Nuc}$, X, R and L are as described for Formula (I) herein, and Y can be a leaving group; said method comprising: contacting a compound of Formula (2-1) that has a protected $B_{Nuc}$ with a compound of Formula (2-2) in the presence of a strong base to form a compound of Formula (2-3); and reacting the compound of Formula (2-3) with L-OH in the presence of a coupling agent to form the compound of Formula (I).

Scheme 2-1a

1.

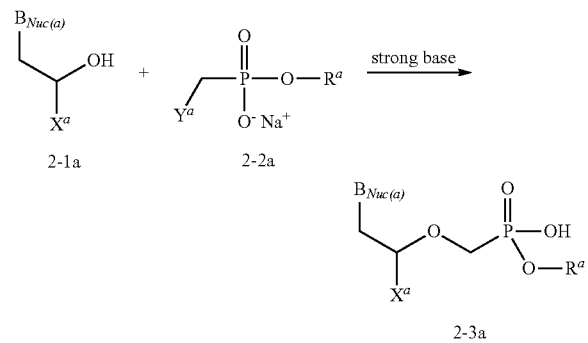

2.

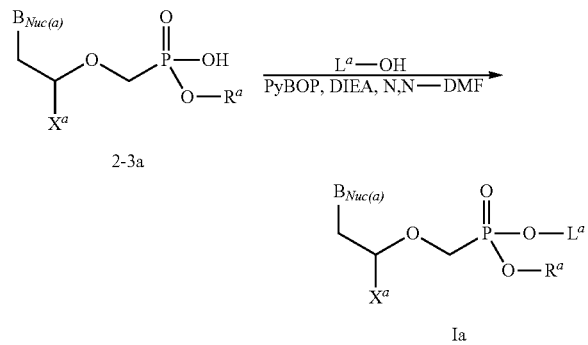

In another aspect, there is provided method for synthesis of a compound with structure of Formula (Ia) according to Scheme 2-1a. For this method, $B_{Nuc(a)}$ can be a naturally occurring purine, a naturally occurring pyrimidine, a non-naturally occurring purine or a non-naturally occurring pyrimidine; $L^a$ can be an unsubstituted $C_{12-24}$ alkyl, an unsubstituted $C_{13-29}$ heteroalkyl or a substituted glyceryl moiety, wherein the glyceryl moiety can be substituted with one or more groups selected from an unsubstituted $C_{13-29}$ alkyl, an unsubstituted $C_{13-29}$ heteroalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); le can be selected from an unsubstituted $C_{1-6}$ alkyl, a substituted or unsubstituted aryl, a substituted or unsubstituted heteroaryl, a substituted or unsubstituted heterocycloalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); $X^a$ can be hydrogen, an unsubstituted $C_{1-6}$ alkyl, a halogen substituted $C_{1-6}$ alkyl, a hydroxy substituted $C_{1-6}$ alkyl or an unsubstituted $C_{1-6}$ alkoxy; and $Y^a$ can be a leaving group; said method comprising: contacting a compound of Formula (2-1a) that has a protected $B_{Nuc(a)}$ with a compound of Formula (2-2a) in the presence of a strong base to form a compound of Formula (2-3a); and reacting the compound of Formula (2-3a) with $L^a$-OH in the presence of a coupling agent to form the compound of Formula (Ia).

In another aspect, there is provided a method for synthesizing a compound of Formula (I) as described in Scheme 3 following. For Scheme 3, substituents $B_{Nuc}$, X, R and L are as described for Formula (I) herein.

Scheme 3

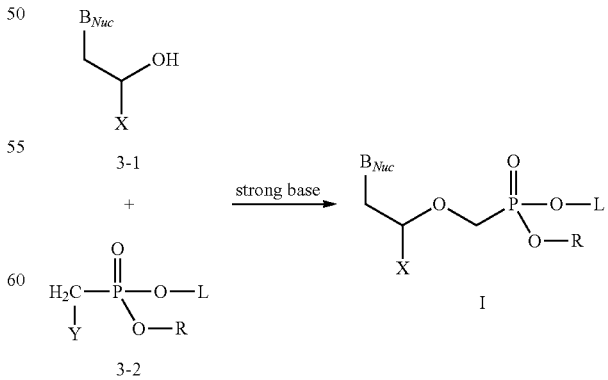

The method includes contacting a suitably protected nucleoside (general structure 3-1 where $B_{Nuc}$ is a naturally occurring or modified purine or pyrimidine base), with a diester of general structure 3-2 (where Y is a leaving group such as p-toluenesulfonyl, methanesulfonyl, trifluoromethanesulfonyl, bromo, iodo, or the like.) in the presence of a strong base and suitable solvent to yield a compound of Formula (I).

In another aspect, there is provided a method for synthesizing a compound of Formula (Ia) as described in Scheme 3a. For Scheme 3a, substituents $B_{Nuc(a)}$, $X^a$, $R^a$ and $L^a$ are as described for Formula (Ia) herein, and $Y^a$ is a leaving group.

Scheme 3a

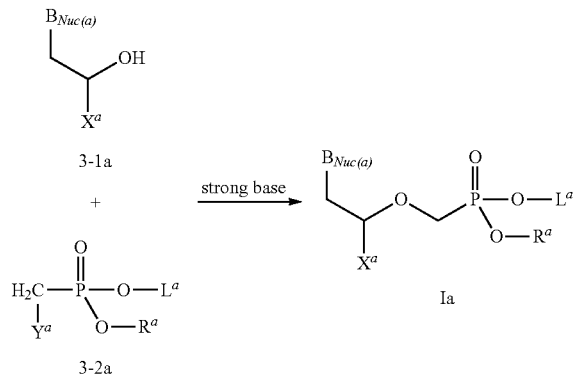

The method includes contacting a suitably protected nucleoside (3-1a), with a diester 3-2 (where $Y^a$ is a leaving group such as p-toluenesulfonyl, methanesulfonyl, trifluoromethanesulfonyl, bromo, iodo, or the like) in the presence of a strong base and suitable solvent to yield a compound of Formula (Ia).

V. Pharmaceutical Compositions

In another aspect, there is provided a pharmaceutical compositions including a compound of Formula (I) and/or a compound of Formula (Ia) in combination with a pharmaceutically acceptable excipient (e.g., carrier).

The terms "pharmaceutically acceptable carrier," "pharmaceutically acceptable excipient" and the like as used herein refer to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein.

The compounds described herein can be administered alone or can be coadministered to the subject. Coadministration is meant to include simultaneous or sequential administration of the compounds individually or in combination (more than one compound). The preparations can also be combined, when desired, with other active substances (e.g., to reduce metabolic degradation).

A. Formulations

The compounds described herein can be prepared and administered in a wide variety of oral, parenteral, and topical dosage forms. Thus, the compounds described herein can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. It is also envisioned that multiple routes of administration (e.g., intramuscular, oral, transdermal) can be used to administer the compounds described herein. Accordingly, pharmaceutical compositions comprising a pharmaceutically acceptable carrier or excipient and one or more compounds are contemplated.

For preparing pharmaceutical compositions, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures are injectable, sterile solutions, preferably oily or aqueous solutions, as well as suspensions, emulsions, or implants, including suppositories. In particular, carriers for parenteral administration include aqueous solutions of dextrose, cyclodextrins, saline, pure water, ethanol, glycerol, propylene glycol, peanut oil, sesame oil, polyoxyethylene-block polymers, and the like. Ampoules are convenient unit dosages. The compounds described herein can also be incorporated into liposomes or administered via transdermal pumps or patches. Pharmaceutical admixtures suitable for use include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and/or thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. In embodiments, the unit dosage form can be in the form of an applicator pre-filled with a pharmaceutical composition described herein (for example, a pharmaceutical composition that contains an effective amount of a compound of Formula (I) and/or a compound of Formula (Ia)). In embodiments, the pre-filled applicator can be filled with a pharmaceutical composition in the form of a cream, a gel or an ointment that contains a compound described herein (for example, a compound of Formula (I) and/or a compound of Formula (Ia)).

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; PLURONIC® F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g., decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds described herein.

For any compound described herein, the therapeutically effective amount can be initially determined from cell culture assays. Therapeutically effective amounts for use in humans may subsequently be estimated from animal models using conventional techniques that are confirmed or refined in actual clinical trials.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

VI. Examples

General Chemistry Methods

All reagents were of commercial quality and used without further purification unless indicated otherwise. Chromatographic purification was done using the flash method with silica gel 60 (EMD Chemicals, Inc., 230-400 mesh). $^1$H NMR spectra were recorded on a Varian HG spectrophotometer operating at 400 MHz and are reported in units of parts per million (ppm) relative to internal tetramethylsilane at 0.00 ppm. Routine electrospray ionization mass spectra (ESI-MS) were recorded on a Finnigan LCQ DECA spectrometer, and high resolution mass spectra (HRMS) were recorded on an Agilent 6230 Accurate-Mass TOFMS mass spectrometer in ESI negative mode. Purity of the target compounds was characterized by high performance liquid chromatography (HPLC) using a Beckman Coulter SYSTEM GOLD® chromatography system. The analytical column was PHENOMENEX® SYNERGI™ Polar-RP (4.6× 150 mm) equipped with a SECURITYGUARD™ protection column. Mobile phase A was 95% water/5% methanol and mobile phase B was 95% methanol/5% water. At a flow rate of 0.8 mL/min, isocratic elution was used. Compounds were detected by ultraviolet light (UV) absorption at 274 nm.

Homogeneity of the target compounds was also confirmed by thin layer chromatography (TLC) using Analtech silica gel-GF (250 µm) plates and the solvent system: $CHCl_3$/MeOH/con $NH_4OH/H_2O$ (70:30:3:3 v/v). TLC results were visualized with UV light, phospray (SUPELCO®, Bellefonte, Pa., USA) and charring at 400° C.

Example 1

Preparation of benzyl octadecyloxyethyl 9-[2-(phosphonomethoxy) ethyl]guanine, 1-(Rp,Sp) (Cmpd 1, Bn-ODE-PMEG)

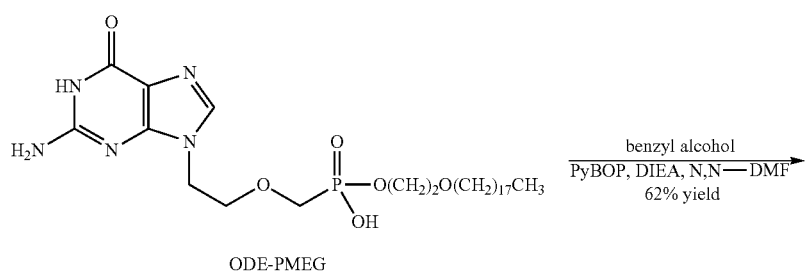

ODE-PMEG

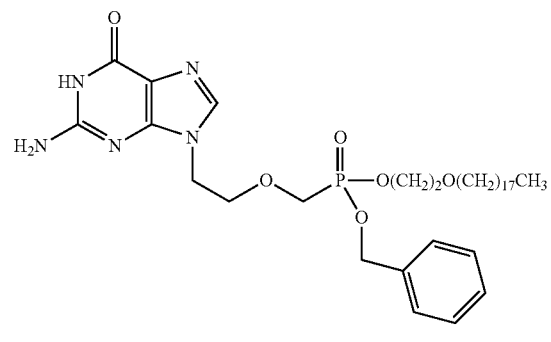

Bn-ODE-PMEG

To a solution of octadecyloxyethyl 9-[2-(phosphonomethoxy)ethyl]guanine (ODE-PMEG) [prepared according to: Valiaeva, N. et al.; *Antiviral Research*, 2006, 72:10-19] (0.21 g, 0.35 mmol), (benzotriazol-1-yloxy)-tripyrrolidinophosphonium hexafluorophosphate (PYBOP®, 0.27 g, 0.525 mmol) and anhydrous benzyl alcohol (0.05 ml, 0.525 mmol) in dry N,N-DMF, diisopropylethylamine (DIEA, 0.24 ml, 1.4 mmol) was added. The mixture was stirred at room temperature for 30 min. The solvents were evaporated in vacuo. The residue was dissolved in ethyl acetate (50 ml) and extracted with saturated sodium bicarbonate (2×10 ml). The ethyl acetate layer was evaporated, and then the residue was adsorbed on silica gel and purified by flash column chromatography. Elution with $CH_2Cl_2$/MeOH (0-5%) gave 0.15 g (62%) of Cmpd 1 as a white powder. $^1$H NMR ($CDCl_3$/methanol-$d_4$) δ 7.56 (s, 1H); 7.35-7.40 (m, 5H); 5.08 (dd, J=9 Hz, J1=2 Hz, 2H); 4.19 (t, J=7 Hz, 2H); 4.09-4.17 (m, 2H); 3.87 (t, J=5 Hz, 2H), 3.85 (dd, J=8 Hz, J1=2 Hz, 2H); 3.57 (t, J=5 Hz, 2H); 3.44 (t, J=7 Hz, 2H); 1.50-1.60 (m, 2H); 1.20-1.38 (m, 30H); 0.89 (t, J=7 Hz, 3H). MS (EI): 676.34 $(M+H)^+$, 698.41 $(M+Na)^+$.

Example 2

Resolution of benzyl octadecyloxyethyl 9-[2-(phosphonomethoxy) ethyl]guanine P-chiral enantiomers

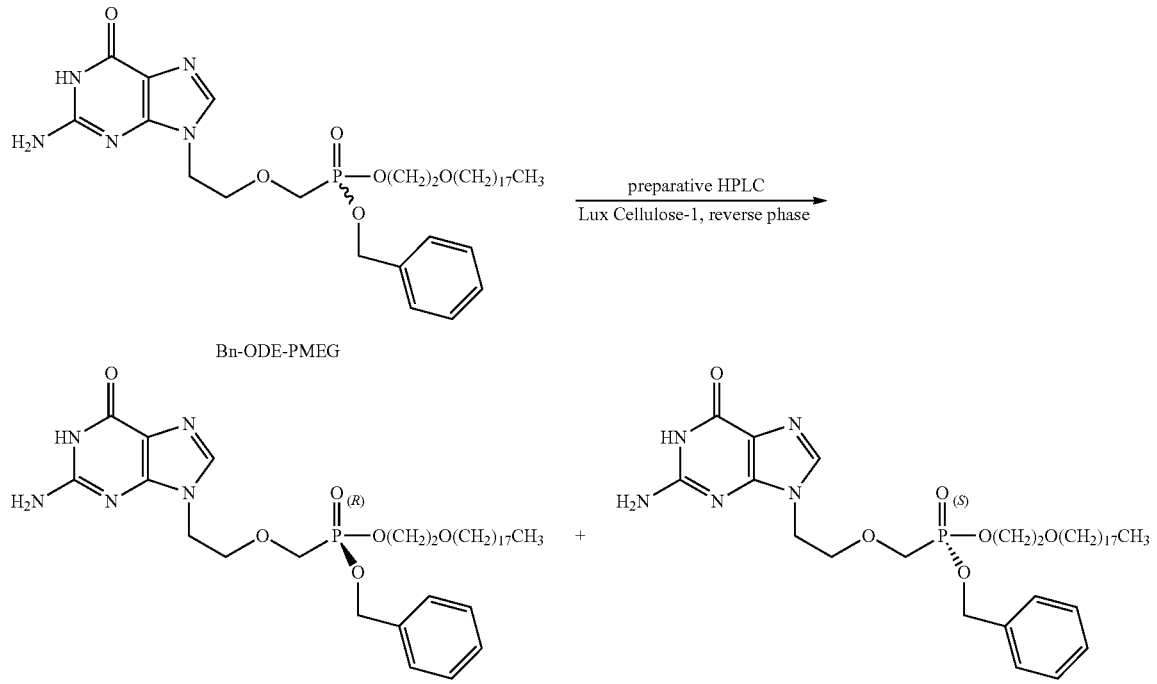

Bn-ODE-PMEG of Example 1 was obtained as a mixture of enantiomers because of the chirality at phosphorus. The enantiomers were separated on a Lux™ Cellulose-1 column (Phenomenex®, Torrance, Calif. USA) using reverse phase conditions (mobile phase of 50:50:0.1 20 mM AmmAc: AcN:TFA). The absolute stereochemistry of the P-chiral enantiomers was not determined. The preparative chromatographic resolution of the material obtained in Example 1 provided two enantiomers that are characterized as 1a (fast eluting enantiomer) and 1b (slow eluting enantiomer). An example chromatogram is provided in the FIGURE.

In the following examples, preparation of the racemic mixture is described, however, the method of Example 2, or modifications thereof known in the art, can be used to resolve each into optically active enantiomers or diastereomers as needed.

Example 3

Preparation of benzyl octadecyloxyethyl 9-[2-(phosphonomethoxy) ethyl]adenine (Cmpd 2, Bn-ODE-PMEA)

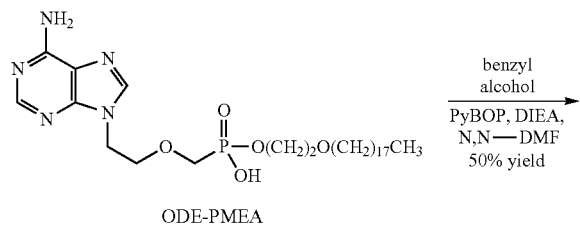

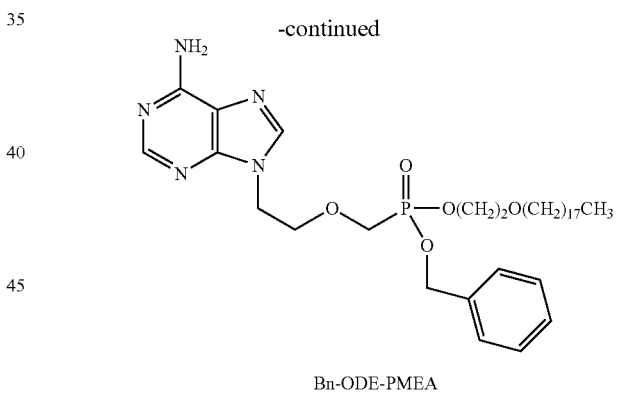

To a solution of octadecyloxyethyl 9-[2-(phosphonomethoxy)ethyl]adenine (ODE PMEA) [prepared according to: Valiaeva, N. et al. *Antiviral Research* 2006, 72:10-19] (0.2 g, 0.35 mmol), (benzotriazol-1-yloxy)-tripyrrolidino-phosphonium hexafluorophosphate (PYBOP®, 0.27 g, 0.525 mmol), anhydrous benzyl alcohol (0.05 ml, 0.525 mmol) in dry N,N-DMF, diisopropylethylamine (DIEA, 0.24 ml, 1.4 mmol) was added. The mixture was stirred at room temperature for 30 min. The solvents were evaporated. The residue was dissolved in ethyl acetate (50 ml) and washed with a saturated solution of sodium bicarbonate (2×10 ml). The ethyl acetate layer was evaporated, and then the residue was purified by column chromatography on silica gel using $CH_2Cl_2$/MeOH (0-5%) to give 0.12 g (50%) of compound 2. $^1$H NMR (CDCl$_3$/methanol-d$_4$) δ 8.25 (s, 1H); 7.99 (s, 1H); 7.30-7.40 (m, 5H); 5.07 (dd, J=9 Hz, J1=2

Hz, 2H); 4.38 (t, J=7 Hz, 2H); 4.08-4.18 (m, 2H); 3.88 (t, J=5 Hz, 2H), 3.83 (dd, J=8 Hz, J1=2 Hz, 2H); 3.56 (t, J=5 Hz, 2H); 3.42 (t, J=7 Hz, 2H); 1.50-1.60 (m, 2H); 1.20-1.38 (m, 30H); 0.88 (t, J=7 Hz, 3H). MS (EI): 660.55 (M+H)+.

Example 4

Preparation of benzyl octadecyloxyethyl 9-(S)-[3-hydroxy-2-(phosphonomethoxy)propyl] adenine (Cmpd 218, Bn-ODE-(S)-HPMPA)

Method 1:

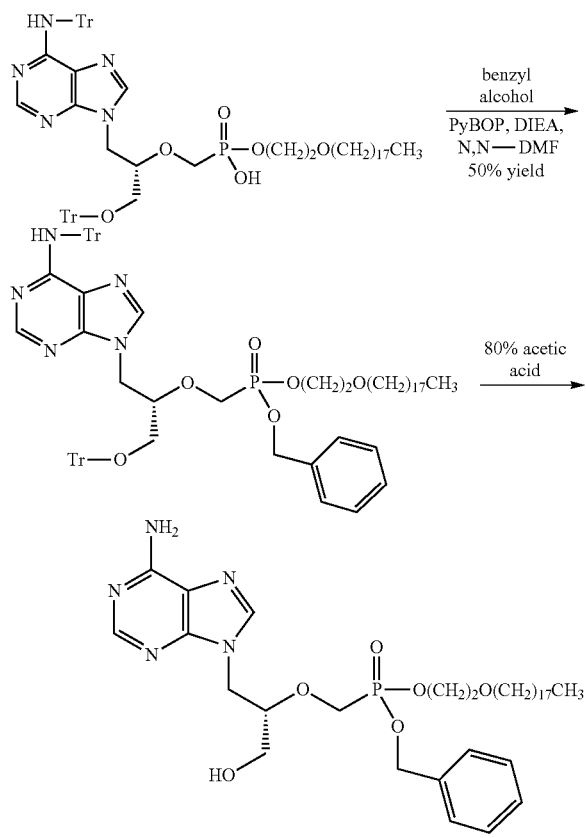

To a solution of octadecyloxyethyl 9-(S)-[3-trityloxy-2-(phosphonomethoxy) propyl]-N⁶-trityladenine (prepared as described in: Beadle, J. R. et al. *Journal of Medicinal Chemistry* 2006, 49:2010-2015) (0.42 g, 0.38 mmol), (benzotriazol-1-yloxy)-tripyrrolidinophosphonium hexafluorophosphate (PYBOP®, 0.30 g, 0.58 mmol), benzyl alcohol (0.06 ml, 0.58 mmol) in dry N,N-DMF (2 ml), diisopropylethylamine (DIEA, 0.4 ml, 1.52 mmol) was added. The mixture was stirred at room temperature for 30 min. The solvents were evaporated. The residue was dissolved in ethyl acetate (50 ml), and then washed with saturated solution of sodium bicarbonate (2×10 ml). Ethyl acetate was evaporated, and the residue was purified by column chromatography on silica gel using CH$_2$Cl$_2$/MeOH (0-5%) to give 0.23 g (51%) of the product. $^1$H NMR (CDCl$_3$/methanol-d$_4$) δ 7.89 (s, 1H); 7.16-7.40 (m, 36H); 5.03 (dd, J=9 Hz, J1=2 Hz, 2H); 4.27-4.44 (m, 2H); 4.06-4.14 (m, 1H); 3.91-4.04 (m, 2H), 3.83 (dd, J=8 Hz, J1=2 Hz, 2H); 3.40-3.50 (m, 2H); 3.27-3.40 (m, 4H); 1.42-1.58 (m, 2H); 1.18-1.38 (m, 30H); 0.88 (t, J=7 Hz, 3H). MS (EI): 1174.27 (M+H)+

The protected intermediate (0.13 g, 0.11 mmol) was added to 80% aq acetic acid (10 ml) and stirred at 30° C. for 3 h. After cooling, the solvent was evaporated and the residue was purified by column chromatography on silica gel to give compound 218 (0.04 g, 52% yield). $^1$H NMR (CDCl$_3$/methanol-d$_4$) δ 8.25 (s, 1H); 7.89 (s, 1H); 7.26-7.38 (m, 5H); 5.09 (dd, J=9 Hz, J1=2 Hz, 2H); 4.28-4.43 (m, 2H); 4.06-4.18 (m, 1H); 3.95-4.05 (m, 2H), 3.80 (dd, J=8 Hz, J1=2 Hz, 2H); 3.50-3.60 (m, 2H); 3.25-3.38 (m, 4H); 1.49-1.60 (m, 2H); 1.10-1.40 (m, 30H); 0.88 (t, J=7 Hz, 3H). MS (EI): 690.49 (M+H)+, 712.47 (M+H)+.

Method 2:

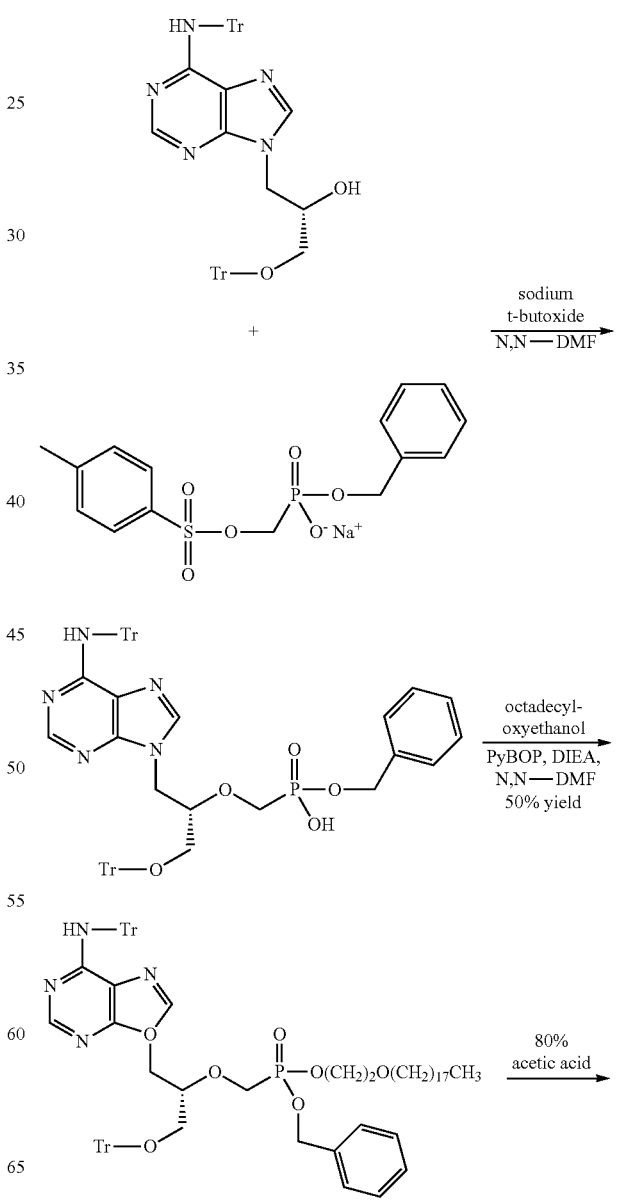

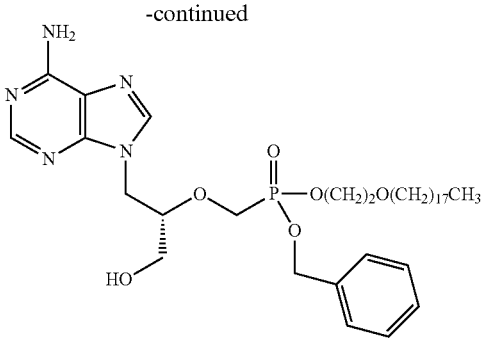

A mixture of 9-(S)-[3-trityloxy-2-hydroxypropyl]-N[6]-trityladenine [prepared as in: Webb, R. R., Nucleosides & Nucleotides, 1989, 8:619-24] (1.4 g, 2.0 mmol) and sodium tert-butoxide (0.39 g, 4 mmol) in dry N,N-DMF (10 ml) were stirred at room temperature for 30 min, then benzyl p-toluenesulfonyloxymethylphosphonate (0.94 g, 2.5 mmol, see Example 6) was added. The mixture was stirred at 80° C. overnight. The solvent was evaporated, and then the residue was purified by column chromatography on silica gel to give benzyl 9-(S)-[3-trityloxy-2-(phosphonomethoxy) propyl]-N[6]-trityladenine 0.75 g (42%). $^1$H NMR (CDCl$_3$/methanol-d$_4$) δ 8.09 (s, 1H); 7.88 (s, 1H); 7.08-7.60 (m, layer was evaporated, and then the residue was purified by column chromatography on silica gel using CH$_2$Cl$_2$/MeOH (0-5%) to give 0.15 g (58%) of the product. $^1$H NMR (CDCl$_3$/methanol-d$_4$) δ: 7.93 (s, 1H); 7.87 (s, 1H); 7.16-7.42 (m, 35H); 5.00 (dd, J=9 Hz, J$_1$=2 Hz, 2H); 4.27-4.44 (m, 2H); 4.06-4.14 (m, 1H); 3.91-4.04 (m, 2H), 3.83 (dd, J=8 Hz, J$_1$=2 Hz, 2H); 3.40-3.50 (m, 2H); 3.27-3.40 (m, 4H); 1.42-1.58 (m, 2H); 1.18-1.38 (m, 30H); 0.88 (t, J=7 Hz, 3H). MS (EI): 1174.29 (M+H)$^+$; 1196.52 (M+Na)$^+$.

The protected compound (0.15 g, 0.13 mmol) was treated with 80% aq acetic acid (10 ml) at 30° C. for 3 h. The solvents were evaporated, and then the residue was purified by column chromatography on silica gel to give compound 218 (0.06 g, 68%). $^1$H NMR (CDCl$_3$/methanol-d$_4$) δ: 8.24 (s, 1H); 7.52 (s, 1H); 7.34-7.38 (m, 5H); 5.06 (dd, J=9 Hz, J$_1$=2 Hz, 2H); 4.28-4.46 (m, 2H); 4.06-4.16 (m, 2H); 3.95-4.16 (m, 1H), 3.76-3.87 (m, 2H); 3.52-3.66 (m, 4H); 3.39-3.48 (m, 2H); 1.49-1.60 (m, 2H); 1.20-1.40 (m, 30H); 0.89 (t, J=7 Hz, 3H). MS (EI): 690.47 (M+H)$^+$, 712.45 (M+Na)$^+$.

Example 5

Preparation of isopropylidene glyceryl octadecyloxyethyl 9-(2-phosphonomethoxyethyl)guanine

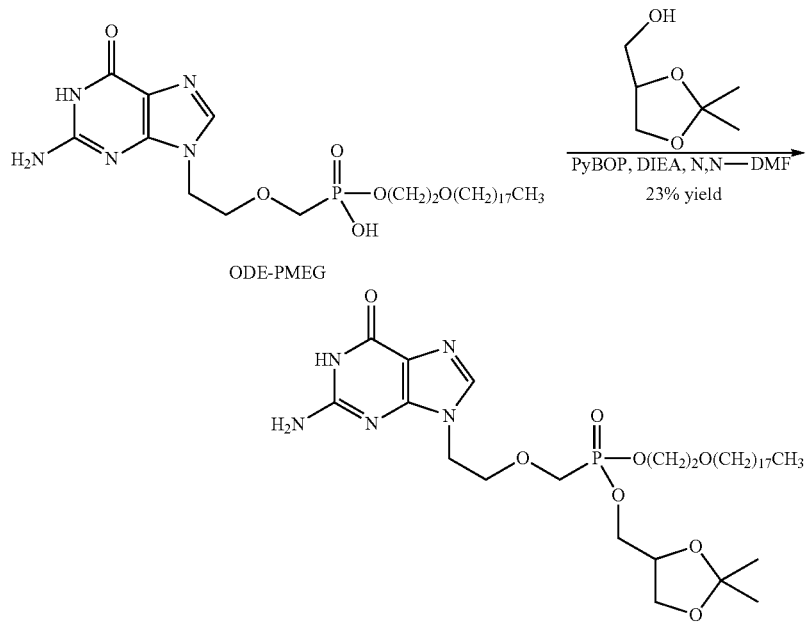

30H); 4.84-4.88 (m, 2H); 4.20-4.30 (m, 2H); 3.78-4.90 (m, 1H); 3.50-3.72 (m, 2H), 2.99-3.18 (m, 2H).

To a solution of this intermediate (0.2 g, 0.22 mmol), (benzotriazol-1-yloxy)-tripyrrolidinophosphonium hexafluorophosphate (PYBOP®, 0.17 g, 0.33 mmol) and octadecyloxyethanol (0.10 g, 0.33 mmol) in dry N,N-DMF (2 ml), diisopropylethylamine (DIEA, 0.15 ml, 0.88 mmol) was added. The mixture was stirred at room temperature for 30 min and the solvent was evaporated. The residue was dissolved in ethyl acetate (50 ml) and washed with saturated solution of sodium bicarbonate (2×10 ml). The ethyl acetate To a suspension of octadecyloxyethyl 9-[2-(phosphonomethoxy)ethyl]guanine (ODE PMEG)) [prepared according to: Valiaeva, N. et al.; Antiviral Research, 2006, 72:10-19] (0.18 g, 0.30 mmol), oxalyl chloride (0.56 ml, 0.48 mmol) in dry toluene (5 ml), DMF (0.06 ml) was added. The mixture was stirred at room temperature for 1 h. The solvent was evaporated in vacuum and co-evaporated with toluene (2×10 ml). The residue was dissolved in toluene (5 ml) and isopropylidene glycerol (0.09 g, 0.6 mmol) was added. The mixture was stirred at room temperature overnight. A solution of saturated sodium bicarbonate (5 ml) was added, and the mixture was stirred for 30 min. The toluene fraction was evaporated and purified by column chromatography on silica gel to give 0.05 g of IPG-ODE-PMEG (23%). $^1$H NMR (CDCl$_3$/methanol-d$_4$) δ: 8.91 (s, 1H); 8.15 (s, 1H); 4.44-4.52 (m, 2H); 4.18-4.34 (m, 2H); 4.13-4.18 (m, 1H); 4.02-4.13 (m, 2H); 3.95-4.18 (m, 2H); 3.68-3.84 (m, 2H); 3.60-3.67 (m, 2H); 3.44-3.52 (m, 2H); 1.42 (t, J=7 Hz, 3H); 1.36 (t, J=7 Hz, 3H); 1.22-1.34 (m, 30H), 0.89 (t, J=7 Hz, 3H). MS (EI): 700.37 (M+H)$^+$, 722.43 (M+Na)$^+$.

Example 6

Preparation of benzyl p-toluenesulfonyloxymethyl phosphonate, sodium salt

Diethyl p-toluenesulfonyloxymethyl phosphonate (3.2 g, 9.9 mmol) was dissolved in N,N-DMF (10 ml) and then bromotrimethylsilane (10 ml) was added. The mixture was stirred at room temperature overnight. The solvent was evaporated, and co-evaporated with toluene (2×10 ml). An ethanol/water mixture (10 ml) was added, and then mixture was stirred for 30 min at room temperature. The solvents were evaporated and co-evaporated with toluene (2×10 ml). The residue was suspended in toluene (50 ml), and then oxalyl chloride (1.3 ml, 15.0 mmol) was added followed by N,N-DMF (0.01 ml). The mixture was stirred at room temperature for 1 h. The solvents were evaporated and co-evaporated with toluene (2×10 ml). The residue was suspended in toluene (25 ml), and then anhydrous benzyl alcohol (1.5 ml, 15.0 mmol) was added. The mixture was stirred at room temperature overnight. A solution of saturated sodium bicarbonate (15 ml) was added, and then the mixture was stirred for 30 min. The toluene fraction was evaporated, and the residue was purified by column chromatography on silica gel to give 2.94 g of benzyl p-toluenesulfonyloxymethyl phosphonate, sodium salt (81%). $^1$H NMR (CDCl$_3$/methanol-d$_4$) δ: 7.72 (d, J=8 Hz, 2H); 7.30-7.33 (m, 7H); 4.88 (d, J=7 Hz, 2H); 4.02 (d, J=9 Hz, 2H); 2.44 (s, 3H).

Example 7

Preparation of benzyl 1-O-octadecyl-2-O-benzyl-sn-glyceryl 9-(S)-[(3-hydroxypropyl-2-phosphonomethoxy)propyl]adenine (Cmpd 230, Bn-ODBG-(S)-HPMPA)

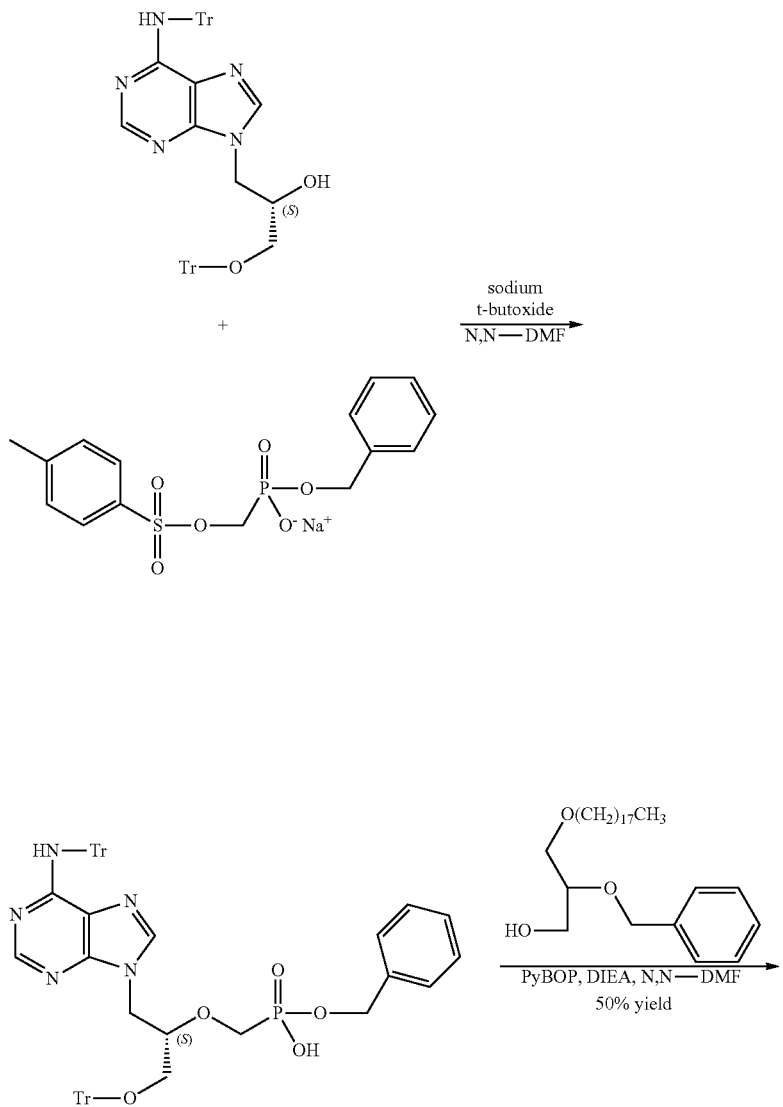

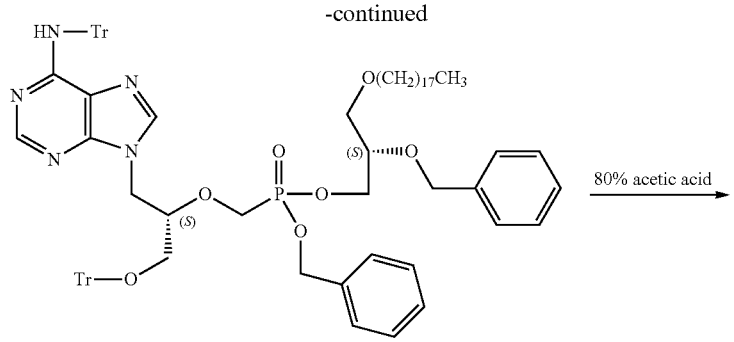

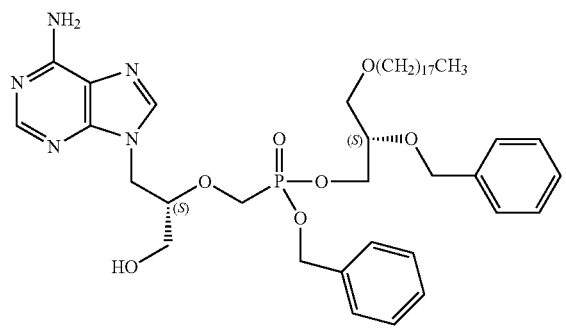

To a solution of benzyl 9-(S)-[3-trityloxy-2-(phosphonomethoxy)propyl]-N⁶-trityladenine (prepared as in Example 4, method 2) (0.4 g, 0.44 mmol), (benzotriazol-1-yloxy)-tripyrrolidinophosphonium hexafluorophosphate (PYBOP®, 0.27 g, 0.51 mmol), 1-O-octadecyl-2-O-benzyl-sn-glycerol (0.22 g, 0.51 mmol) in dry N,N-DMF (1 ml), diisopropylethylamine (DIEA, 0.30 ml, 1.7 mmol) was added. The mixture was stirred at room temperature for 30 min. The solvents were evaporated. The residue was dissolved in ethyl acetate (50 ml), and then washed with a solution of saturated sodium bicarbonate (2×10 ml). The ethyl acetate layer was evaporated and then the residue was purified by column chromatography on silica gel using CH₂Cl₂/MeOH (0-5%) to give 0.15 g (58%) of the product. ¹H NMR (CDCl₃/methanol-d₄) δ: 7.88 (s, 1H); 7.87 (s, 1H); 7.19-7.42 (m, 40H); 4.95-5.03 (m, 2H); 4.57-4.60 (m, 2H); 4.29-4.39 (m, 2H); 4.16-4.28 (m, 2H); 4.00-4.12 (m, 1H); 3.90-3.98 (m, 1H); 3.65-3.81 (m, 4H); 3.45-3.49 (m, 2H); 1.46-1.53 (m, 2H); 1.22-1.32 (m, 30H); 0.88 (t, J=7 Hz, 3H). MS (EI): 1294.27 (M+H)⁺; 1316.57 (M+Na)⁺.

The protected compound (0.33 g, 0.13 mmol) was treated with 80% aq acetic acid (20 ml) at 30° C. for 3 h. The solvents were then evaporated and the residue was purified by column chromatography on silica gel to give compound 230 (0.13 g, 65%). ¹H NMR (CDCl₃/methanol-d₄) δ: 8.22 (s, 1H); 7.65 (s, 1H); 7.27-7.35 (m, 10H); 4.99-5.04 (m, 2H); 4.58-4.66 (m, 2H); 4.33-4.43 (m, 1H); 4.16-4.33 (m, 2H), 3.94-4.12 (m, 2H); 3.80-3.88 (m, 1H); 3.68-3.78 (m, 2H); 3.38-3.62 (m, 4H); 1.50-1.58 (m, 2H); 1.22-1.38 (m, 30H); 0.89 (t, J=7 Hz, 3H). MS (EI): 810.47 (M+H)⁺, 832.44 (M+Na)⁺.

Example 8

Preparation of benzyl octadecyloxyethyl 1-(S)-[(3-hydroxy-2-phosphonomethoxy)propyl]cytosine (Cmpd 219, Bn-ODE-(S)-HPMPC)

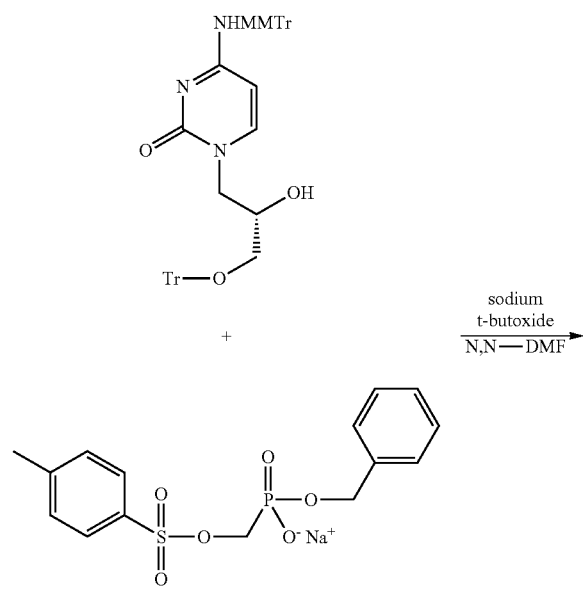

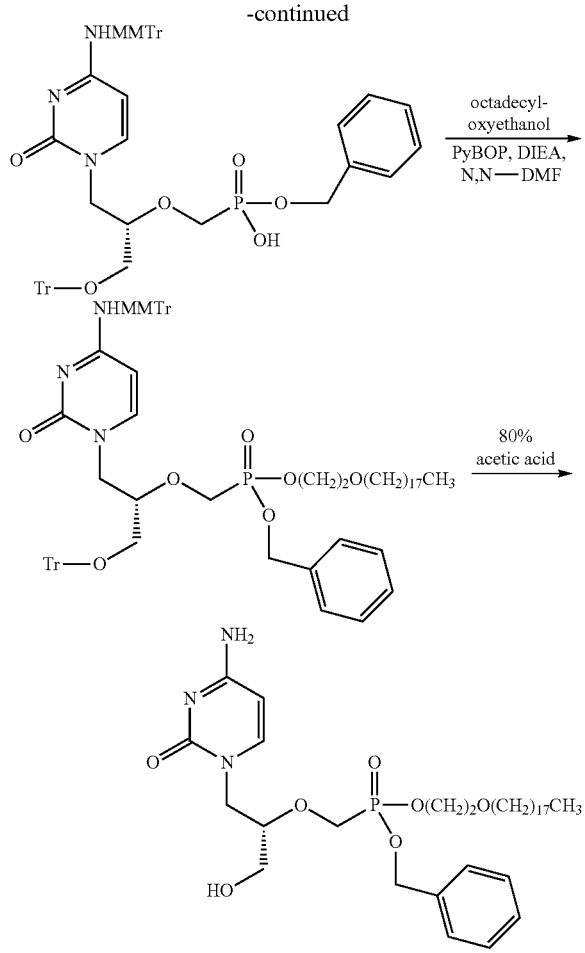

A mixture of 1-(S)-[3-trityloxy-2-hydroxypropyl]-N⁴-monomethoxytritylcytosine [prepared as described in: Beadle, J. R., et al., PCT Int. Appl. WO 2005/087788 A2, published Sep. 22, 2005] (1.84 g, 2.63 mmol) and sodium tert-butoxide (1.24 g, 3.29 mmol) in dry DMF (20 ml) were stirred at room temperature for 30 min. Benzyl p-toluenesulfonyloxymethylphosphonate (0.94 g, 2.5 mmol, see Example 6) were added and the mixture was stirred at 80° C. overnight. The solvent was evaporated, and the residue was purified by column chromatography on silica gel to give benzyl 1-(S)-[3-trityloxy-2-(phosphonomethoxy)propyl]-N⁴-monomethoxytritylcytosine 1.25 g (52%). ¹H NMR (CDCl₃/methanol-d₄) δ: 7.12-7.48 (m, 24H); 7.05 (d, J=9 Hz, 1H); 6.79 (d, J=9 Hz, 1H); 4.70 (dd, J₁=30 Hz, J₂=6 Hz, 2H); 4.20-4.30 (m, 2H); 3.78-4.90 (m, 1H); 3.77 (s, 3H); 3.50-3.72 (m, 2H), 2.99-3.18 (m, 2H). (EI): 883.99 (M+H)⁺, 906.22 (M+Na)⁺.

To a solution of this intermediate (0.6 g, 0.66 mmol), (benzotriazol-1-yloxy)-tripyrrolidinophosphonium hexafluorophosphate (PYBOP®, 0.52 g, 0.99 mmol), octadecyloxyethanol (0.31 g, 0.52 mmol) in dry DMF (5 ml), diisopropylethylamine (DIEA, 0.46 ml, 2.65 mmol) was added. The mixture was stirred at room temperature for 30 min and then the solvents were evaporated. The residue was dissolved in ethyl acetate (50 ml), and washed with saturated solution of sodium bicarbonate (2×10 ml). Ethyl acetate was evaporated, and the residue was purified by column chromatography on silica gel using CH₂Cl₂/MeOH (0-5%) to give the product. ¹H NMR (CDCl₃/methanol-d₄) δ: 7.18-7.44 (m, 34H); 7.13 (dd, J₁=14 Hz, J₂=7 Hz, 1H); 6.85 (dd, J₁=14 Hz, J₂=7 Hz, 1H); 5.00 (dd, J₁=8 Hz, J₂=3 Hz, 2H); 4.04-4.12 (m, 2H); 3.88-3.95 (m, 1H); 3.80 (s, 3H); 3.58-3.79 (m, 4H); 3.45-3.57 (m, 2H); 3.16-3.22 (m, 1H); 3.02-3.08 (m, 1H); 1.43-1.52 (m, 2H); 1.08-1.38 (m, 30H); 0.88 (t, J=7 Hz, 3H). (EI): 1180.10 (M+H)⁺, 1202.57 (M+Na)⁺.

The protected compound (0.44 g, 0.37 mmol) was treated with 80% acetic acid (20 ml) at 30° C. for 3 h. The solvents were evaporated, and the residue was purified by column chromatography to give compound 219 (0.16 g, 64%). ¹H NMR (CDCl₃/methanol-d₄) δ: 7.40-7.42 (m, 5H); 7.38 (dd, J₁=14 Hz, J₂=7 Hz, 1H); 5.73 (dd, J₁=14 Hz, J₂=7 Hz, 1H); 5.12 (dd, J₁=8 Hz, J₂=3 Hz, 2H); 4.10-4.20 (m, 2H), 3.99-4.10 (m, 2H), 3.50-3.80 (m, 7H), 3.40-3.50 (m, 2H); 1.50-1.62 (m, 2H), 1.20-1.40 (m, 30H), 0.89 (t, J=7 Hz, 3H). Mass spec (ESI): 666.54 (M+H)⁺, 688.52 (M+Na)⁺.

Example 9

Preparation of benzyl 1-O-octadecyl-2-O-benzyl-sn-glyceryl 1-(S)-[3-hydroxy-2-(phosphonomethoxy) propyl]cytosine (Cmpd 231, Bn-ODBG (S)-HPMPC)

To a solution of the intermediate from Example 8, benzyl 1-(S)-[3-trityloxy-2-(phosphonomethoxy)propyl] N⁴-monomethoxytrityl cytosine (0.57 g, 0.63 mmol), (benzotriazol-1-yloxy)-tripyrrolidinophosphonium hexafluorophosphate (PYBOP®, 0.49 g, 0.95 mmol) and 1-O-octadecyl-2-O-benzyl-sn-glycerol (0.41 g, 0.95 mmol) in dry DMF (5 ml), diisopropylethylamine (DIEA, 0.44 ml, 2.52 mmol) was added. The mixture was stirred at room temperature for 30 min. The solvents were evaporated. The residue was dissolved in ethyl acetate (50 ml) and washed with saturated solution of sodium bicarbonate (2×10 ml). Ethyl acetate was evaporated, and the residue was purified by column chromatography on silica gel using CH₂Cl₂/MeOH (0-5%) to give 0.30 g (36%) of the product. ¹H NMR (CDCl₃/methanol-d₄) δ: 7.19-7.45 (m, 39H); 7.15 (dd, J₁=14 Hz, J₂=7 Hz, 1H); 6.82 (dd, J₁=14 Hz, J₂=7 Hz, 1H); 5.00 (dd, J₁=8 Hz, J₂=3 Hz, 2H); 4.69-4.71 (m, 2H); 4.05 (s, 3H), 3.96-4.05 (m, 2H); 3.82-3.90 (m, 1H); 3.50-3.80 (m, 4H); 3.40-3.53 (m, 2H); 3.24-3.40 (m, 4H); 3.02-3.08 (m, 1H); 1.43-1.50 (m, 2H); 1.20-1.40 (m, 30H); 0.88 (t, J=7 Hz, 3H). (EI): 1301.06 (M+H)⁺, 1322.58 (M+Na)⁺.

The protected compound (0.30 g, 0.23 mmol) was then treated with 80% acetic acid (20 ml) at 30° C. for 3 h. The solvents were evaporated, and the residue was purified by column chromatography to give compound 231 (0.10 g, 55%). ¹H NMR (CDCl₃/methanol-d₄) δ: 7.31-7.40 (m, 10H); 7.28 (dd, J₁=14 Hz, J₂=7 Hz, 1H); 5.66 (dd, J₁=14 Hz, J₂=7 Hz, 1H); 5.07 (dd, J₁=8 Hz, J₂=3 Hz, 2H); 4.63-4.66 (m, 2H), 4.18-4.27 (m, 2H), 4.02-4.14 (m, 2H), 3.90-3.98 (m, 2H), 3.40-3.84 (m, 8H); 1.50-1.62 (m, 2H), 1.20-1.40 (m, 30H), 0.89 (t, J=7 Hz, 3H). Mass spec (ESI): 786.43 (M+H)⁺, 808.41 (M+Na)⁺.

Example 10

Preparation of phenyl octadecyloxyethyl 9-[2-(phosphonomethoxy)ethyl]guanine (Cmpd 19, Ph-ODE-PMEG)

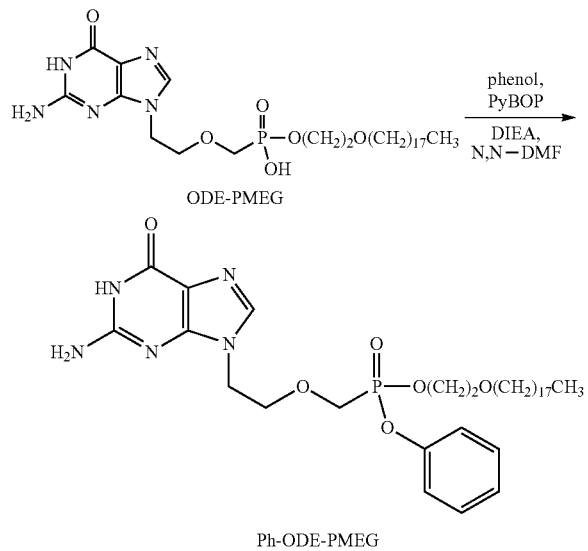

To a solution of octadecyloxyethyl 9-[2-(phosphonomethoxy)ethyl]guanine (ODE-PMEG, 0.26 g, 0.44 mmol) [prepared according to: Valiaeva, N. et al. *Antiviral Research* 2006, 72:10-19], (benzotriazol-1-yloxy)-tripyrrolidinophosphonium hexafluorophosphate (PYBOP®, 0.34 g, 0.66 mmol), and phenol (0.06 g, 0.66 mmol) in anhydrous N,N-DMF, was added diisopropylethylamine (DIEA, 0.30 ml, 1.8 mmol). The mixture was stirred at room temperature for 30 min, and then the solvent was evaporated in vacuo. The residue was dissolved in ethyl acetate (50 ml) and washed with saturated sodium bicarbonate (2×10 ml) solution. The ethyl acetate layer was evaporated, and the crude residue was purified by flash column chromatography on silica gel using $CH_2Cl_2$/MeOH (0-5%) to afford 0.09 g (31%) of compound 19 as a white powder. $^1$H NMR ($CDCl_3$/methanol-$d_4$) δ: 7.66 (s, 1H); 7.36 (t, J=8 Hz, 2H); 7.20 (t, J=7 Hz, 1H); 7.13 (d, J=8 Hz, 2H); 4.23-4.30 (m, 4H); 4.03 (dd, J=8 Hz, $J_1$=2 Hz, 2H); 3.93 (t, J=5 Hz, 2H); 3.61 (t, J=5 Hz, 2H), 3.41-3.45 (m, 2H); 1.50-1.60 (m, 2H); 1.20-1.38 (m, 30H); 0.89 (t, J=7 Hz, 3H). MS (EI): 662.43 $(M+H)^+$, 684.39 $(M+Na)^+$.

Example 11

Preparation of benzyl octadecyloxyethyl 9-(S)-[3-methoxy-2-(phosphonomethoxy)propyl]adenine (Cmpd 146, Bn-ODE-(S)-MPMPA)

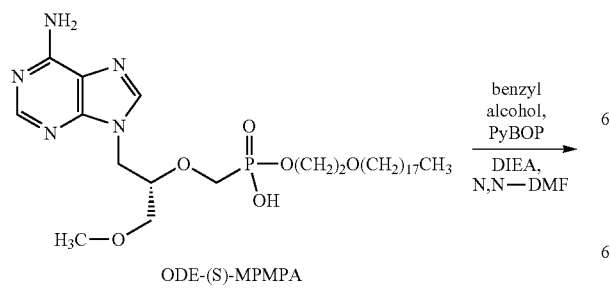

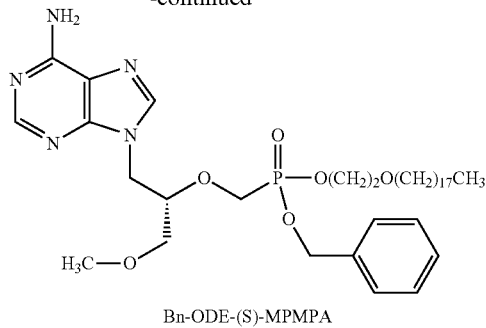

To a solution of octadecyloxyethyl 9-[3-methoxy-2-(phosphonomethoxy)propyl] adenine (ODE-S)-MPMPA, 0.62 g, 1.00 mmol) [prepared as described in: Valiaeva, N. et al. *Bioorganic & Medicinal Chemistry*, 2011, 19:4616-4625]), (benzotriazol-1-yloxy)-tripyrrolidinophosphonium hexafluorophosphate (PYBOP®, 0.78 g, 0.66 mmol), and benzyl alcohol (0.16 ml, 1.50 mmol) in anhydrous N,N-DMF, was added diisopropylethylamine (DIEA, 0.70 ml, 4.0 mmol). The mixture was stirred at room temperature for 30 min, and then solvents was evaporated in vacuo. The residue was dissolved in ethyl acetate (50 ml) and then washed with saturated $NaHCO_3$ (2×10 ml). The ethyl acetate layer was evaporated, and the residue was purified by flash column chromatography on silica gel using $CH_2Cl_2$/MeOH (0-5%) to give 0.29 g (41%) of compound 146. $^1$H NMR ($CDCl_3$/methanol-$d_4$) δ 8.24 (d, J=5.50 Hz, 1H), 8.05 (d, J=7.33 Hz, 1H), 7.30-7.39 (m, 5H), 5.00-5.15 (m, 2H); 4.40-4.45 (m, 1H); 4.28-4.36 (m, 1H); 4.00-4.18 (m, 3H); 3.80-3.98 (m, 2H); 3.40-3.60 (m, 6H); 3.35 (s, 3H); 1.45-1.60 (m, 2H), 1.22-1.36 (m, 30H), 0.89 (t, J=7 Hz, 3H). MS (EI): 704.52 $(M+H)^+$, 726.45 $(M+Na)^+$.

Example 12

Preparation of phenyl octadecyloxyethyl 9-(S)-[3-methoxy-2-(phosphonomethoxy)propyl]adenine (Cmpd 164, Ph-ODE-(S)-MPMPA)

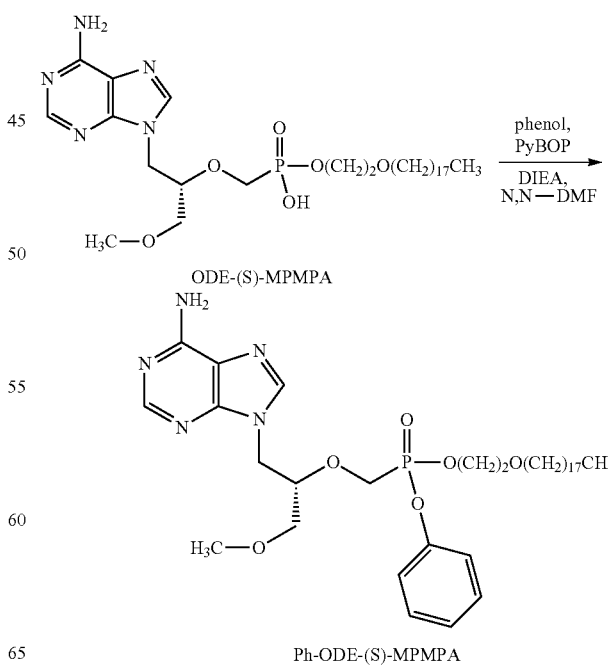

To a solution of octadecyloxyethyl 9-[3-methoxy-2-(phosphonomethoxy)propyl] adenine (ODE (S)-MPMPA, 0.62 g, 1.00 mmol) [prepared as described in: Valiaeva, N. et al. *Bioorganic & Medicinal Chemistry*, 2011, 19:4616-4625], (benzotriazol-1-yloxy)-tripyrrolidinophosphonium hexafluorophosphate (PYBOP®, 0.78 g, 0.66 mmol), and phenol (0.14 g, 1.50 mmol) in dry N,N-DMF, was added diisopropylethylamine (DIEA, 0.70 ml, 4.0 mmol). The mixture was stirred at room temperature for 30 min, and then the solvent was evaporated in vacuo. The residue was dissolved in ethyl acetate (50 ml), and then washed with saturated sodium bicarbonate (2×10 ml). The ethyl acetate layer was evaporated. The crude residue was purified by flash column chromatography on silica gel using $CH_2Cl_2$/MeOH (0-5%) to give 0.29 g (41%) of compound 164 as an off white solid. $^1$H NMR ($CDCl_3$/methanol-$d_4$) δ 8.23 (d, J=5.50 Hz, 1H), 8.05 (d, J=7.33 Hz, 1H), 7.29-7.37 (m, 2H), 7.20 (d, J=6.60 Hz, 1H), 7.12-7.16 (m, 1H), 7.08 (dt, J=8.71, 1.15 Hz, 1H), 4.30-4.45 (m, 2H), 4.11-4.28 (m, 3H), 3.98-4.07 (m, 2H), 3.42-3.63 (m, 6H), 3.34 (s, 3H), 1.48-1.59 (m, 2H), 1.22-1.36 (m, 30H), 0.89 (t, J=7 Hz, 3H). MS (D): 704.52 (M+H)$^+$, 726.45 (M+Na)$^+$.

Example 13

Preparation of benzyl hexadecyloxypropyl 9-[2-(phosphonomethoxy)ethyl]guanine (Cmpd 25, Bn-HDP-PMEG)

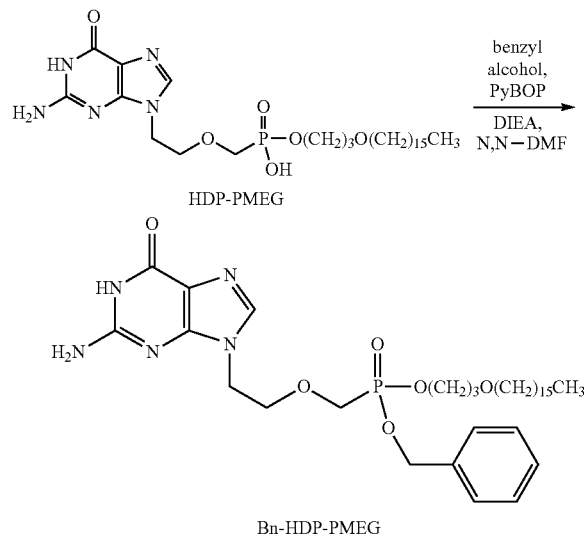

To a solution of hexadecyloxypropyl 9-[2-(phosphonomethoxy)propyl]guanine (HDP PMEG, 0.28 g, 0.49 mmol) [prepared according to: Valiaeva, N. et al., *Antiviral Research*, 2006, 72:10-19], (benzotriazol-1-yloxy)-tripyrrolidinophosphonium hexafluorophosphate (PYBOP®, 0.39 g, 0.74 mmol), and benzyl alcohol (0.10 ml, 0.74 mmol) in dry N,N-DMF, was added diisopropylethylamine (DIEA, 0.35 ml, 2.0 mmol). The mixture was stirred at room temperature for 30 min. The mixture was concentrated under vacuum. The resulting residue was dissolved in ethyl acetate (50 ml) and then washed with saturated sodium bicarbonate (2×10 ml). The ethyl acetate layer was evaporated, and the crude product was purified by flash column chromatography on silica gel using $CH_2Cl_2$/MeOH (0-5%) to give 0.03 g (10%) of compound 25 as a powdery white solid. $^1$H NMR ($CDCl_3$/methanol-$d_4$) δ: 7.62 (s, 1H), 7.30-7.44 (m, 5H), 5.07 (dd, J=8.98, 2.02 Hz, 2H), 4.05-4.24 (m, 4H), 3.83 (m, 4H), 3.31-3.42 (m, 4H), 1.87 (m, 2H), 1.54 (m, 2H), 1.17-1.38 (m, 26H), 0.86-0.91 (m, 3H). MS (EI): 662.46 (M+H)$^+$, 684.46 (M+Na)$^+$.

Example 14

Preparation of benzyl octadecyloxyethyl 9-(R)-[2-(phosphonomethoxy)propyl]adenine (Cmpd 74, Bn-ODE-(R)-PMPA)

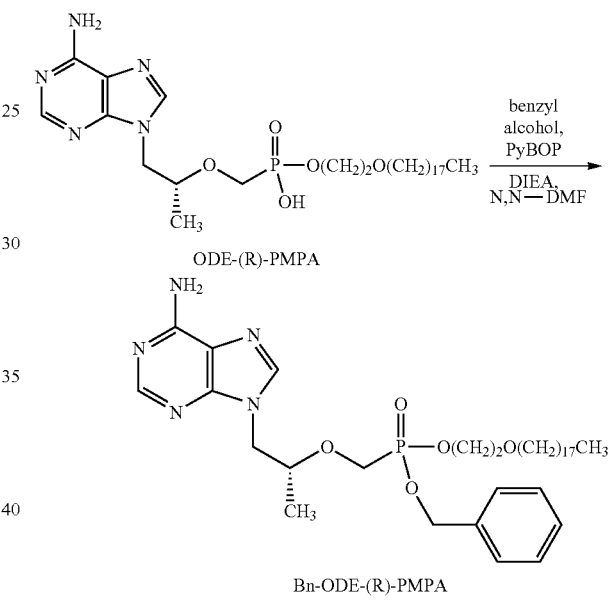

To a solution of octadecyloxyethyl 9-[2-(phosphonomethoxy)propyl]adenine (ODE-(R)-PMPA, 0.30 g, 0.51 mmol) [prepared as described in: Painter, G et al. *Antimicrobial Agents and Chemotherapy*, 2007, 51:3505-3509], (benzotriazol-1-yloxy)-tripyrrolidinophosphonium hexafluorophosphate (PYBOP®, 0.40 g, 0.77 mmol), and benzyl alcohol (0.08 ml, 0.77 mmol) in dry N,N-DMF, was added diisopropylethylamine (DIEA, 0.35 ml, 2.0 mmol). The mixture was stirred at room temperature for 30 min, and then the solvent was evaporated under vacuum. The resulting residue was dissolved in ethyl acetate (50 ml) and washed with saturated $NaHCO_3$ (2×10 ml). The ethyl acetate layer was evaporated, and the crude product was purified by flash column chromatography on silica gel using $CH_2Cl_2$/MeOH (0-5%) to give 0.24 g (70%) of compound 74. $^1$H NMR (400 MHz, $CDCl_3$+methanol-$d_4$) δ ppm 8.24 (s, 1H), 8.03 (d, J=4.40 Hz, 1H), 7.30-7.42 (m, 5H), 4.99-5.14 (m, 2H), 4.35 (d, J=14.66 Hz, 1H), 4.07-4.20 (m, 3H), 3.92 (ddd, J=13.75, 8.98, 4.77 Hz, 2H), 3.65-3.73 (m, 1H), 3.50-3.61 (m, 2H), 3.38-3.47 (m, 2H), 1.49-1.61 (m, 2H), 1.27 (m, 30H), 1.21 (d, J=6.23 Hz, 3H), 0.09 (t, J=8.00 Hz, 3H). MS (EI): 674.48 (M+H)$^+$, 693.46 (M+Na)$^+$.

Example 15

Preparation of phenyl octadecyloxyethyl 9-(R)-[2-(phosphonomethoxy)propyl]adenine (Cmpd 94, Ph-ODE-(R)-PMPA)

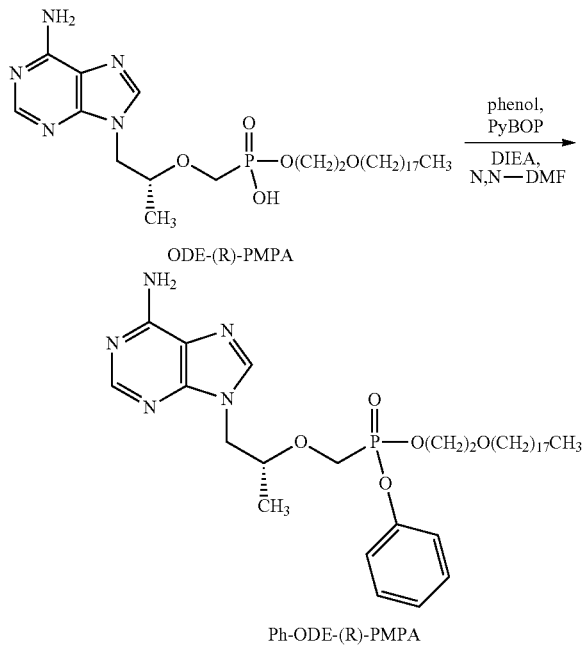

To a solution of octadecyloxyethyl 9-[2-(phosphonomethoxy)propyl]adenine (ODE PMPA, 0.30 g, 0.51 mmol) [prepared as described in: Painter, G et al. *Antimicrobial Agents and Chemotherapy*, 2007, 51:3505-3509], (benzotriazol-1-yloxy)-tripyrrolidinophosphonium hexafluorophosphate (PYBOP®, 0.40 g, 0.77 mmol), and phenol (0.072 g, 0.77 mmol) in dry N,N-DMF, was added diisopropylethylamine (DIEA, 0.35 ml, 2.0 mmol). The mixture was stirred at room temperature for 30 min, and then the solvent was evaporated under vacuum. The residue was dissolved in ethyl acetate (50 ml), and washed with saturated sodium bicarbonate solution (2×10 ml). The ethyl acetate layer was evaporated, and then the crude product was purified by column chromatography on silica gel using $CH_2Cl_2$/MeOH (0-5%) to afford 0.25 g (75%) of compound 94. $^1$H NMR (400 MHz, $CDCl_3$+methanol-$d_4$) δ ppm 8.24 (d, J=3.30 Hz, 1H), 8.05 (d, J=6.23 Hz, 1H), 7.29-7.37 (m, 2H), 7.17-7.24 (m, 1H), 7.05-7.15 (m, 2H), 4.37 (d, J=1.47 Hz, 1H), 4.04-4.31 (m, 4H), 3.94-4.03 (m, 1H), 3.86 (dd, J=9.53, 1.10 Hz, 1H), 3.60 (d, J=4.03 Hz, 2H), 3.38-3.47 (m, 2H), 1.48-1.60 (m, 2H), 1.21-1.35 (m, 33H), 0.89 (t, J=8.00 Hz, 3H). MS (EI): 660.47 (M+H)$^+$, 682.41 (M+Na)$^+$.

Example 16

Preparation of benzyl octadecyloxyethyl 9-(R)-[2-(phosphonomethoxy)propyl] guanine (Cmpd 73, Bn-ODE-(R)-PMPG)

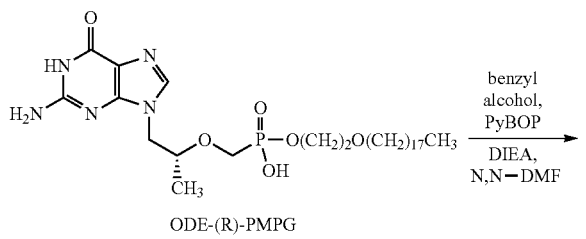

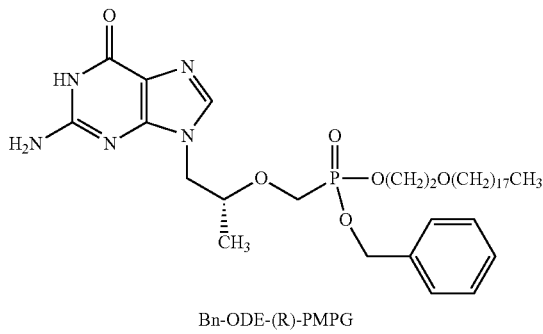

To a solution of octadecyloxyethyl 9-(R)-[2-(phosphonomethoxy)propyl]guanine (Bn-ODE-(R)-PMPG, 180 mg, 0.3 mmol) [prepared as described in: Painter, G et al. *Antimicrobial Agents and Chemotherapy*, 2007, 51:3505-3509], (benzotriazol-1-yloxy)-tripyrrolidinophosphonium hexafluorophosphate (PYBOP®, 312 mg, 0.6 mmol), and benzyl alcohol (97 mg, 0.9 mmol) in dry N,N-DMF (30 ml), was added diisopropylethylamine (DIEA, 77 mg, 0.6 mmol). The mixture was stirred at room temperature for 30 min, and then the solvent was evaporated under vacuum. The residue was dissolved in ethyl acetate (50 ml), and washed with saturated sodium bicarbonate solution (2×10 ml). The ethyl acetate layer was evaporated, and then the crude product was purified by column chromatography on silica gel using $CH_2Cl_2$/MeOH (0-5%) to afford 60 mg (29%) of compound 73. $^1$H NMR (400 MHz, CDCl3+methanol-$d_4$) δ ppm 7.82 (d, J=5.50 Hz, 1H), 7.75 (d, J=7.33 Hz, 1H), 7.43-7.53 (m, 2H), 7.33-7.43 (m, 3H), 5.01-5.17 (m, 1H), 4.07-4.18 (m, 2H), 3.82-4.03 (m, 2H), 3.69-3.81 (m, 1H), 3.51-3.64 (m, 1H), 3.44 (d, J=7.70 Hz, 1H), 3.36 (dt, J=3.30, 1.65 Hz, 3H), 1.54 (m, 2H), 1.21-1.35 (m, 30H), 1.18 (dd, J=6.23, 2.57 Hz, 3H), 0.88 (t, J=8.00 Hz, 3H). MS (EI): 690.49 (M+H)$^+$, 712.48 (M+Na)$^+$.

Example 17

Preparation of benzyl octadecyloxyethyl (S)-9-[3-fluoro-2-(phosphonomethoxy)propyl]guanine (Cmpd 289, Bn ODE-(S)-FPMPG)

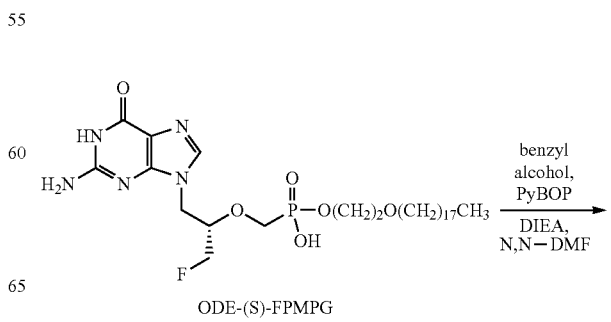

105

-continued

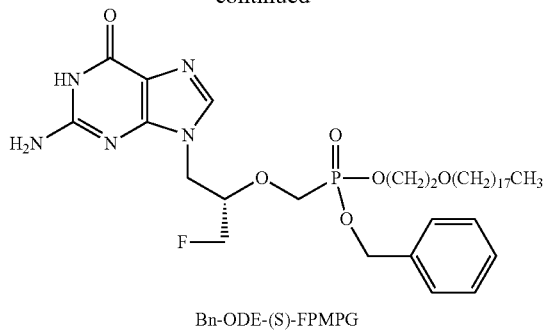

Bn-ODE-(S)-FPMPG 9-(S)-[3-Fluoro-2-(phosphonomethoxy)propyl]guanine [(S)-FPMPG, 0.32 g, 1.05 mmol) [prepared as described in: Jindřich, J. et al., *Collect. Czech. Chem. Commun.*, 1993, 58:1645-1667], was esterified with octadecyloxyethanol (0.33 g, 1.05 mmol) using N,N-dicyclohexylcarbodiimide (DCC, 0.43 g, 2.1 mmol) in dry N,N-DMF (25 ml) at 50° C. overnight. Octadecyloxyethyl (S)-9-[3-fluoro-2-(phosphonomethoxy)propyl]guanine (ODE(S)-FPMPG) was isolated by column chromatography to give 0.11 g (17%) of the product. $^1$H NMR (CDCl$_3$/methanol-d$_4$), δ 8.18 (s, 1H); 4.50-4.75 (m, 2H); 4.43-4.49 (m, 1H); 4.07-4.16 (m, 1H); 3.98-4.17 (m, 2H); 3.84-3.72 (m, 1H); 3.56-3.60 (m, 2H); 3.42-3.48 (m, 2H); 3.35-3.37 (m, 1H); 1.52-1.60 (m, 2H); 1.20-1.34 (m, 30H); 0.88 (t, J=7 Hz, 3H). MS (EI): 600.30 (M−H)$^-$.

A stirred mixture of ODE-(S)-FPMPG (0.11 g, 0.18 mmol), benzyl alcohol (0.06 ml, 0.54 mmol) and (benzotriazol-1-yloxy)-tripyrrolidinophosphonium hexafluorophosphate (PYBOP®, 0.28 g, 0.54 mmol) in dry DMF was treated with diisopropylethylamine (DIEA, 0.25 ml, 1.44 mmol) for 4 hours at room temperature. The solvent was evaporated under vacuum. The residue was dissolved in ethyl acetate (50 ml), and washed with saturated sodium bicarbonate solution (2×10 ml). The ethyl acetate layer was evaporated, and then the crude product was purified by column chromatography on silica gel using CH$_2$Cl$_2$/MeOH (0-5%) to afford 90 mg (71%) of compound 289. $^1$H NMR (400 MHz, CDCl$_3$+methanol-d$_4$) δ ppm 7.77 (s, 1H), 7.46-7.54 (m, 2H), 7.34-7.42 (m, 3H), 5.04-5.17 (m, 1H), 4.42-4.52 (m, 2H), 4.19-4.38 (m, 2H), 4.09-4.19 (m, 2H), 3.88-4.06 (m, 2H), 3.64-3.73 (m, 1H), 3.55-3.64 (m, 1H), 3.41-3.50 (m, 1H), 3.18 (d, J=7.33 Hz, 1H), 1.49-1.60 (m, 2H), 1.21-1.35 (m, 30H), 0.88 (t, J=7 Hz, 3H). MS (EI): 708.50 (M−H)$^-$, 730.52 (M+Na)$^+$.

Example 18

Preparation of naphthyl octadecyloxyethyl 9-(S)-[3-methoxy-2-(phosphonomethoxy)propyl]adenine (Cmpd 398, Npt-ODE-(S)-MPMPA)

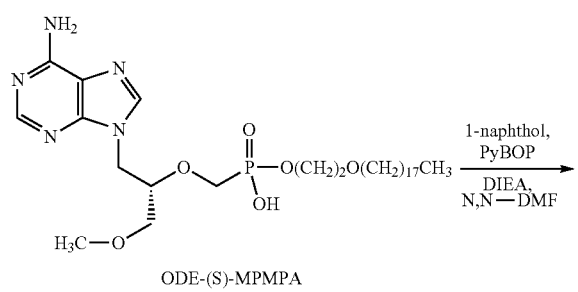

ODE-(S)-MPMPA

106

-continued

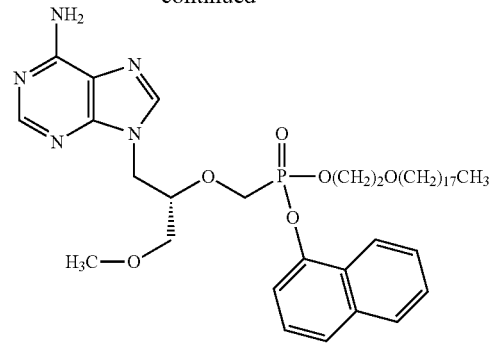

Npt-ODE-(S)-MPMPA

To a solution of octadecyloxyethyl 9-[3-methoxy-2-(phosphonomethoxy) propyl]adenine (ODE MPMPA, 0.30 g, 0.49 mmol) [prepared as described in: Valiaeva, N. et al. *Bioorganic & Medicinal Chemistry*, 2011, 19: 4616-4625], (benzotriazol-1-yloxy)-tripyrrolidinophosphonium hexafluorophosphate (PYBOP®, 0.38 g, 0.73 mmol), and 1-naphthol (0.11 g, 0.73 mmol) in dry N,N-DMF, was added diisopropylethylamine (DIEA, 0.35 ml, 2.0 mmol). The mixture was stirred at room temperature overnight, and then the solvent was evaporated under vacuum. The residue was dissolved in ethyl acetate (50 ml) and washed with saturated sodium bicarbonate (2×10 ml). The ethyl acetate layer was evaporated, and then the crude product was purified by column chromatography on silica gel using CH$_2$Cl$_2$/MeOH (0-5%) to yield 0.20 g (56%) of compound 398 as an off white solid. $^1$H NMR (400 MHz, CDCl$_3$+methanol-d$_4$) δ ppm 8.18 (d, J=8.07 Hz, 1H), 8.02-8.11 (m, 1H), 7.94 (s, 1H), 7.86-7.90 (m, 1H), 7.69-7.74 (m, 1H), 7.48-7.57 (m, 2H), 7.34-7.43 (m, 2H), 4.38-4.46 (m, 1H), 4.26-4.37 (m, 3H), 4.09-4.24 (m, 2H), 3.99-4.09 (m, 1H), 3.59 (t, J=4.58 Hz, 1H), 3.47-3.56 (m, 2H), 3.30-3.45 (m, 5H), 1.49 (d, J=6.60 Hz, 2H), 1.19-1.34 (m, 30H), 0.85-0.93 (t, J=7 Hz, 3H). MS (EI): 740.54 (M+H)$^+$, 762.52 (M+Na)$^+$.

Example 19

Preparation of naphthyl octadecyloxyethyl 9-[2-(phosphonomethoxy) ethyl]guanine (Cmpd 361, Npt-ODE-PMEG)

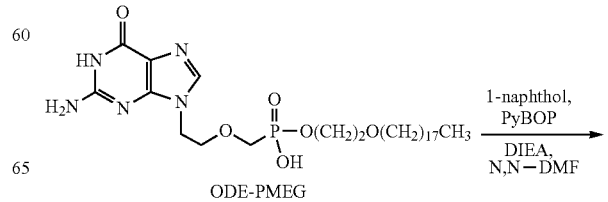

ODE-PMEG

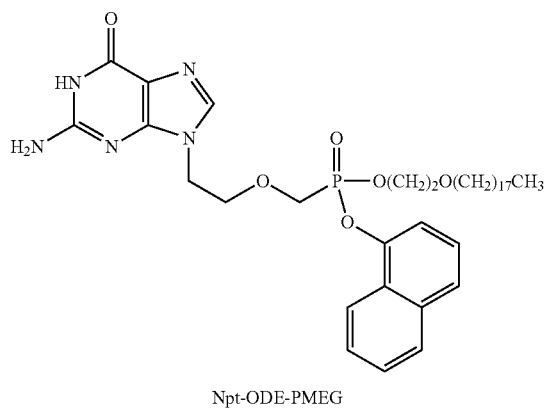

Npt-ODE-PMEG

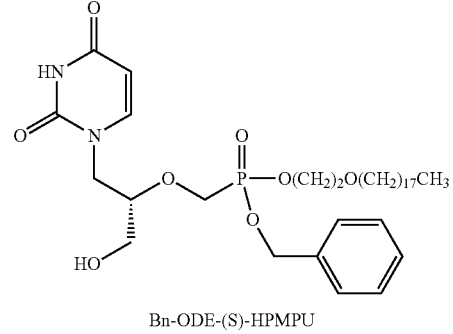

Bn-ODE-(S)-HPMPU

To a solution of octadecyloxyethyl 9-[2-(phosphonomethoxy)ethyl]guanine (ODE PMEG, 0.29 g, 0.50 mmol) [prepared according to: Valiaeva, N. et al. *Antiviral Research* 2006, 72: 10-19], (benzotriazol-1-yloxy)-tripyrrolidinophosphonium hexafluorophosphate (PYBOP®, 0.39 g, 0.75 mmol), and 1-naphthol (0.11 g, 0.75 mmol) in dry N,N-DMF, was added diisopropylethylamine (DIEA, 0.35 ml, 2.0 mmol). The mixture was stirred at room temperature overnight and then the solvent was evaporated under vacuum. The residue was dissolved in ethyl acetate (50 ml) and then washed with saturated sodium bicarbonate (2×10 ml). The ethyl acetate layer was evaporated. The crude product was purified by flash column chromatography on silica gel using $CH_2Cl_2$/MeOH (0-5%) to give 0.23 g (65%) of compound 361. $^1$H NMR (CDCl$_3$/methanol-d$_4$) δ: $^1$H NMR (400 MHz, CDCl$_3$+methanol-d$_4$) δ ppm 8.07-8.12 (m, 1H), 7.87 (dd, J=5.87, 3.30 Hz, 1H), 7.71 (d, J=5.87 Hz, 1H), 7.59 (d, J=4.40 Hz, 1H), 7.52-7.56 (m, 1H), 7.39-7.43 (m, 1H), 4.30 (ddd, J=8.62, 5.68, 3.30 Hz, 2H), 4.16-4.21 (m, 2H), 4.14 (d, J=8.07 Hz, 2H), 3.64-3.72 (m, 2H), 3.56-3.61 (m, 1H), 3.38 (d, J=4.77 Hz, 1H), 3.19 (q, J=7.45 Hz, 2H), 1.45-1.54 (m, 2H), 1.15-1.35 (m, 30H), 0.88 (t, J=7 Hz, 3H). MS (EI): 712.49 (M+H)$^+$, 734.41 (M+Na)$^+$.

Example 20

Preparation of benzyl octadecyloxyethyl 9-(S)-[3-hydroxy-2-(phosphonomethoxy)propyl]uracil (Cmpd 221, Bn-ODE-(S)-HPMPU)

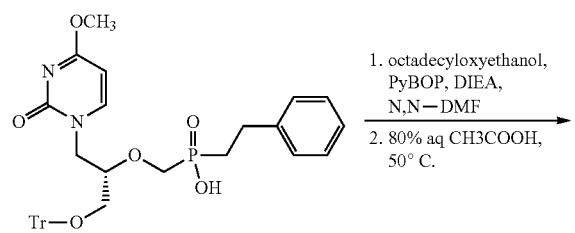

To a solution of benzyl 9-[3-trityloxy-2-(phosphonomethoxy)propyl]-4-methoxy-uracil (0.1 g, 0.15 mmol), (benzotriazol-1-yloxy)-tripyrrolidinophosphonium hexafluorophosphate (PYBOP®, 0.11 g, 0.20 mmol), and octadecyloxyethanol (0.06 g, 0.20 mmol) in dry N,N-DMF was added diisopropylethylamine (DIEA, 0.03 ml, 0.20 mmol). The mixture was stirred at room temperature overnight. The solvent was evaporated under vacuum. The residue was dissolved in ethyl acetate (50 ml), washed with saturated sodium bicarbonate (2×10 ml), and then the ethyl acetate layer was concentrated under vacuum. The resulting crude product was purified by flash column chromatography on silica gel using $CH_2Cl_2$/MeOH (0-5%) to give 0.024 g (17%) of benzyl octadecyloxyethyl 9-[3-trityloxy-2-(phosphonomethoxy)propyl]-4-methoxyuracil $^1$H NMR (400 MHz, CDCl$_3$+methanol) δ ppm 7.56 (d, J=5.50 Hz, 1H), 7.16-7.51 (m, 15H), 5.46 (d, J=5.50 Hz, 1H), 5.10 (d, J=8.80 Hz, 2H), 4.03-4.21 (m, 2H), 3.86-3.99 (m, 1H), 3.65-3.85 (m, 2H), 3.37-3.60 (m, 4H), 3.25 (s, 3H), 3.12 (m, 1H), 1.42-1.62 (m, 2H), 1.5-1.38 (m, 30H), 0.88 (t, J=6.97 Hz, 3H). MS (EI): 945.66 (M+Na)$^+$.

The protected intermediate was then stirred in 80% aq acetic acid overnight at 50° C. The solvent was then evaporated under vacuum, and the residue was purified by flash column chromatography to give 0.01 g (59%) of compound 221. MS (EI): 667.54 (M+H)$^+$, 689.56 (M+Na)$^+$.

Example 21

Preparation of ethyl octadecyloxyethyl 9-(S)-[3-methoxy-2-(phosphonomethoxy)propyl]adenine (Cmpd 182, Et-ODE-(S)-MPMPA)

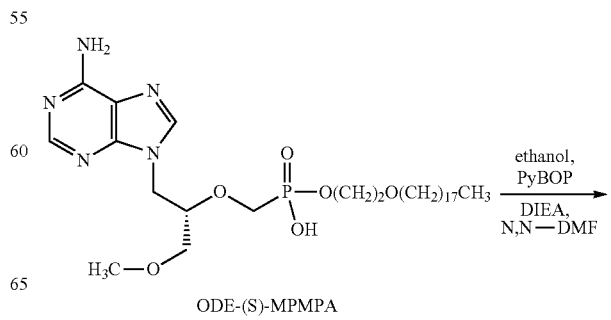

ODE-(S)-MPMPA

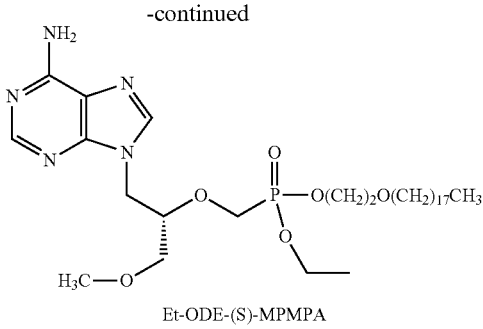

Et-ODE-(S)-MPMPA

To a solution of octadecyloxyethyl 9-(S)-[3-methoxy-2-(phosphonomethoxy) propyl]-adenine (ODE-(S)-MPMPA, 0.30 g, 0.49 mmol) [prepared as described in: Valiaeva, N. et al. *Bioorganic & Medicinal Chemistry*, 2011, 19:4616-4625], (benzotriazol-1-yloxy)-tripyrrolidinophosphonium hexafluorophosphate, (PYBOP®, 0.38 g, 0.73 mmol), in ethanol (25 ml), was added diisopropylethylamine (DIEA, 0.35 ml, 2.0 mmol). The mixture was stirred at room temperature overnight. The solvent was then evaporated under vacuum. The residue was dissolved in ethyl acetate (50 ml), and then washed with saturated sodium bicarbonate (2×10 ml). Ethyl acetate was evaporated, and the residue was purified by flash column chromatography on silica gel using $CH_2Cl_2$/MeOH (0-5%) to give 0.26 g (84%) of compound 182 as a white solid. $^1$H NMR (400 MHz, $CDCl_3$+methanol-$d_4$) δ ppm 8.26 (s, 1H), 8.08 (d, J=2.20 Hz, 1H), 4.72-4.74 (m, 1H), 4.62-64 (m, 1H), 4.44-4.50 (m, 1H), 4.28-4.35 (m, 1H), 4.10-4.18 (m, 2H), 4.03-4.10 (m, 2H), 3.81-3.89 (m, 1H), 3.53-3.64 (m, 3H), 3.42-3.52 (m, 3H), 3.40 (s, 3H), 1.56 (m, 2H), 1.19-1.37 (m, 33H), 0.89 (t, J=7.20 Hz, 3H). MS (EI): 642.69 (M+H)$^+$, 664.61 (M+Na)$^+$.

Example 22

Preparation of benzyl octadecyloxyethyl 9-[3-methoxy-2-(phosphonomethoxy)propyl]-2,6-diaminopurine (Cmpd 150, Bn-ODE(S)-MPMPDAP)

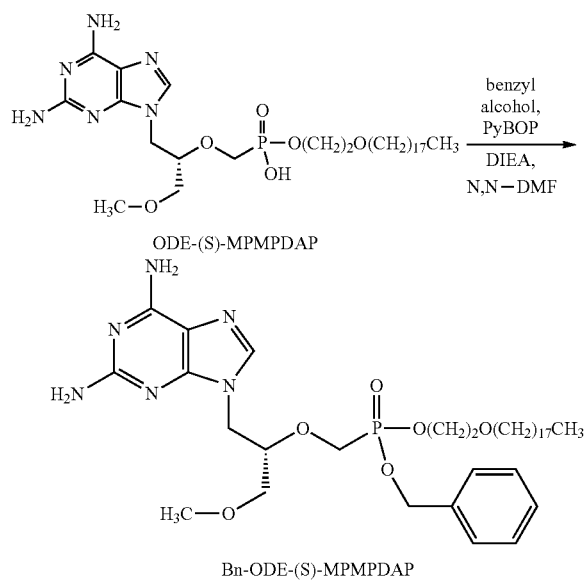

Bn-ODE-(S)-MPMPDAP

To a solution of octadecyloxyethyl 9-(S)-[3-methoxy-2-(phosphonomethoxy) propyl]-2,6-diaminopurine (ODE-(S)-MPMP DAP, 0.20 g, 0.32 mmol) [prepared as described in: Valiaeva, N. et al. *Bioorganic & Medicinal Chemistry*, 2011, 19:4616-4625], ((benzotriazol-1-yloxy)-tripyrrolidinophosphonium hexafluorophosphate (PYBOP®) (0.21 g, 0.40 mmol), and benzyl alcohol (0.04 ml, 0.40 mmol) in dry N,N-DMF, was added diisopropylethylamine (DIEA, 0.07 ml, 0.40 mmol). The mixture was stirred at room temperature overnight, and then the solvent was evaporated under vacuum. The residue was dissolved in ethyl acetate (50 ml), and then washed with saturated sodium bicarbonate (2×10 ml). The ethyl acetate layer was evaporated, and then the residue was purified by flash column chromatography on silica gel using $CH_2Cl_2$/MeOH (0-5%) to give 0.12 g (54%) of compound 150. $^1$H NMR (400 MHz, $CDCl_3$+methanol-$d_4$) δ ppm 7.63-7.68 (m, 1H), 7.31-7.43 (m, 5H), 5.02-5.13 (m, 2H), 4.59 (s, 1H), 4.50 (s, 1H), 4.23 (d, J=3.67 Hz, 1H), 3.99-4.15 (m, 3H), 3.84-3.92 (m, 2H), 3.39-3.56 (m, 5H), 3.36 (s, 3H), 1.49-1.58 (m, 2H), 1.17-1.35 (m, 30H), 0.89 (t, J=6.6 Hz, 3H). MS (EI): 719.62 (M+H)$^+$, 741.56 (M+Na)$^+$.

Example 23

Antiproliferative Activity of Nucleoside Phosphonates Diesters in Normal Human Fibroblasts and in Human Cervical Cancer Lines In Vitro Method.

Compounds at a range of concentrations were incubated with normal fibroblasts or human cervical cancer cell lines in monolayer culture and after 4 days, viable cell number was determined by neutral red reduction as previously described (Valiaeva N, et al., *Chemotherapy*, 2010, 56(1): 54-9). Cell lines were obtained from American Type Culture Collection. The results were plotted and the concentration which reduced neutral red levels by 50% ($CC_{50}$) was determined in triplicate. Although viral replication is no longer occurring in the human cervical cancer cell lines, Caski cells were transformed by HPV-16 and Hela cells were transformed by HPV-18.

Results.

As tabulated in Table 11 following, these results demonstrate that compounds described herein were 23.6 fold (e.g., Cmpd 219) to 3,750 fold (e.g., Cmpd 1) more effective in reducing viable cell number in the cervical cancer lines than in normal, non-transformed human fibroblasts.

TABLE 11

Antiproliferative activity of nucleoside phosphonate diesters in normal human fibroblasts and in human cervical cancer lines in vitro

| | Cytotoxic concentration 50% ($CC_{50}$) μM | | |
|---|---|---|---|
| Compound # | Normal human fibroblasts (HFF) | Caski (HPV-16) | Hela (HPV-18) |
| 219 | 52 | 2.0 | 2.2 |
| 218 | 5.2 | 0.055 | 0.029 |
| 1 | 15 | 0.004 | 0.009 |

Example 24

Antiproliferative Activity of Compounds on Human T Cell Leukemia Cells (MT-2)

Method of Cytotoxicity Determination.

MT-2 cells were incubated with drug for 72 hrs and harvested. Flow count beads (Beckman Coulter, Miami, Fla.) were added to the cell suspension followed by propidium iodide staining and analysis using flow cytometer and the 50% cytotoxic concentration ($CC_{50}$) was calculated from the cell counts and viability.

Results.

Compounds disclosed herein are effective antiproliferative agents in human T cell leukemia (MT-2) cells (Table 12).

TABLE 12

Antiproliferative activity in human MT-2 leukemic cells in vitro

| Compound # | $CC_{50}$, 50% Cytotoxic concentration μMMT2 cells T cell leukemia |
|---|---|
| 1 | 0.036 ± 0.04 |
| 1a | <0.01 |
| 1b | <0.01 |
| 2 | <0.010 |

Example 25

Anti HIV Activity

Method HIV Antiviral Assays.

MT-2 cells were maintained in RPMI 1640 supplemented with 10% FBS, 10 mM HEPES buffer, 50 IU of penicillin/ml, and 50 μg of streptomycin/ml. The antiviral activity of each compound was determined by inoculating MT-2 cells with $HIV-1_{LAI}$ at a multiplicity of infection (MOI) of 0.001 $TCID_{50}$/cell, followed by incubation in the presence of threefold serial drug dilutions (three wells per dilution). Four days after infection, culture supernatants were harvested, lysed with 0.5% Triton X-100, and assayed for p24 antigen concentration using a commercial ELISA assay (Perkin Elmer Life Sciences, Boston, Mass.). The antiviral activity of each compound is expressed as the $EC_{50}$, which is the concentration required to inhibit p24 antigen production by 50%.

Method Cytotoxicity Determination.

MT-2 cells were incubated with drug for 72 hrs and harvested. Flow count beads (Beckman Coulter, Miami, Fla.) were added to the cell suspension followed by propidium iodide staining and analysis using flow cytometer and the 50% cytotoxic concentration ($CC_{50}$) was calculated from the cell counts and viability.

Results.

Table 13 shows that compounds disclosed herein have considerable antiviral activity against HIV-1 and exhibit selectivity.

TABLE 13

Antiviral activity in HIV-1 infected human lymphoblastic leukemia cells

| | HIV ANTIVIRAL ACTIVITY IN MT-2 CELLS | | |
|---|---|---|---|
| Compound # | $EC_{50}$, μM | $CC_{50}$, μM | Selectivity Index |
| 1 | $<1 \times 10^{-5}$ | 0.036 ± 0.04 | >3600 |
| 2 | $<1 \times 10^{-5}$ | $<1 \times 10^{-2}$ | — |
| 218 | 0.13 ± 0.14 (3) | 2.3 ± 1.6 (3) | 17.7 |
| 219 | 2.7 ± 2.1 (3) | 18 ± 3.6 (3) | 6.7 |
| 230 | 0.05 ± 0.03 (3) | 19 ± 2.6 (3) | 380 |
| 231 | 2.2 ± 2.1 (3) | 22 ± 3.0 (3) | 10 |

$EC_{50}$, effective dose 50%; $CC_{50}$, cytotoxic dose 50%, selectivity index $CC_{50}/EC_{50}$. Assay: p24 reduction.

Example 26

Antiviral Effect of ANP Diesters in HFF Cells Infected with HSV-2

Method.

Primary low passage human foreskin fibroblast (HFF) cells in 96-well plates were infected at an MOI of 0.01 PFU/cell with the G strain of herpes simplex virus type 2 and incubated for 3 days. Media was then aspirated and cell monolayers were stained with crystal violet and rinsed with distilled water. Crystal violet associated with the cells was then quantified in a spectrophotometer and the concentration of the compound that was sufficient to reduce virus replication by 50% ($EC_{50}$) was calculated. Cytotoxicity was measured in parallel by similar methods to yield the concentration that reduced cell number by 50% ($CC_{50}$).

Results.

Results are tabulated in Table 14 following.

TABLE 14

Antiviral Effect of ANP diesters in HFF cells infected with HSV-2

| Compound # | $EC_{50}$, μM | $CC_{50}$, μM | Selectivity Index |
|---|---|---|---|
| 219 | 0.10 | 13.1 | 131 |
| 218 | 0.04 | 6.91 | 173 |
| 231 | 0.80 | 34.8 | 43.5 |
| 230 | 0.71 | 37.1 | 52.2 |
| 221 | 3.8 | >10 | >2.6 |

Example 27

Effect of Oral Octadecyloxyethyl-Benzyl-(ODE-Bn) Acyclic Nucleoside Phosphonate Diesters and ODE-Monoesters of Acyclic Nucleoside Phosphonates on Body Weight in Balb-c Mice Method.

Compounds were administered at the indicated doses by oral gavage daily for 5 days. Weights measured before and on day 6 after 5 doses.

Results.

As tabulated in Table 15 following, these results demonstrate that ODE-monoesters of Cidofovir (CDV) and PMEG lost 14.7% and 19.1% of body weight, respectively, which was highly statistically significant versus day zero (p=0.0007 and p<0.001). However, oral ODE-benzyl diesters of the CDV and PMEG nucleoside phosphonates exhibited no statistically significant effects ("ns") on body weight compared with the unmodified compounds.

TABLE 15

Effect of oral Octadecyloxyethyl-benzyl-(ODE-bn-) acyclic phosphonate diesters and Octadecyloxyethyl-monoesters of acyclic nucleoside phosphonates on body weight in Balb-c Mice

| Compound | Dose | Day 0 | Day 6 | p value, 0 vs 6 |
|---|---|---|---|---|
| ODE-CDV | 20 mg/kg/day | 19.88 ± 0.55 (6) | 16.96 ± 1.38 (6) | 0.0007 |
| ODE-bn-CDV (Cmpd 219) | 20 mg/kg/day | 19.03 ± 1.16 (6) | 19.27 ± 1.32 (6) | ns |
| ODE-PMEG | 4 mg/kg/day | 19.17 ± 0.581 (3) | 15.5 ± 0.514(3) | <0.001 |
| ODE-bn-PMEG (Cmpd 1) | 4 mg/kg/day | 18.63 ± 0.728 (3) | 18.42 ± 1.00 (3) | ns |

Example 28

Antiviral Effect of ANP Diesters in Cells Infected with Human Cytomegalovirus (AD169)

Method.

Primary low passage human foreskin fibroblast (HFF) cells in 96-well plates were infected at an MOI of 0.01 PFU/cell with the AD169 strain of human cytomegalovirus and incubated for 14 days. Media was then aspirated and cell monolayers were stained with crystal violet and rinsed with distilled water. Crystal violet associated with the cells was then quantified in a spectrophotometer and the concentration of the compound that was sufficient to reduce virus replication by 50% ($EC_{50}$) was calculated. Cytotoxicity was measured in parallel by similar methods to yield the concentration that reduced cell number by 50% ($CC_{50}$).

Results.

Results are tabulated in Table 16 following.

TABLE 16

Antiviral Effect of ANP diesters in cells infected with human cytomegalovirus (AD169)

| Compound # | $EC_{50}$, μM | $CC_{50}$, μM | Selectivity Index |
|---|---|---|---|
| 219 | <0.03 | 84.2 | >2807 |
| 218 | <0.03 | 7.49 | >250 |
| 231 | <0.03 | 19.0 | >633 |
| 230 | <0.03 | 3.72 | >124 |
| 1 | <0.03 | 51.5 | >1717 |
| 2 | 0.11 | 18.3 | 166 |

Example 29

Antiviral Effect of ANP Diesters in Cells Infected with Vaccinia Virus (Copenhagen)

Method:

Primary low passage human foreskin fibroblast (HFF) cells in 96-well plates were infected at an MOI of 0.01 PFU/cell with the Copenhagen strain of vaccinia virus and incubated for 7 days. Media was then aspirated and cell monolayers were stained with crystal violet and rinsed with distilled water. Crystal violet associated with the cells was then quantified in a spectrophotometer and the concentration of the compound that was sufficient to reduce virus replication by 50% ($EC_{50}$) was calculated. Cytotoxicity was measured in parallel by similar methods to yield the concentration that reduced cell number by 50% ($CC_{50}$).

Results.

Results are tabulated in Table 17 following.

TABLE 17

Antiviral Effect of ANP diesters in cells infected with vaccinia virus (Copenhagen)

| Compound # | $EC_{50}$, μM | $CC_{50}$, μM | Selectivity Index |
|---|---|---|---|
| 219 | 0.09 | >100 | >1110 |
| 218 | <0.03 | >100 | >3330 |
| 231 | 0.23 | >100 | >435 |
| 230 | 0.06 | 97.5 | 1625 |

Example 30

Antiviral Effect of ANP Diesters in Cells Infected BK Virus (Gardner Strain)

Method:

Primary low passage human foreskin fibroblast (HFF) cells in 96-well plates were infected at an MOI of 0.01 PFU/cell and incubated for 14 days. Media was then aspirated and total DNA was isolated and genome copy number was quantified by qPCR using the primers 5'-AGT GGA TGG GCA GCC TAT GTA-3' (SEQ ID NO:1), 5'-TCA TAT CTG GGT CCC CTG GA-3' (SEQ ID NO:2) and probe 5'-6-FAM AGG TAG AAG AGG TTA GGG TGT TTG ATG GCA CAG TAMRA-3'(SEQ ID NO:3). In a parallel experiment in uninfected cells cytotoxicity was determined by CELLTITER-GLO® find the concentration that reduced cell number by 50% ($CC_{50}$).

Results.

Results are tabulated in Table 18 following.

TABLE 18

Antiviral Effect of ANP diesters in cells infected BK virus (Gardner strain)

| Compound # | $EC_{50}$, μM | $CC_{50}$, μM | Selectivity Index |
|---|---|---|---|
| 219 | <0.03 | 6.54 | >218 |
| 218 | <0.03 | 2.80 | >93 |
| 231 | <0.03 | 13.29 | >443 |
| 230 | 0.06 | 19.61 | 327 |
| 1 | <0.03 | 3.06 | >102 |
| 2 | <0.03 | 7.14 | >238 |

Example 31

Antiviral Effect of ANP Diesters in HFF Cells Infected with HSV-1 (E-377)

Method.

Primary low passage human foreskin fibroblast (HFF) cells in 96-well plates were infected at an MOI of 0.01 PFU/cell with the E377 strain of herpes simplex virus type 1 and incubated for 3 days. Media was then aspirated and cell monolayers were stained with crystal violet and rinsed with distilled water. Crystal violet associated with the cells was then quantified in a spectrophotometer and the concentration of the compound that was sufficient to reduce virus replication by 50% ($EC_{50}$) was calculated. Cytotoxicity was measured in parallel by similar methods to yield the concentration that reduced cell number by 50% ($CC_{50}$).

Results.

Results are tabulated in Table 19 following.

TABLE 19

Antiviral Effect of ANP diesters in HFF cells infected with HSV-1 (E-377)

| Compound # | $EC_{50}$, µM | $CC_{50}$, µM | Selectivity Index |
|---|---|---|---|
| 219 | 1.25 | 19.3 | 15.4 |
| 218 | 0.92 | 14.5 | 15.8 |
| 231 | 1.40 | 88.3 | 63 |
| 230 | 2.77 | 82.2 | 30 |
| 1 | 1.08 | >100 | >93 |
| 2 | >4.0 | 16.6 | <4.2 |

Example 32

Antiviral Effect of ANP Diesters in HPV-11 Infected HEK 293 Cells

Method.

An origin-containing plasmid was co-transfected with HPV-11 E1 and E2 protein expression vectors into HEK 293 cells. At 4 hr post-transfection, cells were treated with compound dilutions and the cells were incubated for 48 hr. Replication of the virus origin was detected with DpnI and exonuclease III to remove unreplicated input bacterial plasmid DNA. Remaining replicated DNA was quantified by qPCR. Toxicity was determined by trypan blue exclusion.

Results.

Results are tabulated in Table 20 following.

TABLE 20

Antiviral effect of ANP diesters in HPV-11 infected HEK 293 cells

| Compound # | $EC_{50}$, µM | $CC_{50}$, µM | Selectivity Index |
|---|---|---|---|
| 1 | 0.49 | >100 | >204 |
| 1a | [1.06, $EC_{90}$] | — | — |
| 1b | [1.16, $EC_{90}$] | — | — |
| 218 | 0.77 | >100 | >370 |
| 2 | 0.27 | >100 | >130 |
| 219 | 2.04 | >10 | >4.9 |
| 230 | 0.56 | >10 | >17.9 |
| 231 | 1.56 | >10 | >6.41 |

** $EC_{90}$ is the concentration required to reduce viral replication by 90%.

Example 33

Antiviral Effect of ANP Diesters in HPV-16 Infected HEK 293 Cells

Method.

An origin-containing plasmid was co-transfected with HPV-16 E1 and E2 protein expression vectors into HEK 293 cells. At 4 hr post-transfection, cells were treated with compound dilutions and the cells were incubated for 48 hr. Replication of the virus origin was detected with DpnI and exonuclease III to remove unreplicated input bacterial plasmid DNA. Remaining replicated DNA was quantified by qPCR. Toxicity was determined by trypan blue exclusion.

Results.

Results are tabulated in Table 21 following.

TABLE 21

Antiviral effect of ANP diesters in HPV-16 infected HEK 293 cells.

| Compound # | $EC_{50}$, µM | $CC_{50}$, µM | Selectivity Index |
|---|---|---|---|
| 218 | 0.24 | >10 | >41.7 |
| 219 | 2.23 | >10 | >4.48 |
| 1 | 0.20 | >10 | >50 |
| 19 | 5.27 | >10 | >1.9 |
| 2 | 0.99 | >10 | >10.1 |

Example 34

Antiviral Effect of ANP Diesters in HPV-18 Infected Primary Human Keratinocyte Rafts Method.

Primary human keratinocytes (PHKs) were transfected with an HPV-18 genomic plasmid containing G418 resistance gene which was generated by Cre-loxP-mediated excision recombination. After a 4 day selection with G418, the surviving cells were cultured for 2-3 day and used to develop into raft cultures where the PHK cells stratify and differentiate into a squamous epithelium in 10 or more days. HPV-18 viral DNA usually amplifies between 10-14 days after the raft cultures are lifted to the air-medium interface. Efficacy and toxicity of the test compounds were determined at three concentrations added to the media from day 6 or 8 until day 14. Medium is changed every other day. Prior to harvest, BrdU is added to the medium at 100 µg/ml to document host cell DNA replication. One set of raft cultures (with or without test compounds) is harvested for quantitative real time PCR (qPCR) to determine the copy number of HPV-18 DNA/cell. Another set of the raft cultures are fixed in formalin, embedded in paraffin and toxicity is determined by histology. Additional sections are subjected to in situ hybridization to localize viral DNA amplification and BrdU incorporation which denotes host DNA replication in basal and suprabasal strata.

Results.

Results are tabulated in Table 22 following.

TABLE 22

Antiviral effect of ANP diesters in HPV-18 infected primary human keratinocyte rafts

| Compound # | $EC_{50}$, μM | $CC_{50}$, μM | Selectivity Index |
|---|---|---|---|
| 218 | 0.25 | >10 | >39 |
| 219 | 1.06 | >10 | >9.4 |
| 1 | 0.21 | 10 | 48 |

Example 35

Antiviral Effect of ANP Diesters in JC Virus (MAD-1) Infected COS7 Cells

Method.

COS7 cells in 96-well plates were infected at an MOI of 0.01 PFU/cell with the MAD-1 strain of JC virus and incubated for 7 days. Media was then aspirated and total DNA was isolated and genome copy number was quantified by qPCR using primers 5'-CTG GTC ATG TGG ATG CTG TCA-3' (SEQ ID NO:4) and 5'-GCC AGC AGG CTG TTG ATA CTG-3' (SEQ ID NO:5) and probe 5'-6-FAM-CCC TTT GTT TGG CTG CT-TAMRA-3 (SEQ ID NO:6) together with the plasmid pMP508 to provide a standard curve for quantitation. In a parallel experiment in uninfected cells, cytotoxicity was determined by CELLTITER-GLO® to find the concentration that reduced cell number by 50% ($CC_{50}$).

Results.

Results are tabulated in Table 23 following.

TABLE 23

Antiviral effect of ANP diesters in JC virus (MAD-1) infected COS7 cells

| Compound # | $EC_{50}$, μM | $CC_{50}$, μM | Selectivity Index |
|---|---|---|---|
| 1 | 0.07 | 63.8 | 911 |
| 2 | >4 | 10.6 | <2.7 |
| 218 | >4 | 10.2 | <2.6 |
| 219 | >4 | 12.8 | <3.2 |
| 230 | >4 | 18.4 | <4.6 |
| 231 | >20 | 62.6 | <3 |

Example 36

Antiviral Effect of ANP Diesters in HIV-1$_{92US727}$ Infected Human Peripheral Blood Monocytes Method.

Human peripheral blood monocyte (PBMC) based anti-HIV assays were performed as previously described (K. M. Watson, et al., 2008, *Antimicrob Agents Chemother.* 52:2787). Briefly, PHA-stimulated PBMCs cultured in the presence of IL-2 were suspended at $1 \times 10^6$ cells/mL and were added to a 96-well round-bottom plate. Serially diluted test materials were added to the plate in triplicate followed by the appropriate pre-titered strain of HIV. The culture was incubated for 7 days at 37° C./5% $CO_2$. Following the incubation, supernatants were collected for analysis of virus replication by supernatant reverse transcriptase activity and cells analyzed for viability by tetrazolium dye XTT reduction (2,3-bis(2-methoxy-4-nitro-5-sulfophenyl)-5-[(phenylamino)carbonyl]-2H-tetrazolium hydroxide). All the assays were carried out in triplicate. Microsoft Excel 2007 was used to analyze and graph data. The percent reduction in virus replication compared to the untreated virus controls was calculated for each compound. The percent cell control value was calculated for each compound comparing the drug treated uninfected cells to the uninfected cells in medium alone.

Results.

Results are tabulated in Table 24 following.

TABLE 24

Antiviral effect of ANP diesters in HIV-1$_{92US727}$ infected human peripheral blood monocytes

| Compound # | $EC_{50}$, μM | $CC_{50}$, μM | Selectivity Index |
|---|---|---|---|
| 218 | <0.010 | 0.23 | >23.0 |
| 230 | <0.10 | 0.55 | >5.5 |
| 219 | <0.10 | 2.87 | >28.7 |
| 231 | <0.30 | 19.0 | >63.3 |
| 2 | <0.010 | 11.0 | >1100 |
| 1 | <0.010 | 0.04 | >4.0 |
| 19 | <0.003 | 0.018 | >9.0 |
| 25 | <0.002 | 0.25 | >125 |
| 164 | <0.40 | 15.0 | >37.5 |
| 146 | <0.04 | 12.5 | >312 |
| 74 | <0.005 | 24.6 | >4920 |
| 92 | <0.005 | 24.1 | >4820 |
| 73 | <0.005 | 11.3 | >2260 |

Example 37

Antiviral Effect of ANP Diesters on Hepatitis B Virus Replication in 2.2.15 Cells In Vitro Method.

HBV antiviral assays (Korba & Gerin, *Antivir. Res.*, 1992, 19:55 and Iyer, et al., *Antivir Agents Chem Chemother.*, 2004, 48:2199) are conducted using confluent cultures of 2.2.15 cells (genotype ayw; parental cell HepG2) maintained on 96-well flat-bottomed tissue culture plates. Confluence in this culture system is required for active, high levels of HBV replication equivalent to that observed in chronically-infected individuals (Sells, et al., *J. Virol.*, 1988, 62:2836; Korba & Gerin, *Antivir. Res.*, 1992, 19:55). Cultures are treated for 7 days. HBV DNA levels in the culture medium (representing HBV virion production) are assessed by quantitative blot hybridization 24 hrs. after the last treatment. Cytotoxicity is assessed ($A_{510}$) by uptake of neutral red dye 24 hr. following the last treatment. Lamivudine (LMV) is used as the standard assay control. $EC_{50}$, $EC_{90}$ and $CC_{50}$ values are calculated by linear regression analysis (MS EXCEL®, QUATTROPRO®) using data combined from all treated cultures (Korba & Gerin, 1992, Id.; Okuse, et al., *Antivir. Res.*, 2005, 65:23). Standard deviations for $EC_{50}$ and $EC_{90}$ values are calculated from the standard errors generated by the regression analyses. $EC_{50}$ and $EC_{90}$ are drug concentrations at which a 2-fold, or a 10-fold depression of HBV DNA (relative to the average levels in untreated cultures), respectively, is observed. $CC_{50}$ is the drug concentration at which a 2-fold lower level of neutral red dye uptake (relative to the average levels in untreated cultures) is observed.

Results.

Results are tabulated in Table 25 following.

TABLE 25

Antiviral effect of ANP diesters on hepatitis B virus replication in 2.2.15 cells in vitro.

| Compound # | $EC_{50}$, μM | $CC_{50}$, μM | Selectivity Index |
|---|---|---|---|
| 2 | 0.88 | >100 | >113 |
| 218 | 0.76 | >100 | >132 |
| 219 | 0.45 | >100 | >223 |
| 19 | 43.0 | >100 | >2.33 |
| 1 | 0.44 | >100 | >226 |
| 146 | 33.0 | >100 | >3.03 |
| 164 | 0.46 | >100 | >216 |
| 74 | 6.5 | 64 | 10 |
| 92 | 7.3 | 68 | 9.3 |
| 73 | 34 | 63 | 1.9 |

VII. Embodiments

A first set of embodiments P1-P7 follows.

Embodiment P1

A compound with structure of Formula (I):

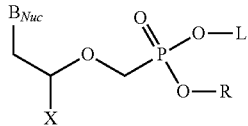

(I)

or stereoisomer, salt, hydrate, solvate, or crystalline form thereof, wherein $B_{Nuc}$ is a naturally occurring purine or pyrimidine base, or analog thereof; L is a lipophilic promoiety, substituted or unsubstituted alkyl, substituted or unsubstituted heteroalkyl, or O-substituted glyceryl having the formula —$CH_2CH(OR^1)$—$CH_2(OR^2)$ (II), wherein $R^1$ and $R^2$ are independently substituted or unsubstituted alkyl, or substituted or unsubstituted aryl; R is substituted or unsubstituted lower alkyl, substituted or unsubstituted lower heteroalkyl, substituted or unsubstituted lower cycloalkyl, substituted or unsubstituted lower heterocycloalkyl, substituted or unsubstituted aryl, or substituted or unsubstituted lower heteroaryl; and X is hydrogen, substituted or unsubstituted lower alkyl, or substituted or unsubstituted lower heteroalkyl.

Embodiment P2

A method of treating a viral disease in a subject, comprising administering to a subject in need thereof a therapeutically effective amount of a compound of embodiment P1.

Embodiment P3

A method for treating cancer in a subject, comprising administering to a subject in need thereof a therapeutically effective amount of a compound of embodiment P1.

Embodiment P4

A method of killing or inhibiting the growth of a transformed cell, comprising contacting a transformed cell with a therapeutically effective amount of a compound of embodiment P1.

Embodiment P5

A method for treating a proliferative disorder in a subject, comprising administering to a subject in need thereof a therapeutically effective amount of a compound of embodiment P1.

Embodiment P6

A pharmaceutical composition comprising a compound according to embodiment P1, and pharmaceutically acceptable excipient.

Embodiment P7

A method for synthesis of a compound with structure of Formula (I) according to Scheme 2:

Scheme 2

1. $B_{Nuc}$-CH(X)-CH$_2$-OH + Y-CH$_2$-P(=O)(O$^-$Na$^+$)(O-R) →(strong base)
   2-1       2-2

$B_{Nuc}$-CH$_2$-CH(X)-O-CH$_2$-P(=O)(OH)(O-R)

2-3

2. $B_{Nuc}$-CH$_2$-CH(X)-O-CH$_2$-P(=O)(OH)(O-R) →(L-OH, Coupling agent)

2-3

$B_{Nuc}$-CH$_2$-CH(X)-O-CH$_2$-P(=O)(O-L)(O-R);

(I)

wherein $B_{Nuc}$ is a naturally occurring purine or pyrimidine base, or analog thereof; L is a lipophilic promoiety, substituted or unsubstituted alkyl, substituted or unsubstituted heteroalkyl, or O-substituted glyceryl having the formula —$CH_2CH(OR^1)$—$CH_2(OR^2)$ (II), wherein $R^1$ and $R^2$ are independently substituted or unsubstituted alkyl, or substituted or unsubstituted aryl; R is substituted or unsubstituted lower alkyl, substituted or unsubstituted lower heteroalkyl, substituted or unsubstituted lower cycloalkyl, substituted or unsubstituted lower heterocycloalkyl, substituted or unsubstituted aryl, or substituted or unsubstituted lower heteroaryl; and X is hydrogen, substituted or unsubstituted lower alkyl, or substituted or unsubstituted lower heteroalkyl; and Y is a leaving group; the method including: 1) contacting a protected nucleoside $B_{Nuc}$ with structure of Formula (2-1) with an ester with structure of Formula (2-2) in the presence of a strong base under conditions suitable to afford a monoester with structure of Formula (2-3); and 2) reacting said monoester with structure of Formula (2-3) with L-OH in the presence of a coupling agent, thereby synthesizing a compound with structure of Formula (I).

Further embodiments include the following.

Embodiment 1

A compound of Formula (Ia), or a pharmaceutically acceptable salt, hydrate, solvate or crystalline form thereof

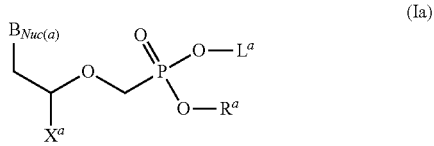

(Ia)

wherein: $B_{Nuc(a)}$ is a naturally occurring purine, a naturally occurring pyrimidine, a non-naturally occurring purine or a non-naturally occurring pyrimidine; $L^a$ is an unsubstituted $C_{12-24}$ alkyl, an unsubstituted $C_{13-29}$ heteroalkyl or a substituted glyceryl moiety, wherein the glyceryl moiety is substituted with one or more groups selected from an unsubstituted $C_{13-29}$ alkyl, an unsubstituted $C_{13-29}$ heteroalkyl, a substituted or unsubstituted aryl ($C_{1-6}$ alkyl), a substituted or unsubstituted heteroaryl($C_{1-6}$ alkyl) and a substituted or unsubstituted heterocycloalkyl($C_{1-6}$ alkyl); $R^a$ is selected from the group consisting of an unsubstituted $C_{1-6}$ alkyl, a substituted or unsubstituted aryl, a substituted or unsubstituted heteroaryl, a substituted or unsubstituted heterocycloalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); and $X^a$ is hydrogen, an unsubstituted $C_{1-6}$ alkyl, a halogen substituted $C_{1-6}$ alkyl, a hydroxy substituted $C_{1-6}$ alkyl or an unsubstituted $C_{1-6}$ alkoxy.

Embodiment 2

The compound of embodiment 1 wherein $X^a$ is hydrogen.

Embodiment 3

The compound of embodiment 1 wherein $X^a$ is methyl.

Embodiment 4

The compound of embodiment 1, wherein $X^a$ is methoxy.

Embodiment 5

The compound of embodiment 1, wherein $X^a$ is a fluoro substituted $C_{1-6}$ alkyl.

Embodiment 6

The compound of embodiment 5, wherein $X^a$ is a $CH_2F$.

Embodiment 7

The compound of embodiment 1, wherein $X^a$ is a $CH_2OH$.

Embodiment 8

The compound of any one of embodiments 1-7, wherein $L^a$ is an unsubstituted $C_{13-29}$ heteroalkyl.

Embodiment 9

The compound of embodiment 8, wherein $L^a$ has the structure —$(CH_2)_{1-6}$—O—$(CH_2)_{11-21}$—$CH_3$.

Embodiment 10

The compound of embodiment 9, wherein $L^a$ has the structure —$(CH_2)_2$—O—$(CH_2)_{17}$—$CH_3$.

Embodiment 11

The compound of embodiment 9, wherein $L^a$ has the structure —$(CH_2)_3$—O—$(CH_2)_{15}$—$CH_3$.

Embodiment 12

The compound of embodiment 8, wherein $L^a$ has the structure —$(CH_2)_{1-6}$—O—$(CH_2)_{10-20}$—$(CHCH_3)$—$CH_3$.

Embodiment 13

The compound of any one of embodiments 1-7, wherein $L^a$ is a substituted glyceryl moiety.

Embodiment 14

The compound of embodiment 13, wherein $L^a$ has the structure —$(CH_2)$—$CH(OR^{a1})$—$(CH_2)$—$O(CH_2)_{11-21}$—$CH_3$, wherein $R^{a1}$ is a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl).

Embodiment 15

The compound of embodiment 14, wherein $L^a$ has the structure

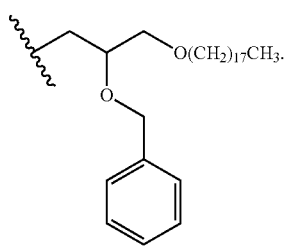

Embodiment 16

The compound of embodiment 1, wherein $R^a$ is a substituted or unsubstituted aryl.

Embodiment 17

The compound of embodiment 16, wherein the substituted or unsubstituted aryl is a substituted or unsubstituted phenyl.

Embodiment 18

The compound of embodiment 16, wherein the substituted or unsubstituted aryl is a substituted or unsubstituted naphthyl.

Embodiment 19

The compound of embodiment 1, wherein $R^a$ is a substituted or unsubstituted aryl($C_{1-6}$ alkyl).

Embodiment 20

The compound of embodiment 19, wherein the substituted or unsubstituted aryl($C_{1-6}$ alkyl) is a substituted or unsubstituted benzyl.

Embodiment 21

The compound of embodiment 1, wherein $R^a$ is a substituted or unsubstituted heterocycloalkyl($C_{1-6}$ alkyl).

Embodiment 22

The compound of embodiment 21, wherein the substituted or unsubstituted heterocycloalkyl($C_{1-6}$ alkyl) is a substituted or unsubstituted galactosyl.

Embodiment 23

The compound of embodiment 1, wherein $B_{Nuc(a)}$ is a naturally occurring purine.

Embodiment 24

The compound of embodiment 1, wherein $B_{Nuc(a)}$ is a naturally occurring pyrimidine.

Embodiment 25

The compound of embodiment 1, wherein $B_{Nuc(a)}$ is a non-naturally occurring purine.

Embodiment 26

The compound of embodiment 1, wherein $B_{Nuc(a)}$ is a non-naturally occurring pyrimidine.

Embodiment 27

The compound of embodiment 1, wherein $B_{Nuc(a)}$ is selected from the group consisting of:

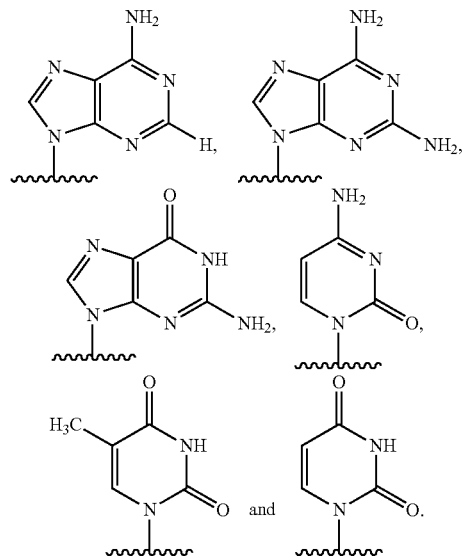

Embodiment 28

The compound of embodiment 1, wherein the compound has the structure:

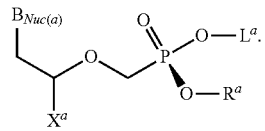

Embodiment 29

The compound of embodiment 1, wherein the compound has the structure:

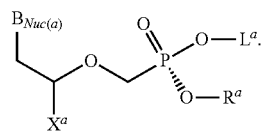

Embodiment 30

The compound of embodiment 1, wherein the compound has the structure:

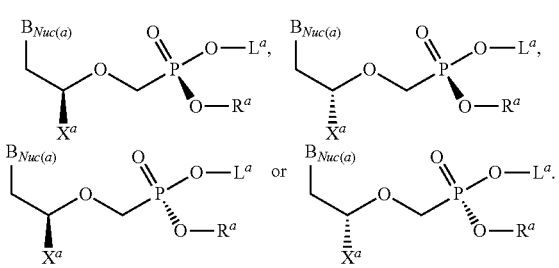

Embodiment 31
The compound of embodiment 1, wherein the compound is selected from any one of the compounds in Tables 1-10, or a pharmaceutically acceptable salt, hydrate, solvate or crystalline form thereof.
Embodiment 32
The compound of embodiment 1, wherein the compound is selected from the group consisting of:
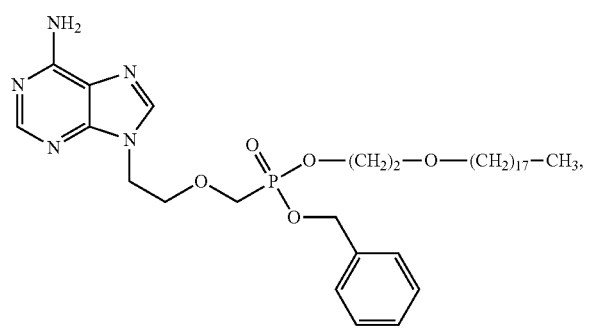
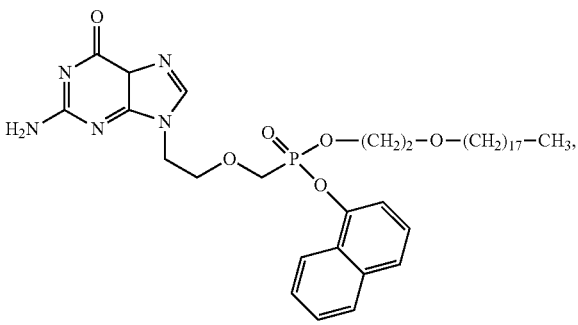
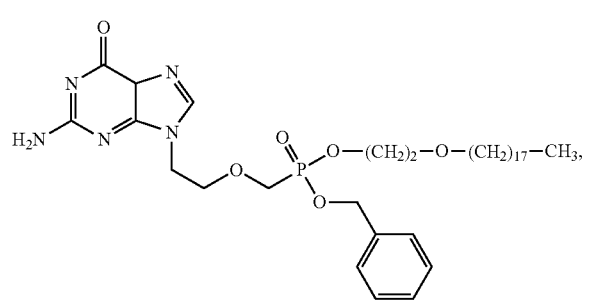
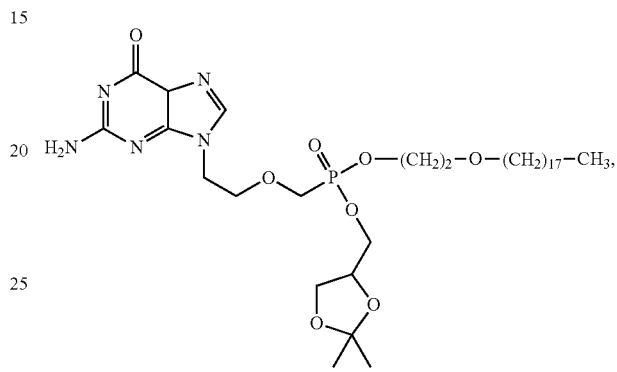
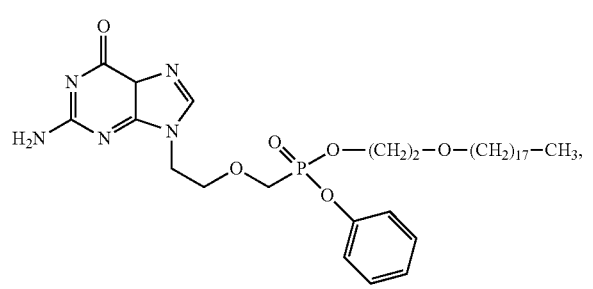
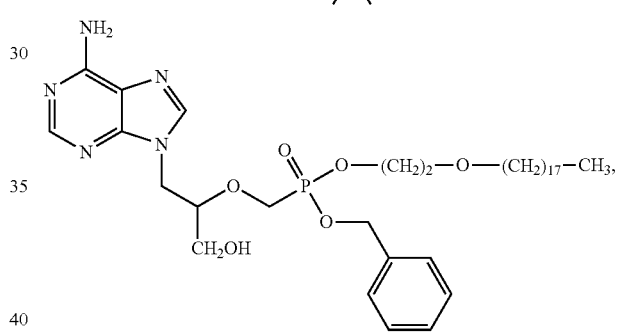
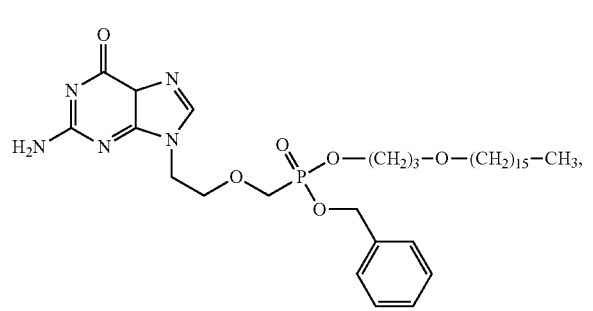
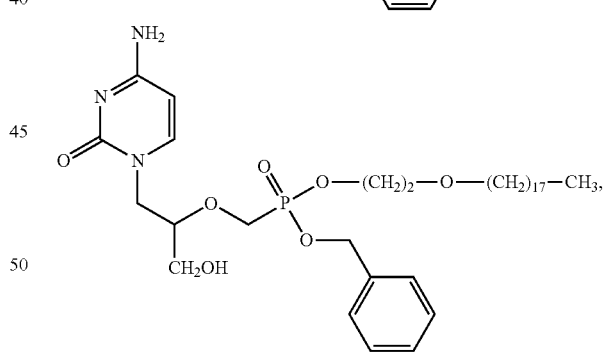
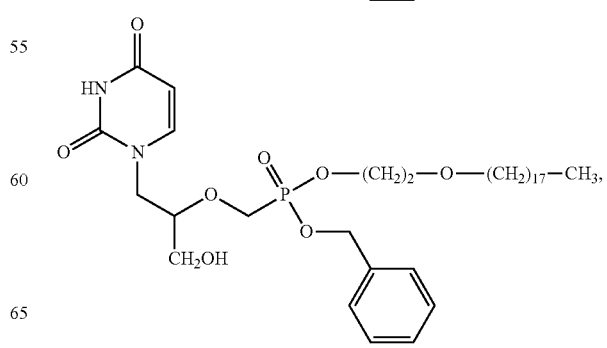

127
-continued
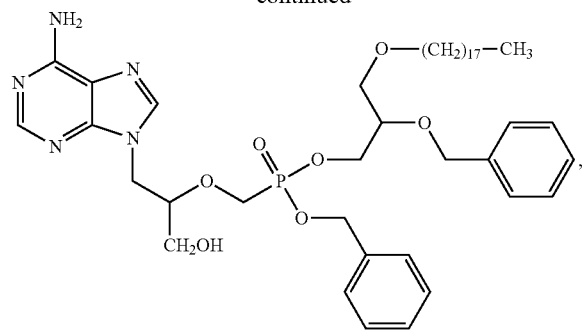
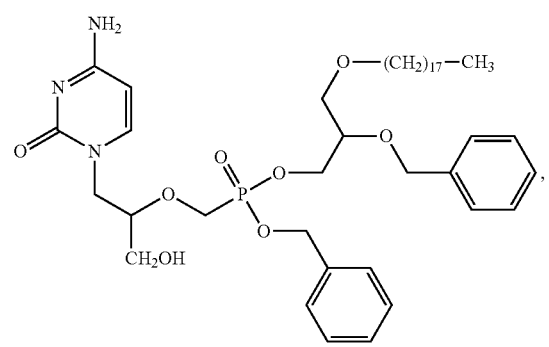
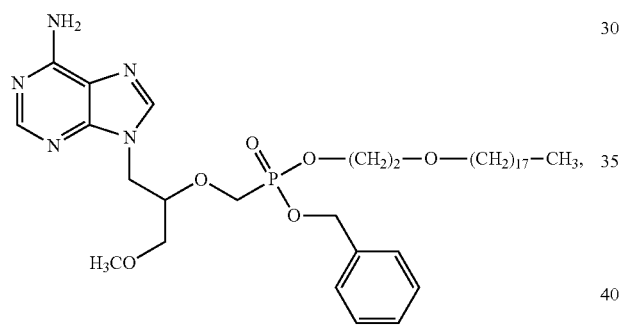
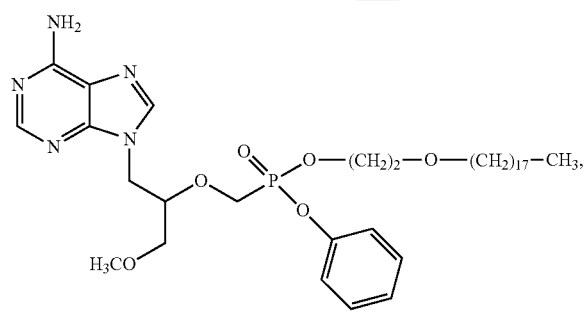
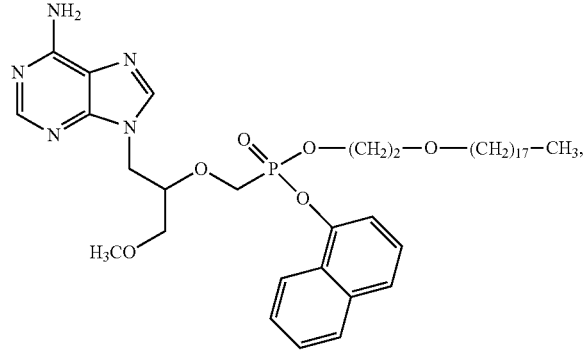
128
-continued
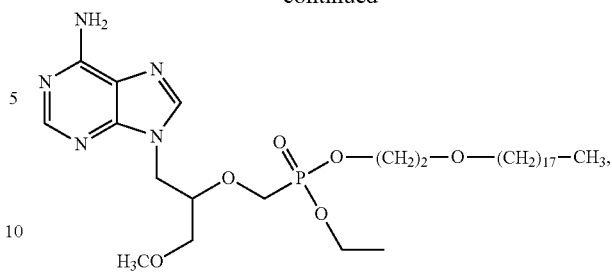
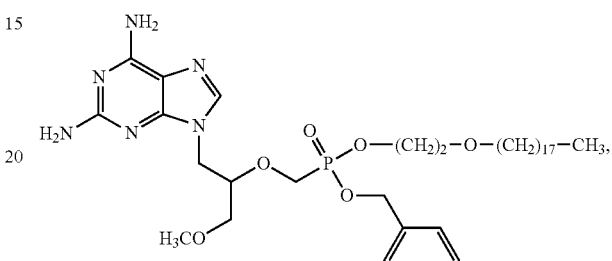
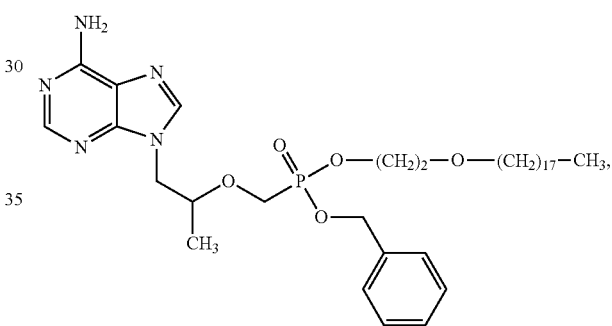
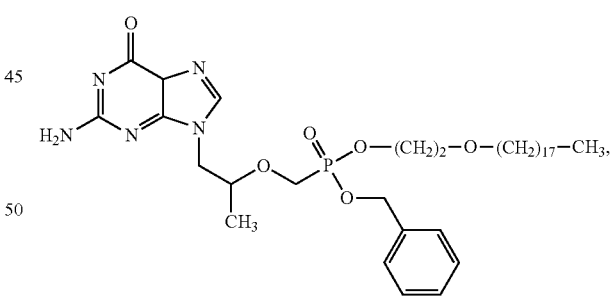
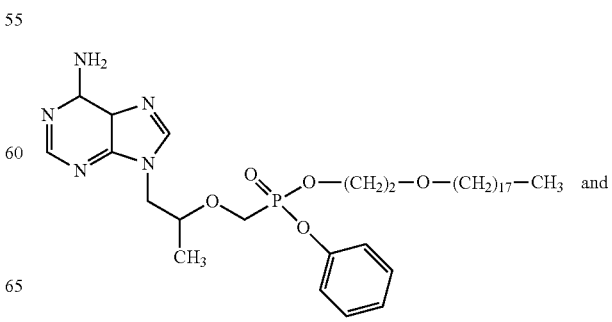

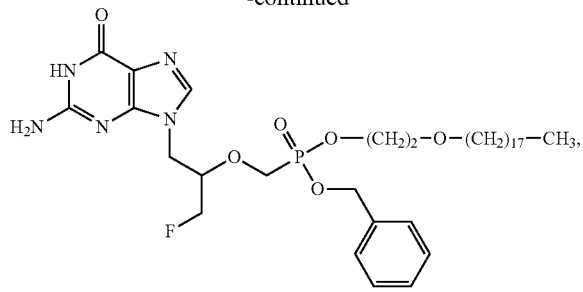

or a pharmaceutically acceptable salt, hydrate, solvate or crystalline form of any of the foregoing.

Embodiment 33

A pharmaceutical composition including an effective amount of a compound of any one of embodiments 1-32, or a pharmaceutically acceptable salt, hydrate, solvate or crystalline form thereof, and a pharmaceutically acceptable excipient.

Embodiment 34

The pharmaceutical composition of embodiment 33, wherein the pharmaceutical composition is in the form of a cream, a gel or an ointment.

Embodiment 35

The pharmaceutical composition of embodiment 33 or 34, wherein the pharmaceutical composition is a topical formulation.

Embodiment 36

Use of a compound of any one of embodiments 1-32, or a pharmaceutically acceptable salt, hydrate, solvate or crystalline form thereof, in the preparation of a medicament for treating a viral disease in a subject, wherein the viral disease is selected from the group consisting of human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

Embodiment 37

The use of embodiment 36, wherein said virus is human papilloma virus.

Embodiment 38

The use of embodiment 37, said compound, or a pharmaceutically acceptable salt, hydrate, solvate or crystalline form thereof, for use in treating a plurality of types of human papilloma virus.

Embodiment 39

The use of embodiment 37, wherein the human papilloma virus is selected from the group consisting human papilloma virus type 11, type 16 and type 18.

Embodiment 40

Use of a compound of any one of embodiments 1-32, or a pharmaceutically acceptable salt, hydrate, solvate or crystalline form thereof, in the preparation of a medicament for treating cancer of the cervix in a subject.

Embodiment 41

Use of a compound of any one of embodiments 1-32, or a pharmaceutically acceptable salt, hydrate, solvate or crystalline form thereof, in the preparation of a medicament for inhibiting growth of a cell transformed by a virus, wherein the virus is selected from the group consisting of human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

Embodiment 42

A compound of any one of embodiments 1-32, or a pharmaceutically acceptable salt, hydrate, solvate or crystalline form thereof, for use in treating a viral disease in a subject, wherein the viral disease is selected from the group consisting of human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

Embodiment 43

The compound of embodiment 42, wherein said virus is human papilloma virus.

Embodiment 44

The compound of embodiment 43, or a pharmaceutically acceptable salt, hydrate, solvate or crystalline form thereof, for use in treating a plurality of types of human papilloma virus.

Embodiment 45

The compound of embodiment 43, wherein the human papilloma virus is selected from the group consisting human papilloma virus type 11, type 16 and type 18.

Embodiment 46

A compound of any one of embodiments 1-32, or a pharmaceutically acceptable salt, hydrate, solvate or crystalline form thereof, for use in treating cancer of the cervix in a subject.

Embodiment 47

A compound of any one of embodiments 1-32, or a pharmaceutically acceptable salt, hydrate, solvate or crystalline form thereof, for use in inhibiting growth of a cell transformed by a virus, wherein the virus is selected from the group consisting of human papilloma virus, HIV, hepatitis B virus, hepatitis C virus, variola virus, vaccinia virus, an adenovirus, a cytomegalovirus, herpes simplex virus 1, herpes simplex virus 2, Epstein Barr virus, BK virus, JC virus, feline leukemia virus and feline immunodeficiency virus.

Embodiment 48

A method for synthesis of the compound of Formula (Ia) according to Embodiment 1:

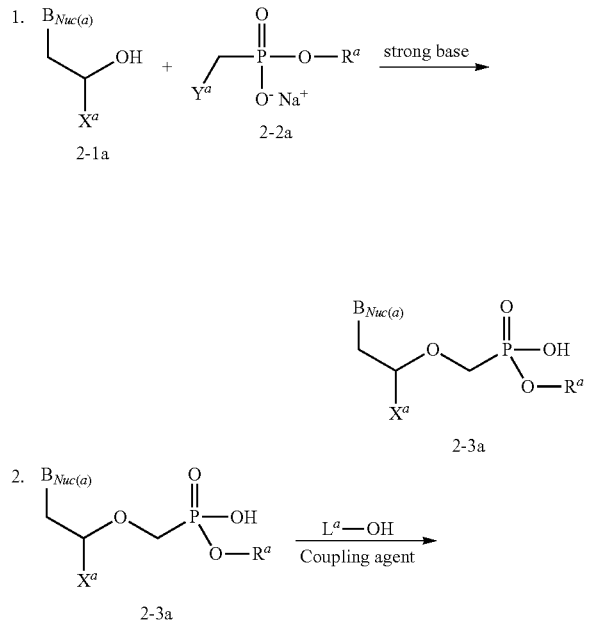

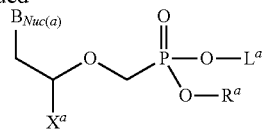

(Ia)

wherein: $B_{Nuc(a)}$ is a naturally occurring purine, a naturally occurring pyrimidine, a non-naturally occurring purine or a non-naturally occurring pyrimidine; $L^a$ is an unsubstituted $C_{12-24}$ alkyl, an unsubstituted $C_{13-29}$ heteroalkyl or a substituted glyceryl moiety, wherein the glyceryl moiety is substituted with one or more groups selected from an unsubstituted $C_{13-29}$ alkyl, an unsubstituted $C_{13-29}$ heteroalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); le is selected from the group consisting of an unsubstituted $C_{1-6}$ alkyl, a substituted or unsubstituted aryl, a substituted or unsubstituted heteroaryl, a substituted or unsubstituted heterocycloalkyl, a substituted or unsubstituted aryl($C_{1-6}$ alkyl), a substituted or unsubstituted heteroaryl($C_{1-6}$ alkyl) and a substituted or unsubstituted heterocycloalkyl($C_{1-6}$ alkyl); $X^a$ is hydrogen, an unsubstituted $C_{1-6}$ alkyl, a halogen substituted $C_{1-6}$ alkyl, a hydroxy substituted $C_{1-6}$ alkyl or an unsubstituted $C_{1-6}$ alkoxy; and $Y^a$ is a leaving group; the method including: contacting a compound of Formula (2-1a) that has a protected $B_{Nuc(a)}$ with a compound of Formula (2-2a) in the presence of a strong base to form a compound of Formula (2-3a); and reacting the compound of Formula (2-3a) with $L^a$-OH in the presence of a coupling agent to form the compound of Formula (Ia).

What is claimed is:

1. A process for preparing a compound of Formula I comprising combining an alcohol R—OH, a coupling agent, a base, an organic solvent, and a compound of formula:

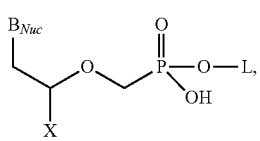

wherein
$B_{Nuc}$ is a naturally occurring purine or pyrimidine base;
X is hydrogen, $C_{1-6}$ alkyl, or $C_{1-6}$ heteroalkyl; and
L is a $C_{13-29}$ heteroalkyl or O-substituted glyceryl having the formula —$CH_2CH(OR^1)$—$CH_2(OR^2)$ (II), wherein $R^1$ and $R^2$ are independently alkyl or aryl;

thereby obtaining a compound of Formula I:

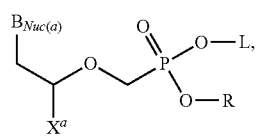

wherein
R is aryl, benzyl, heteroaryl, aryl($C_{1-6}$ alkyl), or heteroaryl($C_{1-6}$ alkyl).

2. The process of claim 1, further comprising resolving the compound of Formula I to an optically active enantiomer or diastereomer of Formula I.

3. The process of claim 1, wherein R—OH is benzyl alcohol.

4. The process of claim 1, wherein the coupling agent is (benzotriazol-1-yloxy)-tripyrrolidinophosphonium hexafluorophosphate.

5. The process of claim 1, wherein the base is N,N-diisopropylethylamine.

6. The process of claim 1, wherein the organic solvent is N,N-dimethylformamide.

7. A process for preparing a compound of Formula Ia comprising combining an alcohol $R^a$—OH, a coupling agent, a base, an organic solvent, and a compound of formula:

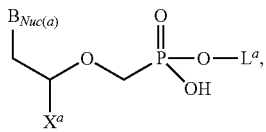

wherein
- $B_{Nuc(a)}$ is a naturally occurring purine, a naturally occurring pyrimidine, a non-naturally occurring purine or a non-naturally occurring pyrimidine;
- $X^a$ is hydrogen, $C_{1-6}$ alkyl, a halogen substituted $C_{1-6}$ alkyl, a hydroxy substituted $C_{1-6}$ alkyl, or $C_{1-6}$ alkoxy; and
- $L^a$ is $C_{12-24}$ alkyl, $C_{13-29}$ heteroalkyl, or a substituted glyceryl moiety, wherein the glyceryl moiety may be substituted with one or more groups selected from $C_{13-29}$ alkyl, $C_{13-29}$ heteroalkyl, aryl($C_{1-6}$ alkyl), heteroaryl($C_{1-6}$ alkyl) and heterocycloalkyl($C_{1-6}$ alkyl);

thereby obtaining a compound of Formula Ia:

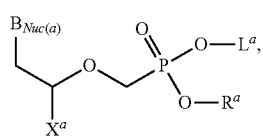

wherein
- $R^a$ is aryl, heteroaryl, aryl($C_{1-6}$ alkyl), or heteroaryl ($C_1$-6 alkyl).

8. The process of claim 7, further comprising resolving the compound of Formula Ia to obtain an optically active enantiomer or diastereomer of Formula Ia.

9. The process of claim 7, wherein $R^a$—OH is benzyl alcohol.

10. The process of claim 7, wherein the coupling agent is (benzotriazol-1-yloxy)-tripyrrolidinophosphonium hexafluorophosphate.

11. The process of claim 7, wherein the base is N,N-diisopropylethylamine.

12. The process of claim 7, wherein the organic solvent is N,N-dimethylformamide.

13. A process for preparing a compound of Formula I comprising combining an alcohol L-OH, a coupling agent, a base, an organic solvent, and a compound of Formula 2-3

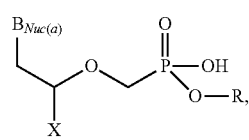

wherein
- $B_{Nuc}$ is a naturally occurring purine or pyrimidine base;
- X is hydrogen, $C_{1-6}$ alkyl, or $C_{1-6}$ heteroalkyl; and
- R is aryl, benzyl, heteroaryl, aryl($C_{1-6}$ alkyl), or heteroaryl($C_{1-6}$ alkyl);

thereby obtaining a compound of Formula I:

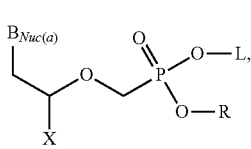

wherein
- L is $C_{13-29}$ heteroalkyl or O-substituted glyceryl having the formula —$CH_2CH(OR^1)$—$CH_2(OR^2)$, wherein $R^1$ and $R^2$ are independently alkyl or aryl.

14. The process of claim 13, further comprising resolving the compound of Formula I to obtain an optically active enantiomer or diastereomer of Formula I.

15. The process of claim 13, wherein L-OH is 2-(octadecyloxy)ethan-1-ol.

16. The process of claim 13, wherein the coupling agent is (benzotriazol-1-yloxy)-tripyrrolidinophosphonium hexafluorophosphate.

17. The process of claim 13, wherein the base is N,N-diisopropylethylamine.

18. The process of claim 13, wherein the organic solvent is N,N-dimethylformamide.

19. A process for preparing a compound of Formula Ia comprising combining an alcohol $L^a$-OH, a coupling agent, a base, an organic solvent, and a compound of Formula 2-3a:

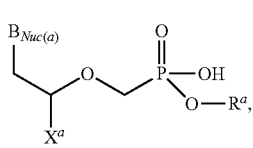

wherein
- $B_{Nuc}(a)$ is a naturally occurring purine, a naturally occurring pyrimidine, a non-naturally occurring purine or a non-naturally occurring pyrimidine;
- $X^a$ is hydrogen, $C_{1-6}$ alkyl, a halogen substituted $C_{1-6}$ alkyl, a hydroxy substituted $C_{1-6}$ alkyl, or $C_{1-6}$ alkoxy; and
- $R^a$ is aryl, heteroaryl, aryl($C_{1-6}$ alkyl), or heteroaryl ($C_{1-6}$ alkyl);

thereby obtaining a compound of Formula Ia:

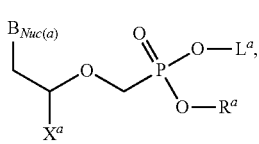

wherein
- $L^a$ is $C_{12-24}$ alkyl, $C_{13-29}$ heteroalkyl or a substituted glyceryl moiety, wherein the glyceryl moiety may be substituted with one or more groups selected from $C_{13-29}$ alkyl, $C_{13-29}$ heteroalkyl, aryl($C_{1-6}$ alkyl), heteroaryl($C_{1-6}$ alkyl), or heterocycloalkyl($C_{1-6}$ alkyl).

20. The process of claim 19, further comprising resolving the compound of Formula Ia to obtain an optically active enantiomer or diastereomer of Formula Ia.

21. The process of claim 19, wherein $L^a$-OH is 2-(octadecyloxy)ethan-1-ol.

22. The process of claim 19, wherein the coupling agent is (benzotriazol-1-yloxy)-tripyrrolidinophosphonium hexafluorophosphate.

23. The process of claim 19, wherein the base is N,N-diisopropylethylamine.

24. The process of claim 19, wherein the organic solvent is N,N-dimethylformamide.

25. A process for preparing a compound of Formula I comprising combining a strong base, an organic solvent, a compound of Formula 3-1:

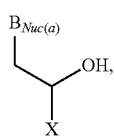

(3-1)

and a compound Formula 3-2:

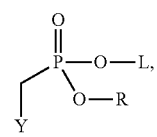

(3-2)

wherein
Y is a leaving group;
$B_{Nuc}$ is a naturally occurring or modified purine or pyrimidine base;
X is hydrogen, $C_{1-6}$ alkyl, or $C_{1-6}$ heteroalkyl;
L is $C_{13-29}$ heteroalkyl or O-substituted glyceryl having the formula $—CH_2CH(OR^1)—CH_2(OR^2)$, wherein $R^1$ and $R^2$ are independently alkyl or aryl; and
R is aryl, heteroaryl, benzyl, aryl($C_{1-6}$ alkyl), or heteroaryl($C_{1-6}$ alkyl);
thereby obtaining a compound of Formula I:

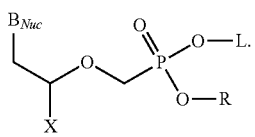

(I)

26. The process of claim 25, further comprising resolving the compound of Formula I to obtain an optically active enantiomer or diastereomer of Formula I.

27. The process of claim 25, wherein Y is a leaving group selected from p-toluenesulfonyl, methanesulfonyl, trifluoromethanesulfonyl, bromo and iodo.

28. The process of claim 1, wherein $B_{NUC}$ is guanine.

29. The process of claim 7, wherein $B_{NUC}$ is guanine.

30. The process of claim 29, wherein $L^a$ is $C_{13}$-$C_{29}$ heteroalkyl.

31. The process of claim 30, wherein $L^a$ is $(CH_2)_2$—O—$(CH_2)_{17}CH_3$.

32. The process of claim 31, wherein $X^a$ is hydrogen.

33. The process of claim 13, wherein $B_{NUC}$ is guanine.

34. The process of claim 19, wherein $B_{NUC}$ is guanine.

35. The process of claim 34, wherein $L^a$ is $C_{13}$-$C_{29}$ heteroalkyl.

36. The process of claim 35, wherein $L^a$ is $(CH_2)_2$—O—$(CH_2)_{17}CH_3$.

37. The process of claim 36, wherein $X^a$ is hydrogen.

38. The process of claim 25, wherein $B_{NUC}$ is guanine.

39. The process of claim 38, wherein $L^a$ is $C_{13}$-$C_{29}$ heteroalkyl.

40. The process of claim 39, wherein $L^a$ is $(CH_2)_2$—O—$(CH_2)_{17}CH_3$.

41. The process of claim 40, wherein $X^a$ is hydrogen.

42. A process comprising combining benzyl alcohol, a coupling agent, a base, an organic solvent, and a compound of formula:

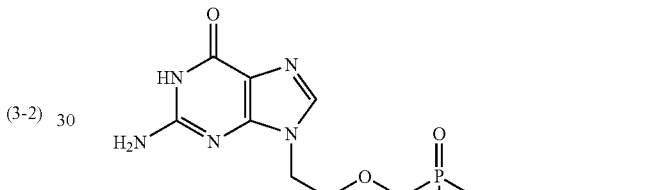

thereby obtaining a compound of formula:

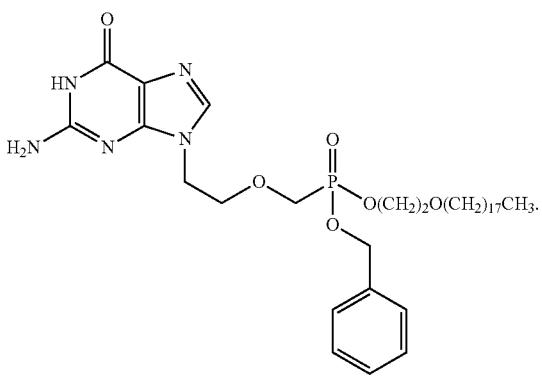

43. The process of claim 42, wherein the coupling agent is (benzotriazol-1-yloxy)-tripyrrolidinophosphonium hexafluorophosphate.

44. The process of claim 42, wherein the base is N,N-diisopropylethylamine.

45. The process of claim 42, wherein the organic solvent is N,N-dimethylformamide.

* * * * *